(12) United States Patent
Simmons

(10) Patent No.: US 11,596,165 B2
(45) Date of Patent: *Mar. 7, 2023

(54) COMPOSITIONS, THEIR USE, AND METHODS FOR THEIR FORMATION

(71) Applicant: Cambridge Glycoscience Ltd, Cambridge (GB)

(72) Inventor: Thomas J. Simmons, Cambridge (GB)

(73) Assignee: CAMBRIDGE GLYCOSCIENCE LTD, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,199

(22) Filed: Jan. 7, 2022

(65) Prior Publication Data
US 2022/0132897 A1    May 5, 2022

Related U.S. Application Data

(63) Continuation of application No. 17/229,628, filed on Apr. 13, 2021, which is a continuation of application No. 16/844,960, filed on Apr. 9, 2020, now Pat. No. 11,006,658, which is a continuation of application No. PCT/EP2019/072026, filed on Aug. 16, 2019.

(60) Provisional application No. 62/764,660, filed on Aug. 15, 2018.

(51) Int. Cl.
*A23L 27/30* (2016.01)
*A23L 29/30* (2016.01)
*A23L 33/24* (2016.01)

(52) U.S. Cl.
CPC .............. *A23L 27/33* (2016.08); *A23L 29/30* (2016.08); *A23L 33/24* (2016.08); *A23V 2002/00* (2013.01)

(58) Field of Classification Search
CPC ........... A23L 27/33; A23L 29/30; A23L 33/20
USPC ....................................................... 426/658
See application file for complete search history.

(56) References Cited

U.S. PATENT DOCUMENTS

| | | | |
|---|---|---|---|
| 6,667,066 B2 | 12/2003 | Labeille et al. |
| 7,033,626 B2 | 4/2006 | Spendler et al. |
| 7,151,079 B2 | 12/2006 | Fack et al. |
| 7,378,103 B2 | 5/2008 | Kanji et al. |
| 7,598,069 B2 | 10/2009 | Felby et al. |
| 7,754,456 B2 | 7/2010 | Penttila et al. |
| 7,993,463 B2 | 8/2011 | Griffin et al. |
| 7,993,890 B2 | 8/2011 | Soerensen et al. |
| 8,057,840 B2 | 11/2011 | Harrison et al. |
| 8,202,842 B2 | 6/2012 | Sinclair et al. |
| 8,247,200 B2 | 8/2012 | Foody et al. |
| 8,663,952 B2 | 3/2014 | He et al. |
| 8,679,794 B2 | 3/2014 | Muniglia et al. |
| 8,709,763 B2 | 4/2014 | Lali et al. |
| 8,894,771 B2 | 11/2014 | Floyd et al. |
| 8,927,038 B2 | 1/2015 | Broekaert et al. |
| 8,956,846 B2 | 2/2015 | Ben Chaabane et al. |
| 9,062,328 B2 | 6/2015 | Medoff |
| 9,090,916 B2 | 7/2015 | Casanave et al. |
| 9,113,652 B2 | 8/2015 | Pilling et al. |
| 9,150,895 B2 | 10/2015 | Kurihara et al. |
| 9,410,216 B2 | 8/2016 | Eyal et al. |
| 9,458,482 B2 | 10/2016 | Bals et al. |
| 9,580,729 B2 | 2/2017 | Noda et al. |
| 9,605,291 B2 | 3/2017 | Yamada et al. |
| 9,663,836 B2 | 5/2017 | Jansen et al. |
| 9,670,516 B2 | 6/2017 | Minamino et al. |
| 9,783,860 B2 | 10/2017 | Floyd et al. |
| 9,797,021 B2 | 10/2017 | Floyd et al. |
| 9,920,309 B2 | 3/2018 | Reisinger et al. |
| 9,920,346 B2 | 3/2018 | Funada et al. |
| 9,955,707 B2 | 5/2018 | Delbaere |
| 9,963,725 B2 | 5/2018 | Lali et al. |
| 9,963,728 B2 | 5/2018 | Minamino et al. |
| 9,982,280 B2 | 5/2018 | Noordam et al. |
| 9,988,657 B2 | 6/2018 | Nagy et al. |
| 10,041,138 B1 | 8/2018 | Eyal et al. |
| 10,131,923 B2 | 11/2018 | Noordam et al. |
| 10,167,576 B2 | 1/2019 | Chao et al. |
| 10,174,351 B2 | 1/2019 | Smits et al. |
| 10,253,343 B2 | 4/2019 | Yamada et al. |
| 10,351,633 B2 | 7/2019 | Cheng et al. |
| 10,368,569 B2 | 8/2019 | Toksoz et al. |
| 10,426,791 B2 | 10/2019 | Speelmans et al. |
| 10,428,362 B2 | 10/2019 | Nagy et al. |
| 10,472,657 B2 | 11/2019 | Nagy et al. |
| 10,487,369 B2 | 11/2019 | Floyd et al. |
| 10,557,153 B2 | 2/2020 | De et al. |
| 10,563,238 B2 | 2/2020 | Yamada et al. |
| 10,570,432 B2 | 2/2020 | Nishino et al. |
| 10,633,461 B2 | 4/2020 | Richard et al. |
| 10,752,705 B2 | 8/2020 | Geremia et al. |
| 10,858,712 B2 | 12/2020 | Kilambi et al. |

(Continued)

FOREIGN PATENT DOCUMENTS

| | | |
|---|---|---|
| CA | 2831543 A1 | 10/2012 |
| CN | 101899488 A | 12/2010 |
| CN | 102925516 A | 2/2013 |
| CN | 106367449 A | 2/2017 |
| CN | 107746866 A | 3/2018 |

(Continued)

OTHER PUBLICATIONS

Aachary et al. Xylooligosaccharides (XOS) as an Emerging Prebiotic: Microbial Synthesis, Utilization, Structural Characterization, Bioactive Properties, and Applications. Comprehensive Reviews in Food Science and Food Safety, vol. 10, pp. 2-16 (2011).

(Continued)

*Primary Examiner* — Jyoti Chawla
(74) *Attorney, Agent, or Firm* — Wilson Sonsini Goodrich & Rosati

(57) ABSTRACT

Compositions comprising polysaccharides and oligosaccharides are provided. Methods for the formation of the compositions, including the enzymatic production of the oligosaccharides, and the uses of the compositions in foodstuffs, cosmetics, and nutraceuticals are also provided.

20 Claims, 14 Drawing Sheets

Specification includes a Sequence Listing.

(56) References Cited

U.S. PATENT DOCUMENTS

| | | |
|---|---|---|
| 11,006,658 B2 | 5/2021 | Simmons |
| 11,134,709 B2 | 10/2021 | Hofmekler |
| 11,151,848 B2 | 10/2021 | Strong et al. |
| 11,180,786 B2 | 11/2021 | Cao et al. |
| 11,193,005 B2 | 12/2021 | Behabtu |
| 11,208,674 B2 | 12/2021 | Konishi et al. |
| 11,248,247 B2 | 2/2022 | Simmons |
| 11,253,818 B2 | 2/2022 | Kurihara et al. |
| 11,254,957 B2 | 2/2022 | Retsina et al. |
| 11,279,960 B2 | 3/2022 | Kasahara et al. |
| 11,297,865 B2 | 4/2022 | Simmons et al. |
| 2003/0091691 A1 | 5/2003 | Olsen et al. |
| 2007/0248649 A1 | 10/2007 | Sawatzki et al. |
| 2009/0042266 A1 | 2/2009 | Vehmaanpera et al. |
| 2009/0062232 A1 | 3/2009 | Fujikawa et al. |
| 2009/0305935 A1 | 12/2009 | Cascao-Pereira et al. |
| 2011/0143402 A1 | 6/2011 | De Laat et al. |
| 2011/0171710 A1 | 7/2011 | Yu et al. |
| 2012/0035127 A1 | 2/2012 | Goffin et al. |
| 2012/0115192 A1 | 5/2012 | Lali et al. |
| 2012/0135500 A1 | 5/2012 | Aehle et al. |
| 2012/0264873 A1 | 10/2012 | Eyal et al. |
| 2013/0095531 A1 | 4/2013 | Schooneveld-Bergmans et al. |
| 2013/0157318 A1 | 6/2013 | Ishikawa et al. |
| 2013/0164420 A1 | 6/2013 | Catani et al. |
| 2015/0065454 A1 | 3/2015 | Dupasquier et al. |
| 2016/0007642 A1 | 1/2016 | Geremia et al. |
| 2016/0081381 A1 | 3/2016 | Medoff |
| 2016/0082022 A1 | 3/2016 | Medoff |
| 2016/0208300 A1 | 7/2016 | Yamada et al. |
| 2016/0326559 A1 | 11/2016 | Funada et al. |
| 2016/0340705 A1 | 11/2016 | Lali et al. |
| 2017/0114371 A1 | 4/2017 | Pedersen et al. |
| 2017/0295805 A1 | 10/2017 | Abu-Hardan et al. |
| 2017/0303548 A1 | 10/2017 | Krogh et al. |
| 2017/0303550 A1 | 10/2017 | Abu-Hardan et al. |
| 2018/0134741 A1 | 5/2018 | Falck |
| 2019/0029272 A1 | 1/2019 | Niemann |
| 2019/0153555 A1 | 5/2019 | Eyal et al. |
| 2019/0233862 A1 | 8/2019 | Cao et al. |
| 2019/0281874 A1 | 9/2019 | Davidek et al. |
| 2020/0071736 A1 | 3/2020 | Hammerer et al. |
| 2020/0113215 A1 | 4/2020 | Hofmekler |
| 2020/0123577 A1 | 4/2020 | De Laat et al. |
| 2020/0128860 A1 | 4/2020 | Hofmekler |
| 2020/0216574 A1 | 7/2020 | Richard et al. |
| 2020/0263265 A1 | 8/2020 | Wu et al. |
| 2020/0299791 A1 | 9/2020 | McKay et al. |
| 2020/0308212 A1 | 10/2020 | Falck |
| 2021/0010043 A1 | 1/2021 | Simmons |
| 2021/0120855 A1 | 4/2021 | Park et al. |
| 2021/0177021 A1 | 6/2021 | Simmons |
| 2021/0207321 A1 | 7/2021 | Loureiro et al. |
| 2021/0227853 A1 | 7/2021 | Pia |
| 2021/0253977 A1 | 8/2021 | Huang et al. |
| 2021/0315245 A1 | 10/2021 | Simmons |
| 2021/0347694 A1 | 11/2021 | Havenith et al. |
| 2021/0392931 A1 | 12/2021 | Simmons et al. |
| 2021/0395284 A1 | 12/2021 | Baur et al. |
| 2022/0017766 A1 | 1/2022 | Kalb |
| 2022/0132896 A1 | 5/2022 | Kannar et al. |

FOREIGN PATENT DOCUMENTS

| | | |
|---|---|---|
| CN | 108157664 A | 6/2018 |
| CN | 108588144 A | 9/2018 |
| EP | 1228098 B1 | 9/2006 |
| EP | 1466926 B1 | 8/2007 |
| EP | 1751296 B1 | 4/2009 |
| EP | 1699974 B1 | 7/2009 |
| EP | 2256208 A1 | 12/2010 |
| EP | 2235195 B1 | 7/2011 |
| EP | 2076271 B1 | 9/2011 |
| EP | 1871400 B1 | 10/2011 |
| EP | 1811038 B1 | 2/2012 |
| EP | 2225387 B1 | 9/2012 |
| EP | 2265127 B1 | 10/2013 |
| EP | 2665823 A1 | 11/2013 |
| EP | 2427565 B1 | 1/2014 |
| EP | 1977652 B1 | 3/2015 |
| EP | 3010352 A1 | 4/2016 |
| EP | 3013155 A1 | 5/2016 |
| EP | 3037005 A1 | 6/2016 |
| EP | 1706477 B1 | 10/2016 |
| EP | 2313514 B1 | 11/2016 |
| EP | 2784156 B1 | 6/2017 |
| EP | 2817374 B1 | 6/2017 |
| EP | 2996492 B1 | 7/2017 |
| EP | 3041941 B1 | 12/2017 |
| EP | 2548966 B1 | 7/2018 |
| EP | 2548965 B1 | 8/2018 |
| EP | 3374315 A1 | 9/2018 |
| EP | 2117322 B1 | 10/2018 |
| EP | 3177728 B1 | 10/2018 |
| EP | 3177729 B1 | 10/2018 |
| EP | 3182830 B1 | 10/2018 |
| EP | 3190189 B1 | 12/2018 |
| EP | 3415632 A1 | 12/2018 |
| EP | 3438272 A1 | 2/2019 |
| EP | 2734633 B1 | 5/2019 |
| EP | 2917359 B1 | 7/2019 |
| EP | 3511418 A1 | 7/2019 |
| EP | 3530743 A1 | 8/2019 |
| EP | 3541870 A1 | 9/2019 |
| EP | 2917355 B1 | 10/2019 |
| EP | 3088530 B1 | 4/2020 |
| EP | 3511418 B1 | 7/2020 |
| EP | 3737769 A1 | 11/2020 |
| EP | 3010352 B1 | 12/2020 |
| EP | 3784045 A1 | 3/2021 |
| EP | 3815540 A1 | 5/2021 |
| EP | 3960772 A1 | 3/2022 |
| EP | 3981379 A2 | 4/2022 |
| EP | 3993644 A1 | 5/2022 |
| EP | 3438272 B1 | 6/2022 |
| JP | 2006087319 A | 4/2006 |
| JP | 2008120789 A | 5/2008 |
| JP | 2009089626 A | 4/2009 |
| KR | 20190133438 A | 12/2019 |
| WO | WO-2012133495 A1 | 10/2012 |
| WO | WO-2013016115 A1 | 1/2013 |
| WO | WO-2013096603 A2 | 6/2013 |
| WO | WO-2013159005 A2 | 10/2013 |
| WO | WO-2014170498 A1 | 10/2014 |
| WO | WO-2015107413 A1 | 7/2015 |
| WO | WO-2017057718 A1 | 4/2017 |
| WO | WO-2018106656 A1 | 6/2018 |
| WO | WO-2019010336 A1 | 1/2019 |
| WO | WO-2019055717 A1 | 3/2019 |
| WO | WO-2019102218 A2 | 5/2019 |
| WO | WO-2019138024 A1 | 7/2019 |
| WO | WO-2019162416 A1 | 8/2019 |
| WO | WO-2019227525 A1 | 12/2019 |
| WO | WO-2019229228 A1 | 12/2019 |
| WO | WO-2019239366 A1 | 12/2019 |
| WO | WO-2020009964 A1 | 1/2020 |
| WO | WO-2020035599 A1 | 2/2020 |
| WO | WO-2020097458 A1 | 5/2020 |
| WO | WO-2021032647 A1 | 2/2021 |
| WO | WO-2021 074316 A1 | 4/2021 |
| WO | WO-2021074271 A1 | 4/2021 |
| WO | WO-2021116437 A2 | 6/2021 |
| WO | WO-2021116437 A3 | 7/2021 |
| WO | WO-2021140225 A1 | 7/2021 |
| WO | WO-2021243151 A1 | 12/2021 |
| WO | WO-2021257921 A1 | 12/2021 |
| WO | WO-2022034078 A1 | 2/2022 |
| WO | WO-2022060726 A1 | 3/2022 |
| WO | WO-2022067131 A1 | 3/2022 |

(56) References Cited

FOREIGN PATENT DOCUMENTS

| WO | WO-2022069084 A1 | 4/2022 |
|---|---|---|
| WO | WO-2022073646 A1 | 4/2022 |

OTHER PUBLICATIONS

Bhale et al. Enzymatic activity of *Trichoderma* species. Novus Natural Science Research, 2012, vol. 1, No. 4. 8 pages.

Co-pending U.S. Appl. No. 17/691,931, inventors Simmons; Thomas J. et al., filed Mar. 10, 2022.

Co-pending U.S. Appl. No. 17/837,868, inventor Simmons; Thomas J., filed Jun. 10, 2022.

Co-pending U.S. Appl. No. 17/846,188, inventors Simmons; Thomas J. et al., filed Jun. 22, 2022.

Co-pending U.S. Appl. No. 17/858,609, inventors Simmons; Thomas J. et al., filed Jul. 6, 2022.

Co-pending U.S. Appl. No. 17/865,142, inventors Bartosiak-Jentys; Jeremy et al., filed Jul. 14, 2022.

Green et al. Industrial Fungal Enzymes: An Occupational Allergen Perspective. Journal of Allergy, vol. 2011, Article ID 682574, 11 pages.

Jousse et al. Simplified Kinetic Scheme of Flavor Formation by the Maillard Reaction. Journal of Food Science, vol. 67, No. 7, pp. 2534-2542 (2002).

Lu et al. Extraction and modification of hemicellulose from lignocellulosic biomass: A review. Green Processing and Synthesis 2021; 10: 779-804.

Réhault-Godbert et al. The Golden Egg: Nutritional Value, Bioactivities, and Emerging Benefits for Human Health. Nutrients 11, 684 (Mar. 22, 2019). 26 pages.

Basholli-Salihu et al. The Use of Cellobiose and Fructooligosaccharide on Growth and Stability of Bifidobacterium infantis in Fermented Milk. Food and Nutrition Sciences, 2013, 4, 1301-1306. Published Online Dec. 2013. DOI: http://dx.doi.org/10.4236/fns.2013.412167.

Beldman et al. Application of cellulase and pectinase from fungal origin for the liquefaction and saccharification of biomass. Enzyme and Microbial Technology, vol. 6, Issue 11, pp. 503-507 (Nov. 1984). DOI: https://doi.org/10.1016/0141-0229(84)90004-8.

Brijwani et al. Production of a cellulolytic enzyme system in mixed-culture solid-state fermentation of soybean hulls supplemented with wheat bran. Process Biochemistry, vol. 45, No. 1, 120-128 (2010).

Chen et al. Characterization of a novel xylanase from Aspergillus flavus with the unique properties in production of xylooligosaccharides. J Basic Microbiol. Apr. 2019;59(4):351-358. doi: 10.1002/jobm.201800545. Epub Feb. 12, 2019.

Chica, et al. Semi-rational approaches to engineering enzyme activity: combining the benefits of directed evolution and rational design. Curr Opin Biotechnol. Aug. 2005;16(4):378-84.

Dallabernardina et al. Mixed-Linkage Glucan Oligosaccharides Produced by Automated Glycan Assembly Serve as Tools To Determine the Substrate Specificity of Lichenase. Chemistry. 2017 Mar. 2, 2017;23(13):3191-3196. doi: 10.1002/chem.201605479. Epub Feb. 3, 2017.

Danneels et al. A quantitative indicator diagram for lytic polysaccharide monooxygenases reveals the role of aromatic surface residues in HjLPMO9A regioselectivity. PLoS One. 2017; 12(5): e0178446. Published online May 31, 2017. doi: 10.1371/journal.pone.0178446.

De La Fuente et al. Development of a robust method for the quantitative determination of disaccharides in honey by gas chromatography. J Chromatogr A, 1135 (2006) 212-218.

Dos Santos et al. Structural basis for xyloglucan specificity and α-d-Xylp(1→6)-D-Glcp recognition at the −1 subsite within the GH5 family. Biochemistry. Mar. 17, 2015;54(10):1930-42. doi: 10.1021/acs.biochem.5b00011. Epub Mar. 6, 2015.

EFSA Panel on Dietetic Products, Nutrition and Allergies (NDA) (2018). Safety of xylo-oligosaccharides (XOS) as a novel food pursuant to Regulation (EU) 2015/2283: (Scientific Opinion). E F S A Journal, 16(7), [5361], DOI: https://doi.org/10.2903/j.efsa.2018.5361. 20 pages.

El Khoury et al. Beta Glucan: Health Benefits in Obesity and Metabolic Syndrome. J Nutr Metab. 2012; 2012: 851362. Published online Dec. 11, 2011. doi: 10.1155/2012/851362. 28 pages.

EP18157957.4 Extended European Search Report dated Jul. 13, 2018.

Falck et al. Arabinoxylanase from glycoside hydrolase family 5 is a selective enzyme for production of specific arabinoxylooligosaccharides. Food Chem. Mar. 1, 2018;242:579-584. doi: 10.1016/j.foodchem.2017.09.048. Epub Sep. 12, 2017.

Fanuel et al. The Podospora anserina lytic polysaccharide monooxygenase PaLPMO9H catalyzes oxidative cleavage of diverse plant cell wall matrix glycans. Biotechnol Biofuels. 2017; 10: 63. Published online Mar. 11, 2017. doi: 10.1186/s13068-017-0749-5 . . . .

Gorton. Spare the sugar, bakingbusiness.com. Mar. 31, 2013. Retrieved Sep. 16, 2020 from: https://www.bakingbusiness.com/articles/34774-spare-the-sugar. 8 pages.

Goubet et al. Polysaccharide analysis using carbohydrate gel electrophoresis: a method to study plant cell wall polysaccharides and polysaccharide hydrolases. Anal Biochem. Jan. 1, 2002;300(1):53-68.

GRAS Notification—Claim of GRAS Status (Revised May 21, 2010), Claim of Exemption from the Requirement for Premarket Approval Requirements Pursuant to Proposed 21 CFR § 170.36(c)(1), pp. 000007 and 000015. EAS Consulting Group, LLC, Alexandria, Virginia, USA. Retrieved Dec. 2 from URL: http://wayback.archive-it.org/7993/20171031045331/https://www.fda.gov/downloads/Food/IngredientsPackagingLabeling/GRAS/NoticeInventory/UCM269544.pdf.

Greek Yogurt with Honey Base, Database Accession No. 4046243, Database GNPD online (Jun. 6, 2016). Mintel. 4 pages.

Gupta et al. Xylooligosaccharide—A Valuable Material from Waste to Taste: A Review. J Environ Res Develop, vol. 10, No. 3, pp. 555-563 (Jan.-Mar. 2016).

Hakala et al. Enzyme-aided alkaline extraction of oligosaccharides and polymeric xylan from hardwood kraft pulp. Carbohydr Polym. Mar. 1, 2013;93(1):102-8. doi: 10.1016/j.carbpol.2012.05.013. Epub May 11, 2012.

Hang et al. Enzymatic Production of Soluble Sugars from Corn Husks. LWT—Food Science and Technology, vol. 32, Issue 4, pp. 208-210 (Jun. 1999). DOI: https://doi.org/10.1006/fstl.1998.0530.

Jayapal et al. Value addition to sugarcane bagasse: Xylan extraction and its process optimization for xylooligosaccharides production. Industrial Crops and Products, vol. 42, pp. 14-24 (2013).

Karadeniz et al. Sugar composition of apple juices. European Food Research and Technology, vol. 215, pp. 145-148 (2002).

Kracher et al. Active-site copper reduction promotes substrate binding of fungal lytic polysaccharide monooxygenase and reduces stability. J Biol Chem. Feb. 2, 2018; 293(5): 1676-1687. Published online Dec. 19, 2017. doi: 10.1074/jbc.RA117.000109 . . . .

Kuhad et al. Microbial Cellulases and Their Industrial Applications. Enzyme Res. 2011; 2011: 280696. Published online Sep. 7, 2011. doi: 10.4061/2011/280696.

Lecumberri et al. A diet rich in dietary fiber from cocoa improves lipid profile and reduces malondialdehyde in hypercholesterolemic rats. Nutrition. Apr. 2007;23(4):332-41. doi: 10.1016/j.nut.2007.01.013. Epub Mar. 23, 2007.

Linares-Pastén et al. Structural Considerations on the Use of Endo-Xylanases for the Production of prebiotic Xylooligosaccharides from Biomass. Curr Protein Pept Sci. Jan. 2018; 19(1): 48-67. Published online Jan. 2018. doi: 10.2174/1389203717666160923155209 . . . .

Loose et al. Activation of bacterial lytic polysaccharide monooxygenases with cellobiose dehydrogenase. Protein Sci. Dec. 2016; 25(12): 2175-2186. Published online Sep. 26, 2016. doi: 10.1002/pro.3043.

(56) References Cited

OTHER PUBLICATIONS

Maehara et al. GH30 Glucuronoxylan-Specific Xylanase from Streptomyces turgidiscabies C56. Appl Environ Microbiol. Feb. 15, 2018; 84(4): e01850-17. Published online Jan. 31, 2018. Prepublished online Nov. 27, 2017.

Mathew et al. Xylo- and arabinoxylooligosaccharides from wheat bran by endoxylanases, utilisation by probiotic bacteria, and structural studies of the enzymes. Appl Microbiol Biotechnol. Apr. 2018;102(7):3105-3120. doi: 10.1007/s00253-018-8823-x. Epub Feb. 14, 2018.

Meier et al. Oxygen Activation by Cu LPMOs in Recalcitrant Carbohydrate Polysaccharide Conversion to Monomer Sugars. Chem Rev. Mar. 14, 2018; 118(5): 2593-2635. Published online Nov. 20, 2017. doi: 10.1021/acs.chemrev.7b00421 . . . .

Motta et al. Chapter 10: "A Review of Xylanase Production by the Fermentation of Xylan: Classification, Characterization and Applications," pp. 251-275. In Sustainable Degradation of Lignocellulosic Biomass, Chandel and Da Silva, eds. (May 15, 2013).

Nordberg Karlsson et al. Endo-xylanases as tools for production of substituted xylooligosaccharides with prebiotic properties. Appl Microbiol Biotechnol. 2018; 102(21): 9081-9088. Published online Sep. 8, 2018. doi: 10.1007/S00253-018-9343-4 . . . .

Park et al. Effect of fructo-oligosaccharide and isomalto-oligosaccharide addition on baking quality of frozen dough. Food Chem. Dec. 15, 2016;213:157-162. doi: 10.1016/j.foodchem.2016.06.067. Epub Jun. 21, 2016.

PCT/EP2019/054380 International Search Report and Written Opinion dated Jun. 27, 2019.

PCT/EP2019/072026 International Search Report and Written Opinion dated Dec. 2, 2019.

PCT/EP2020/072929 International Search Report and Written Opinion dated Dec. 8, 2020.

PCT/EP2020/085810 International Search Report and Written Opinion dated Jun. 9, 2021.

PCT/EP2021/050311 International Search Report and Written Opinion dated May 3, 2021.

Qi et al. Application of ultrafiltration and nanofiltration for recycling cellulase and concentrating glucose from enzymatic hydrolyzate of steam exploded wheat straw. Bioresour Technol. Jan. 2012;104:466-72. doi: 10.1016/j.biortech.2011.10.049. Epub Oct. 31, 2011.

Qing et al. "Chapter 19: Xylooligosaccharides Production, Quantification, and Characterization in Context of Lignocellulosic Biomass Pretreatment," pp. 391-415. In Aqueous Pretreatment of Plant Biomass for Biological and Chemical Conversion to Fuels and Chemicals, First Edition. Edited by Charles E. Wyman (2013).

Schmiele et al. Mixolab™ for rheological evaluation of wheat flour partially replaced by soy protein hydrolysate and fructooligosaccharides for bread production. LWT—Food Science and Technology, vol. 76, Part B, pp. 259-269 (Mar. 2017). Available online Jul. 5, 2016. DOI: https://doi.org/10.1016/j.lwt.2016.07.014.

Short-Chain Fructooligosaccharides: Handling/Processing. Technical Evaluation Report. U.S. Department of Agriculture (USDA) Agricultural Marketing Service (AMS). Aug. 11, 2006. Retrieved Sep. 16, 2020 from URL: https://www.ams.usda.gov/sites/default/files/media/Fructooligosaccharides%20TR.pdf, 7 pages.

Simmons et al. An unexpectedly lichenase-stable hexasaccharide from cereal, horsetail and lichen mixed-linkage β-glucans (MLGs): implications for MLG subunit distribution. Phytochemistry. Nov. 2013;95:322-32. doi: 10.1016/j.phytochem.2013.08.003. Epub Sep. 8, 2013.

Simmons et al. Bonds broken and formed during the mixed-linkage glucan : xyloglucan endotransglucosylase reaction catalysed by Equisetum hetero-trans-β-glucanase.Biochem J. Apr. 1, 2017; 474(7): 1055-1070. Published online Mar. 8, 2017. Prepublished online Jan. 20, 2017. doi: 10.1042/BCJ20160935 . . . .

Simmons et al. Structural and electronic determinants of lytic polysaccharide monooxygenase reactivity on polysaccharide substrates. Nat Commun. 2017; 8: 1064. Published online Oct. 20, 2017. doi: 10.1038/s41467-017-01247-3.

Singh et al. Protein Engineering Approaches in the Post-Genomic Era. Curr Protein Pept Sci. 18: 1-11 (2017).

Sun et al. Hydrolysis of lignocellulosic materials for ethanol production: a review. Bioresour Technol. May 2002;83(1):1-11. doi: 10.1016/s0960-8524(01)00212-7.

Tanaka et al. Creation of cellobiose and xylooligosaccharides-coutilizing Escherichia coli displaying both β-glucosidase and β-xylosidase on its cell surface. ACS Synth. Biol. 2014, 3, 7, 446-453. Published online Oct. 24, 2013. DOI: https://doi.org/10.1021/sb400070q.

U.S. Appl. No. 16/844,960 Notice of Allowance dated Feb. 3, 2021.
U.S. Appl. No. 16/844,960 Office Action dated Sep. 22, 2020.
U.S. Appl. No. 17/033,321 Notice of Allowance dated Oct. 6, 2021.
U.S. Appl. No. 17/033,321 Office Action dated Aug. 2, 2021.
U.S. Appl. No. 17/033,321 Office Action dated Jan. 11, 2021.
U.S. Appl. No. 17/083,121 Notice of Allowance dated Aug. 23, 2021.
U.S. Appl. No. 17/083,121 Notice of Allowance dated Decembers, 2021.
U.S. Appl. No. 17/083,121 Office Action dated May 14, 2021.

Villares et al. Lytic polysaccharide monooxygenases disrupt the cellulose fibers structure. Sci Rep. 2017; 7: 40262. Published online Jan. 10, 2017. doi: 10.1038/srep40262.

Wang et al. Relative fermentation of oligosaccharides from human milk and plants by gut microbes. European Food Research and Technology, vol. 243, pp. 133-146 (2017). Published online Jun. 20, 2016.

Watanabe, Eiichi. Membrane Separation in Cellulose Saccharification and Mixed Enzyme Culture Liquid Recycling. [Medicine and Biology, vol. No. 119, Issue No. 3, Sep. 10, 1989], 7 pages.

Xiao et al. Application of Xylo-oligosaccharide in modifying human intestinal function. African Journal of Microbiology Research 6(9):2116-2119 (Mar. 9, 2012).

Zhang et al. Hemicellulose isolation, characterization, and the production of xylo-oligosaccharides from the wastewater of a viscose fiber mill. Carbohydr Polym. May 5, 2016;141:238-43. doi: 10.1016/j.carbpol.2016.01.022. Epub Jan. 12, 2016.

U.S. Appl. No. 17/229,628 Office Action dated Nov. 10, 2022.
U.S. Appl. No. 17/837,868 Office Action dated Oct. 5, 2022.
U.S. Appl. No. 17/846,188 Office Action dated Nov. 28, 2022.

Sample 1
 Sample 2
 Sample 3
 Sample 4

COMPOSITIONS, THEIR USE, AND METHODS FOR THEIR FORMATION

CROSS REFERENCE

This is a continuation application of U.S. application Ser. No. 17/229,628, filed on Apr. 13, 2021, which is a continuation application of U.S. application Ser. No. 16/844,960, filed on Apr. 9, 2020, which claims priority to continuation application International Application No. PCT/EP2019/072026, filed on Aug. 16, 2019, which application claims the benefit of U.S. Provisional Application No. 62/764,660, filed Aug. 15, 2018, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 28, 2021, is named 56406_703_SL.txt and is 106,254 bytes in size.

BACKGROUND

Sugary foods and drinks are an important part of cultural and lifestyle habits across the world, but the sugar they contain has been linked to obesity, diabetes, poor dental health, and disruptive behavior in people. Because of this, consumer preferences have been shifting away from sugar-containing foods, and governments are increasingly implementing regulation to encourage the consumption of less sugar.

As such, industry has been searching for appropriate low-calorie sweeteners for many decades to substitute for sugar in food and beverages. Unfortunately, many sugar substitutes are produced from non-natural resources, and often offer bitter undertones or other unpleasant tastes along with their sweetness, both of which consumers find unappealing. Moreover, while many sweeteners are able to mimic the sweetness of sugar in food and drinks, few are able to mimic the broad range of roles that sugar plays in food, such as adding bulk, modulating texture, providing structure, acting as a preservative, and modulating colour and flavour through caramelisation and Maillard reactions. In addition, many bulking sweeteners that are able to mimic these physical properties of sugar have gastrointestinal tolerance issues that limit their use to levels well below the amount required to replace sugar in a standard Western diet.

Dietary fibre is an important part of a positive diet and helps maintain digestive health and a well-regulated gut flora. Such fibre comprises saccharides of varying chain lengths and types. In addition to being found naturally in a wide spectrum of foods, fibre can also be produced separately and added to other foods during their manufacture.

SUMMARY

Described herein are novel compositions comprising a mixture of oligosaccharides that surprisingly have improved and tunable properties that make them useful as ingredients in foodstuffs, cosmetics, and nutraceuticals, particularly as sugar substitutes. Furthermore, described herein are economical and efficient methods of preparing or manufacturing sugar substitutes comprising one or more oligosaccharides and one or more polysaccharides using enzymatic processes. These processes can be used to create different formulations comprising different types and amounts of the one or more oligosaccharides and the one or more polysaccharides to produce the desired properties.

In some aspects of the disclosure, a consumable composition is described. The consumable composition may comprise cello-oligosaccharides with a degree of polymerization of from two to six. The composition may also comprise at least one more type of oligosaccharide selected from: xylo-oligosaccharides with a degree of polymerization of from two to twelve, mixed-linkage glucan oligosaccharides with a degree of polymerization of from two to five or manno-oligosaccharides having a degree of polymerization of from two to twelve, xyloglucan oligosaccharides having a degree of polymerization of from four to twelve. The cello-oligosaccharide and the one more type of oligosaccharide can form at least 50% of the consumable composition w/w.

In some embodiments, the one more type of oligosaccharide may be xylo-oligosaccharides with a degree of polymerization of from two to twelve.

In some embodiments the one more type of oligosaccharide may be mixed-linkage glucan oligosaccharides with a degree of polymerization of from two to five.

In some embodiments the one more type of oligosaccharide may be manno-oligosaccharides having a degree of polymerization of from two to twelve.

In some embodiments the one more type of oligosaccharide may be xyloglucan oligosaccharides having a degree of polymerization of from four to twelve.

In some embodiments the compositions further comprise polysaccharides. In some embodiments the source of the polysaccharides may be a biomass. In some embodiments the biomass comprises corn stover, corn cob, wheat bran, wheat straw, hardwood, softwood, cellulose, chitin, chitosan, xylan, xyloglucan, mixed-linkage glucan, mannan, lignocellulose, or a combination thereof.

In some embodiments, the composition comprises at least 5% cello-oligosaccharides with a degree of polymerization of from two to six w/w.

In some embodiments, the composition comprises at most 90% cello-oligosaccharides with a degree of polymerization of from two to six w/w.

In some embodiments, the composition comprises at most 50% cello-oligosaccharides with a degree of polymerization of from two to six w/w.

In some embodiments, the consumable composition comprises at least 5% polysaccharides w/w.

In some embodiments, the consumable composition comprises at most 50% polysaccharides w/w.

In some embodiments, the cello-oligosaccharides are a mixture comprising cello-oligosaccharides with a degree of polymerization of two, three, four, five, six, or a combination thereof.

In some embodiments, the cello-oligosaccharide mixture comprises at least 5% of cello-oligosaccharides with a degree of polymerization of two w/w.

In some embodiments, the cello-oligosaccharide mixture comprises at least 15% of cello-oligosaccharides with a degree of polymerization of two w/w.

In some embodiments, the cello-oligosaccharide mixture comprises at least 30% of cello-oligosaccharides with a degree of polymerization of two w/w.

In some embodiments, the cello-oligosaccharide mixture comprises at least 50% of cello-oligosaccharides with a degree of polymerization of two w/w.

In some embodiments, the cello-oligosaccharide mixture comprises at least 80% of cello-oligosaccharides with a degree of polymerization of two w/w.

In some embodiments, the cello-oligosaccharide mixture comprises at least 90% of cello-oligosaccharides with a degree of polymerization of two w/w.

In some embodiments, the cello-oligosaccharide mixture comprises at least 5% of cello-oligosaccharides with a degree of polymerization of three w/w.

In some embodiments, the cello-oligosaccharide mixture comprises at least 5% of cello-oligosaccharides with a degree of polymerization of four w/w.

In some embodiments, the cello-oligosaccharide mixture comprises at least 5% of cello-oligosaccharides with a degree of polymerization of five w/w.

In some embodiments, the cello-oligosaccharide mixture comprises at least 5% of cello-oligosaccharides with a degree of polymerization of six w/w.

In some embodiments, the cello-oligosaccharide mixture comprises at most 20% of cello-oligosaccharides with a degree of polymerization of three w/w.

In some embodiments, the cello-oligosaccharide mixture comprises at most 15% of cello-oligosaccharides with a degree of polymerization of four w/w.

In some embodiments, the cello-oligosaccharide mixture comprises at most 10% of cello-oligosaccharides with a degree of polymerization of five w/w.

In some embodiments, the cello-oligosaccharide mixture comprises at most 8% of cello-oligosaccharides with a degree of polymerization of six w/w.

In some embodiments, the xylo-oligosaccharides are a mixture comprising xylo-oligosaccharides with a degree of polymerization of two, three, four, five, six, seven, eight, nine, ten, eleven, twelve, or a combination thereof.

In some embodiments, the composition comprises at least 5% xylo-oligosaccharides with a degree of polymerization of from two to twelve w/w.

In some embodiments, the xylo-oligosaccharide mixture comprises at least 4% of xylo-oligosaccharides with a degree of polymerization of two w/w.

In some embodiments, the xylo-oligosaccharide mixture comprises at least 15% of xylo-oligosaccharides with a degree of polymerization of two w/w.

In some embodiments, the xylo-oligosaccharide mixture comprises at least 30% of xylo-oligosaccharides with a degree of polymerization of two w/w.

In some embodiments, the xylo-oligosaccharide mixture comprises at least 50% of xylo-oligosaccharides with a degree of polymerization of two w/w.

In some embodiments, the xylo-oligosaccharide mixture comprises at least 70% of xylo-oligosaccharides with a degree of polymerization of two w/w.

In some embodiments, the xylo-oligosaccharide mixture comprises at least 5% of xylo-oligosaccharides with a degree of polymerization of three w/w.

In some embodiments, the xylo-oligosaccharide mixture comprises at least 8% of xylo-oligosaccharides with a degree of polymerization of three w/w.

In some embodiments, the xylo-oligosaccharide mixture comprises at least 15% of xylo-oligosaccharides with a degree of polymerization of three w/w.

In some embodiments, the xylo-oligosaccharide mixture comprises at least 5% of xylo-oligosaccharides with a degree of polymerization of four w/w.

In some embodiments, the xylo-oligosaccharide mixture comprises at least 5% of xylo-oligosaccharides with a degree of polymerization of five w/w.

In some embodiments, the xylo-oligosaccharide mixture comprises at least 10% of xylo-oligosaccharides with a degree of polymerization of six w/w.

In some embodiments, the xylo-oligosaccharide mixture comprises at least 3% of xylo-oligosaccharides with a degree of polymerization of seven w/w.

In some embodiments, the xylo-oligosaccharide mixture comprises at least 4% of xylo-oligosaccharides with a degree of polymerization of eight w/w.

In some embodiments, the xylo-oligosaccharide mixture comprises at least 2% of xylo-oligosaccharides with a degree of polymerization of nine w/w.

In some embodiments, the xylo-oligosaccharide mixture comprises at least 1% of xylo-oligosaccharides with a degree of polymerization of ten w/w.

In some embodiments, the xylo-oligosaccharide mixture comprises at least 1% of xylo-oligosaccharides with a degree of polymerization of eleven w/w.

In some embodiments, the xylo-oligosaccharide mixture comprises at most 15% of xylo-oligosaccharides with a degree of polymerization of four w/w.

In some embodiments, the xylo-oligosaccharide mixture comprises at most 15% of xylo-oligosaccharides with a degree of polymerization of five w/w.

In some embodiments, the xylo-oligosaccharide mixture comprises at most 20% of xylo-oligosaccharides with a degree of polymerization of six w/w.

In some embodiments, the xylo-oligosaccharide mixture comprises at most 15% of xylo-oligosaccharides with a degree of polymerization of seven w/w.

In some embodiments, the xylo-oligosaccharide mixture comprises at most 20% of xylo-oligosaccharides with a degree of polymerization of eight w/w.

In some embodiments, the xylo-oligosaccharide mixture comprises at most 10% of xylo-oligosaccharides with a degree of polymerization of nine w/w.

In some embodiments, the xylo-oligosaccharide mixture comprises at most 5% of xylo-oligosaccharides with a degree of polymerization of ten w/w.

In some embodiments, the xylo-oligosaccharide mixture comprises at most 5% of xylo-oligosaccharides with a degree of polymerization of eleven w/w.

In some embodiments, the manno-oligosaccharides are a mixture comprising manno-oligosaccharides with a degree of polymerization of two, three, four, five, six, seven, eight, nine, ten, eleven, twelve, or a combination thereof.

In some embodiments, the manno-oligosaccharide mixture comprises at least 4% of manno-oligosaccharides with a degree of polymerization of two w/w.

In some embodiments, the manno-oligosaccharide mixture comprises at least 15% of manno-oligosaccharides with a degree of polymerization of two w/w.

In some embodiments, the manno-oligosaccharide mixture comprises at least 30% of manno-oligosaccharides with a degree of polymerization of two w/w.

In some embodiments, the manno-oligosaccharide mixture comprises at least 50% of manno-oligosaccharides with a degree of polymerization of two w/w.

In some embodiments, the manno-oligosaccharide mixture comprises at least 70% of manno-oligosaccharides with a degree of polymerization of two w/w.

In some embodiments, the manno-oligosaccharide mixture comprises at least 5% of manno-oligosaccharides with a degree of polymerization of three w/w.

In some embodiments, the manno-oligosaccharide mixture comprises at least 8% of manno-oligosaccharides with a degree of polymerization of three w/w.

In some embodiments, the manno-oligosaccharide mixture comprises at least 15% of manno-oligosaccharides with a degree of polymerization of three w/w.

In some embodiments, the manno-oligosaccharide mixture comprises at least 5% of manno-oligosaccharides with a degree of polymerization of four w/w.

In some embodiments, the manno-oligosaccharide mixture comprises at least 5% of manno-oligosaccharides with a degree of polymerization of five w/w.

In some embodiments, the manno-oligosaccharide mixture comprises at least 10% of manno-oligosaccharides with a degree of polymerization of six w/w.

In some embodiments, the manno-oligosaccharide mixture comprises at least 3% of manno-oligosaccharides with a degree of polymerization of seven w/w.

In some embodiments, the manno-oligosaccharide mixture comprises at least 4% of manno-oligosaccharides with a degree of polymerization of eight w/w.

In some embodiments, the manno-oligosaccharide mixture comprises at least 2% of manno-oligosaccharides with a degree of polymerization of nine w/w.

In some embodiments, the manno-oligosaccharide mixture comprises at least 1% of manno-oligosaccharides with a degree of polymerization of ten w/w.

In some embodiments, the manno-oligosaccharide mixture comprises at least 1% of manno-oligosaccharides with a degree of polymerization of eleven w/w.

In some embodiments, the manno-oligosaccharide mixture comprises at most 15% of manno-oligosaccharides with a degree of polymerization of four w/w.

In some embodiments, the manno-oligosaccharide mixture comprises at most 15% of manno-oligosaccharides with a degree of polymerization of five w/w.

In some embodiments, the manno-oligosaccharide mixture comprises at most 20% of manno-oligosaccharides with a degree of polymerization of six w/w.

In some embodiments, the manno-oligosaccharide mixture comprises at most 15% of manno-oligosaccharides with a degree of polymerization of seven w/w.

In some embodiments, the manno-oligosaccharide mixture comprises at most 20% of manno-oligosaccharides with a degree of polymerization of eight w/w.

In some embodiments, the manno-oligosaccharide mixture comprises at most 10% of manno-oligosaccharides with a degree of polymerization of nine w/w.

In some embodiments, the manno-oligosaccharide mixture comprises at most 5% of manno-oligosaccharides with a degree of polymerization of ten w/w.

In some embodiments, the manno-oligosaccharide mixture comprises at most 5% of manno-oligosaccharides with a degree of polymerization of eleven w/w.

In some embodiments, the composition comprises at least 5% mixed-linkage glucan oligosaccharides with a degree of polymerization of from two to five w/w.

The consumable composition may be used as an ingredient in a finished product.

In some embodiments, the concentration of the consumable composition in the ingredient may be at least 20% w/w.

In some embodiments, the concentration of the consumable composition in the ingredient may be at least 40% w/w.

In some embodiments, the concentration of the consumable composition in the ingredient may be at least 60% w/w.

In some embodiments, the finished product may be a foodstuff.

In some embodiments, the finished product may be a cosmetic.

In some embodiments, the finished product may be a nutraceutical.

The concentration of the consumable composition in the finished product may be at least 1% w/w.

The concentration of the consumable composition in the finished product may be at least 2% w/w.

The concentration of the consumable composition in the finished product may be at least 5% w/w.

The concentration of the consumable composition in the finished product may be at least 10% w/w.

The composition may comprise less than 5% monosaccharides w/w.

In some embodiments, the composition may be used as a sweetener composition.

The sweetness of the compositions may be comparable to a control composition, wherein the control composition comprises primarily monosaccharides, disaccharides or a combination thereof.

The sweetness of the compositions may be higher than the sweetness of a control composition, wherein the control composition comprises primarily monosaccharides, disaccharides or a combination thereof.

In some embodiments, the composition may be used as a binding composition.

In some embodiments, the binding properties of the composition are comparable to a control composition, wherein the control composition comprises primarily monosaccharides, disaccharides or a combination thereof.

In some embodiments, the binding properties of the compositions are higher than the binding properties of a control composition, wherein the control composition comprises primarily monosaccharides, disaccharides or a combination thereof.

In some embodiments, the composition may be used as a fibre content enhancer.

In some embodiments, the fibre content of the compositions may be comparable to a control composition, wherein the control composition comprises primarily monosaccharides, disaccharides or a combination thereof.

In some embodiments, the fibre content of the compositions may be higher than the fibre content of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily one type of oligosaccharide.

In one aspect, a consumable composition is provided herein. The composition may comprise xylo-oligosaccharides with a degree of polymerization of from two to twelve. The composition may further comprise at least one more type of oligosaccharide selected from: cello-oligosaccharides with a degree of polymerization of from two to six, mixed-linkage glucan oligosaccharides with a degree of polymerization of from two to five, manno-oligosaccharides having a degree of polymerization of from two to twelve or xyloglucan oligosaccharides having a degree of polymerization of from four to twelve. The xylo-oligosaccharide and the one more type of oligosaccharide may form at least 50% of the consumable composition w/w.

In some embodiments, the one more type of oligosaccharide may be cello-oligosaccharides with a degree of polymerization of from two to six.

In some embodiments, the one more type of oligosaccharide may be mixed-linkage glucan oligosaccharides with a degree of polymerization of from two to five.

In some embodiments, the one more type of oligosaccharide may be manno-oligosaccharides having a degree of polymerization of from two to twelve.

In some embodiments, the one more type of oligosaccharide may be xyloglucan oligosaccharides having a degree of polymerization of from four to twelve.

In some embodiments, the composition further comprises polysaccharides.

In some embodiments, the source of the polysaccharides may be a biomass.

In some embodiments, the biomass comprises corn stover, corn cob, wheat bran, wheat straw, hardwood, softwood, cellulose, chitin, chitosan, xylan, xyloglucan, mixed-linkage glucan, mannan, lignocellulose, or a combination thereof.

In some embodiments, the composition comprises at least 5% cello-oligosaccharides with a degree of polymerization of from two to six w/w.

In some embodiments, the composition comprises at most 90% cello-oligosaccharides with a degree of polymerization of from two to six w/w.

In some embodiments, the composition comprises at most 50% cello-oligosaccharides with a degree of polymerization of from two to six w/w.

In some embodiments, the consumable composition comprises at least 5% polysaccharides w/w.

In some embodiments, the consumable composition comprises at most 50% polysaccharides w/w.

In some embodiments, the cello-oligosaccharides are a mixture comprising cello-oligosaccharides with a degree of polymerization of two, three, four, five, six, or a combination thereof.

In some embodiments, the cello-oligosaccharide mixture comprises at least 5% of cello-oligosaccharides with a degree of polymerization of two w/w.

In some embodiments, the cello-oligosaccharide mixture comprises at least 15% of cello-oligosaccharides with a degree of polymerization of two w/w.

In some embodiments, the cello-oligosaccharide mixture comprises at least 30% of cello-oligosaccharides with a degree of polymerization of two w/w.

In some embodiments, the cello-oligosaccharide mixture comprises at least 50% of cello-oligosaccharides with a degree of polymerization of two w/w.

In some embodiments, the cello-oligosaccharide mixture comprises at least 80% of cello-oligosaccharides with a degree of polymerization of two w/w.

In some embodiments, the cello-oligosaccharide mixture comprises at least 90% of cello-oligosaccharides with a degree of polymerization of two w/w.

In some embodiments, the cello-oligosaccharide mixture comprises at least 5% of cello-oligosaccharides with a degree of polymerization of three w/w.

In some embodiments, the cello-oligosaccharide mixture comprises at least 5% of cello-oligosaccharides with a degree of polymerization of four w/w.

In some embodiments, the cello-oligosaccharide mixture comprises at least 5% of cello-oligosaccharides with a degree of polymerization of five w/w.

In some embodiments, the cello-oligosaccharide mixture comprises at least 5% of cello-oligosaccharides with a degree of polymerization of six w/w.

In some embodiments, the cello-oligosaccharide mixture comprises at most 20% of cello-oligosaccharides with a degree of polymerization of three w/w.

In some embodiments, the cello-oligosaccharide mixture comprises at most 15% of cello-oligosaccharides with a degree of polymerization of four w/w.

In some embodiments, the cello-oligosaccharide mixture comprises at most 10% of cello-oligosaccharides with a degree of polymerization of five w/w.

In some embodiments, the cello-oligosaccharide mixture comprises at most 8% of cello-oligosaccharides with a degree of polymerization of six w/w.

In some embodiments, the xylo-oligosaccharides are a mixture comprising xylo-oligosaccharides with a degree of polymerization of two, three, four, five, six, seven, eight, nine, ten, eleven, twelve, or a combination thereof.

In some embodiments, the composition comprises at least 5% xylo-oligosaccharides with a degree of polymerization of from two to twelve w/w.

In some embodiments, the xylo-oligosaccharide mixture comprises at least 4% of xylo-oligosaccharides with a degree of polymerization of two w/w.

In some embodiments, the xylo-oligosaccharide mixture comprises at least 15% of xylo-oligosaccharides with a degree of polymerization of two w/w.

In some embodiments, the xylo-oligosaccharide mixture comprises at least 30% of xylo-oligosaccharides with a degree of polymerization of two w/w.

In some embodiments, the xylo-oligosaccharide mixture comprises at least 50% of xylo-oligosaccharides with a degree of polymerization of two w/w.

In some embodiments, the xylo-oligosaccharide mixture comprises at least 70% of xylo-oligosaccharides with a degree of polymerization of two w/w.

In some embodiments, the xylo-oligosaccharide mixture comprises at least 5% of xylo-oligosaccharides with a degree of polymerization of three w/w.

In some embodiments, the xylo-oligosaccharide mixture comprises at least 8% of xylo-oligosaccharides with a degree of polymerization of three w/w.

In some embodiments, the xylo-oligosaccharide mixture comprises at least 15% of xylo-oligosaccharides with a degree of polymerization of three w/w.

In some embodiments, the xylo-oligosaccharide mixture comprises at least 5% of xylo-oligosaccharides with a degree of polymerization of four w/w.

In some embodiments, the xylo-oligosaccharide mixture comprises at least 5% of xylo-oligosaccharides with a degree of polymerization of five w/w.

In some embodiments, the xylo-oligosaccharide mixture comprises at least 10% of xylo-oligosaccharides with a degree of polymerization of six w/w.

In some embodiments, the xylo-oligosaccharide mixture comprises at least 3% of xylo-oligosaccharides with a degree of polymerization of seven w/w.

In some embodiments, the xylo-oligosaccharide mixture comprises at least 4% of xylo-oligosaccharides with a degree of polymerization of eight w/w.

In some embodiments, the xylo-oligosaccharide mixture comprises at least 2% of xylo-oligosaccharides with a degree of polymerization of nine w/w.

In some embodiments, the xylo-oligosaccharide mixture comprises at least 1% of xylo-oligosaccharides with a degree of polymerization of ten w/w.

In some embodiments, the xylo-oligosaccharide mixture comprises at least 1% of xylo-oligosaccharides with a degree of polymerization of eleven w/w.

In some embodiments, the xylo-oligosaccharide mixture comprises at most 15% of xylo-oligosaccharides with a degree of polymerization of four w/w.

In some embodiments, the xylo-oligosaccharide mixture comprises at most 15% of xylo-oligosaccharides with a degree of polymerization of five w/w.

In some embodiments, the xylo-oligosaccharide mixture comprises at most 20% of xylo-oligosaccharides with a degree of polymerization of six w/w.

In some embodiments, the xylo-oligosaccharide mixture comprises at most 15% of xylo-oligosaccharides with a degree of polymerization of seven w/w.

In some embodiments, the xylo-oligosaccharide mixture comprises at most 20% of xylo-oligosaccharides with a degree of polymerization of eight w/w.

In some embodiments, the xylo-oligosaccharide mixture comprises at most 10% of xylo-oligosaccharides with a degree of polymerization of nine w/w.

In some embodiments, the xylo-oligosaccharide mixture comprises at most 5% of xylo-oligosaccharides with a degree of polymerization of ten w/w.

In some embodiments, the xylo-oligosaccharide mixture comprises at most 5% of xylo-oligosaccharides with a degree of polymerization of eleven w/w.

In some embodiments, the manno-oligosaccharides are a mixture comprising manno-oligosaccharides with a degree of polymerization of two, three, four, five, six, seven, eight, nine, ten, eleven, twelve, or a combination thereof.

In some embodiments, the composition comprises at least 5% mixed-linkage glucan oligosaccharides with a degree of polymerization of from two to five w/w.

In some embodiments, the consumable composition may be used as an ingredient in a finished product.

In some embodiments, the concentration of the consumable composition in the ingredient may be at least 20% w/w.

In some embodiments, the concentration of the consumable composition in the ingredient may be at least 40% w/w.

In some embodiments, the concentration of the consumable composition in the ingredient may be at least 60% w/w.

In some embodiments, the finished product may be a foodstuff.

In some embodiments, the finished product may be a cosmetic.

In some embodiments, the finished product may be a nutraceutical.

In some embodiments, the concentration of the consumable composition in the finished product may be at least 1% w/w.

In some embodiments, the concentration of the consumable composition in the finished product may be at least 2% w/w.

In some embodiments, the concentration of the consumable composition in the finished product may be at least 5% w/w.

In some embodiments, the concentration of the consumable composition in the finished product may be at least 10% w/w.

In some embodiments, the composition comprises less than 5% monosaccharides w/w.

In some embodiments, the composition may be used as a sweetener composition.

In some embodiments, the sweetness of the compositions may be comparable to a control composition, wherein the control composition comprises primarily monosaccharides, disaccharides or a combination thereof.

In some embodiments, the sweetness of the compositions may be higher than the sweetness of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily monosaccharides, disaccharides or a combination thereof.

In some embodiments, the gastro-intestinal tolerance of the composition may be comparable or higher than the gastro-intestinal tolerance of a control composition, wherein the control composition comprises primarily one type of oligosaccharide.

In one aspect, provided herein is a foodstuff ingredient, cosmetic ingredient, or nutraceutical ingredient composition comprising at least two oligosaccharides. The oligosaccharides may be selected from the list consisting of cello-oligosaccharides having a degree of polymerisation of from two to six, xylo-oligosaccharides having a degree of polymerisation of from two to twelve, mixed-linkage glucan oligosaccharides having a degree of polymerisation of from two to five, manno-oligosaccharides having a degree of polymerisation of from two to twelve, xyloglucan oligosaccharides having a degree of polymerisation of from four to twelve, and chito-oligosaccharides having a degree of polymerisation of from two to twelve. The composition may comprise at least 10% by dry weight of each of the at least two oligosaccharides; wherein the ingredient comprises at least 50% by dry weight of saccharide present.

In some embodiments, the composition comprises at least 20% by dry weight, preferably at least 30% by dry weight, cello-oligosaccharides having a degree of polymerisation of from two to six.

In some embodiments, the composition comprises at least 20% by dry weight, preferably at least 30% by dry weight, xylo-oligosaccharides having a degree of polymerisation of from two to twelve.

In some embodiments, the composition comprises at least 20% by dry weight, preferably at least 30% by dry weight, mixed-linkage glucan oligosaccharides having a degree of polymerisation of from two to five.

In some embodiments, the composition comprises at least 20% by dry weight, preferably at least 30% by dry weight, manno-oligosaccharides having a degree of polymerisation of from two to twelve.

In some embodiments, the composition comprises at least 20% by dry weight, preferably at least 30% by dry weight, xyloglucan oligosaccharides having a degree of polymerisation of from four to twelve.

In some embodiments, the composition comprises at least 20% by dry weight, preferably at least 30% by dry weight, chito-oligosaccharides having a degree of polymerisation of from two to twelve.

In some embodiments, the composition comprises a polysaccharide, preferably a cellulosic polysaccharide, such as cellulose, or a polysaccharide derivative, preferably a cellulose derivative, such as carboxymethylcellulose, or a polysaccharide aggregate, such as lignocellulosic material, preferably undigested lignocellulosic material, such as from an enzymatic reaction that produced the oligosaccharides, preferably the composition comprises from greater than 0 to 40% by dry weight of the polysaccharide, the polysaccharide derivative or the polysaccharide aggregate.

In some embodiments, the composition comprises a phenolic compound, preferably a portion of lignin or a product of lignin breakdown.

In some embodiments, the composition may be in dry form.

In one aspect, provided herein is a foodstuff, cosmetic, or nutraceutical, comprising an oligosaccharide mixture, wherein the oligosaccharide mixture comprises two oligosaccharides. The oligosaccharides may be selected from the list consisting of cello-oligosaccharides having a degree of polymerisation of from two to six, xylo-oligosaccharides having a degree of polymerisation of from two to twelve, mixed-linkage glucan oligosaccharides having a degree of polymerisation of from two to five, manno-oligosaccharides having a degree of polymerisation of from two to twelve, xyloglucan oligosaccharides having a degree of polymerisation of from four to twelve; and chito-oligosaccharides having a degree of polymerisation of from two to twelve. The two oligosaccharides may be present in a ratio of from 1:9 to 9:1, preferably from 1:4 to 4:1, more preferably from 1:3 to 3:1, most preferably 2:3 to 3:2, in relation to each other, optionally wherein the oligosaccharide mixture comprises third oligosaccharides selected from the list. The ingredient may comprise at least 50% by dry weight of the two oligosaccharides present.

In one aspect, described herein is a foodstuff ingredient, cosmetic ingredient, or nutraceutical ingredient composition comprising a saccharide component. The saccharide component may comprise monosaccharides at <5% w/w of total saccharide component (comprising glucose, xylose and/or mannose), disaccharides at >20% w/w of total saccharide component (comprising cello-, xylo- and/or manno-oligosaccharides), wherein the disaccharides are at <50% w/w of total saccharide component, trisaccharides at >5% w/w of total saccharide component (comprising cello-, xylo- and/or manno-oligosaccharides), tetrasaccharides at >2% w/w of total saccharide component (comprising cello-, xylo- and/or manno-oligosaccharides). The total composition may comprise at least 20% by dry weight of saccharides.

In some embodiments, the foodstuff ingredient, cosmetic ingredient, or nutraceutical ingredient composition comprises less than 4% by dry weight of total saccharide component, preferably less than 3% by dry weight of total saccharide component, monosaccharides (comprising glucose, xylose and/or mannose).

In some embodiments, the composition comprises at least 25% by dry weight of total saccharide component, preferably at least 30% by dry weight of total saccharide component, disaccharides (comprising cello-, xylo- and/or manno-oligosaccharides).

In some embodiments, wherein the composition comprises at least 7.5% by dry weight of total saccharide component, preferably at least 10% by dry weight of total saccharide component, trisaccharides (comprising cello-, xylo- and/or manno-oligosaccharides).

In some embodiments, the composition comprises at least 3% by dry weight of total saccharide component, preferably at least 4% by dry weight of total saccharide component, tetrasaccharides (comprising cello-, xylo- and/or manno-oligosaccharides).

In some embodiments, the composition comprises at least 30%, preferably at least 40%, more preferably at least 50%, by dry weight saccharides.

In some embodiments, the composition comprises a polysaccharide, preferably a cellulosic polysaccharide, such as cellulose, or a hemicellulosic polysaccharide, such as xylan, or a polysaccharide derivative, preferably a cellulose derivative, such as carboxymethylcellulose, or a polysaccharide aggregate, such as lignocellulosic material, preferably undigested lignocellulosic material, such as from an enzymatic reaction that produced the oligosaccharides, preferably the composition comprises from greater than 0 to 40% by dry weight of the polysaccharide, the polysaccharide derivative or the polysaccharide aggregate.

In some embodiments, the composition comprises a phenolic compound, preferably a portion of lignin or a product of lignin breakdown.

In one aspect, described herein is a foodstuff ingredient, cosmetic ingredient, or nutraceutical ingredient comprising at least two oligosaccharides derived from lignocellulosic polymers. The oligosaccharides may be selected from the list consisting of cellulose, xylan, mixed-linkage glucan, mannan, xyloglucan, chitin, or a combination thereof. The ingredient can comprise at least 10% by dry weight of each of the at least two oligosaccharides, and at least 50% by dry weight of each of the at least two oligosaccharides.

According to an aspect of the disclosure, there is provided a foodstuff ingredient, cosmetic ingredient, or nutraceutical ingredient composition comprising at least two oligosaccharides selected from the list consisting of:
  i) cello-oligosaccharides having a degree of polymerisation of from two to six;
  ii) xylo-oligosaccharides having a degree of polymerisation of from two to twelve;
  iii) mixed-linkage glucan oligosaccharides having a degree of polymerisation of from two to five;
  iv) manno-oligosaccharides having a degree of polymerisation of from two to twelve;
  v) xyloglucan oligosaccharides having a degree of polymerisation of from four to twelve; and/or
  vi) chito-oligosaccharides having a degree of polymerisation of from two to twelve,
wherein the composition comprises at least 10%, by dry weight of each of the at least two oligosaccharides, and wherein the ingredient comprises at least 50% by dry weight of the two or more oligosaccharides present.

According to another aspect of the disclosure, there is provided the use of an oligosaccharide mixture in the formation of a foodstuff, cosmetic, or nutraceutical, wherein the oligosaccharide mixture comprises two oligosaccharides selected from the list consisting of:
  i) cello-oligosaccharides having a degree of polymerisation from two to six;
  ii) xylo-oligosaccharides having a degree of polymerisation of from two to twelve;
  iii) mixed-linkage glucan oligosaccharides having a degree of polymerisation of from two to five;
  iv) manno-oligosaccharides having a degree of polymerisation of from two to twelve;
  v) xyloglucan oligosaccharides having a degree of polymerisation of from four to twelve; and/or
  vi) chito-oligosaccharides having a degree of polymerisation of from two to twelve,
wherein the two oligosaccharides are present in a ratio of from 1:9 to 9:1, preferably from 1:4 to 4:1, more preferably from 1:3 to 3:1, most preferably 2:3 to 3:2, in relation to each other, optionally wherein the oligosaccharide mixture comprises third oligosaccharides selected from (i) to (vi), and wherein the ingredient comprises at least 50% by dry weight of the two or more oligosaccharides present.

According to another aspect of the disclosure, there is provided a method for producing a foodstuff ingredient, cosmetic ingredient, or nutraceutical ingredient, the ingredient comprising one or more oligosaccharides and one or more polysaccharides, wherein the method comprises the steps of:
  a) forming the one or more oligosaccharides and one or more polysaccharides by an enzymatic reaction, the enzymatic reaction comprising the step of contacting, in a solution or suspension, one or more polysaccharide-cleaving enzymes and one or more feedstocks, wherein the one or more feedstocks comprise sugar cane, corn stover, corn cob, wheat bran, wheat straw, hardwood, softwood, cellulose, chitin, chitosan, xylan, xyloglucan, mixed-linkage glucan, mannan, and/or lignocellulose;

b) separating the one or more oligosaccharides and the one or more polysaccharides from the enzymatic reaction mixture; and/or c) recombining the one or more oligosaccharides and the one or more polysaccharides to form the ingredient.

Optionally, the method for producing an ingredient may include a washing step to separate oligosaccharide fractions before recombining the one or more oligosaccharides.

Optionally, a portion of the one or more oligosaccharides may be recombined with a portion of the one or more polysaccharides to form an ingredient.

Preparing the foodstuff, cosmetic, or nutraceutical ingredient in this way can allow for efficient use of biomass by incorporating oligomeric and polymeric material from the same biomass source. Such preparation can also allow for optional purification, derivatisation and/or other modification, and/or control of oligomeric and polymeric proportions, which can improve the functional properties, nutritional properties, and/or tolerance of the ingredient.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
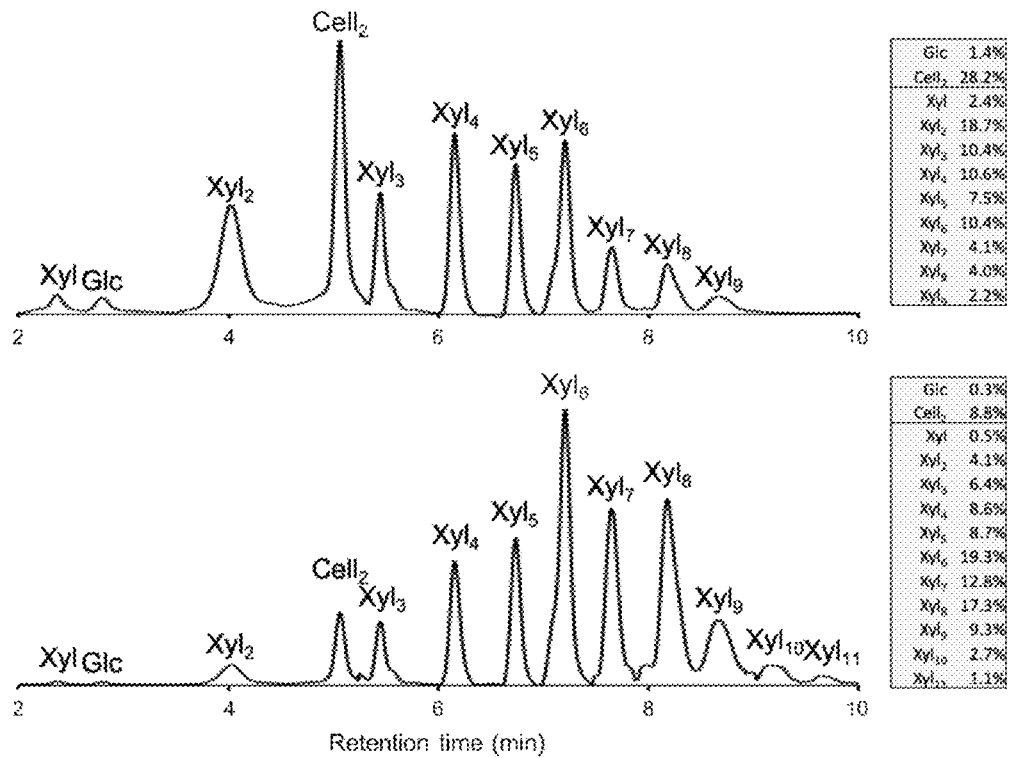
FIG. 1 shows HPLC trace data of oligosaccharide compositions that are expected to be created after digestion with enzymes.

Described herein are saccharide compositions that can be useful in foodstuff, cosmetic, or nutraceutical products. Some embodiments of the present disclosure additionally offer such foodstuff, cosmetic, or nutraceutical products with novel properties. The saccharide compositions may be consumable compositions including cello-oligosaccharides, xylo-oligosaccharides, mixed-linkage glucan oligosaccharides, manno-oligosaccharides, and/or xyloglucan oligosaccharides. Such consumable compositions may be used as sweeteners (e.g., in a foodstuff), binders, and/or fibre content enhancers.

As used herein, "food" and "foodstuff" refer to any item destined for consumption, which may be consumption by a human or by any other animal. It may be food, feed, a beverage, or an ingredient to be used in the production of any of the above.

As used herein, "nutraceutical" refers to any composition introduced into a human or other animal, whether by ingestion, injection, absorption, or any other method, for the purpose of providing nutrition to the human or other animal. Use of such a nutraceutical may take the form of a drink with added dietary fibre, a prebiotic additive, a pill or other capsule, or any other suitable use.

As used herein, "cosmetic" refers to any composition which is intended for use on humans or other animals to increase their aesthetic appeal or prevent future loss of aesthetic appeal, as well as any other compositions known in general parlance as cosmetics. Aesthetic appeal is not limited to visual aesthetics but applies as well to textural or any other appeal. The cosmetic may be mascara, foundation, lip gloss, eyeshadow, eyeliner, primer, lipstick blush, nail polish, bronzer, or any other makeup; shampoo, conditioner, styling mousse, styling gel, hairspray, hair dye, hair wax, or any other hair product; moisturiser, exfoliant, sun cream, cleanser, toothpaste, or a cream, a lotion, ointment or any other composition effective in modifying teeth, skin, hair, or other parts of the body in some aesthetic way. Or the cosmetic may be a composition used as a component of a face mask, brush, hair roller, other styling device, or other solid structure, or any other suitable composition.

As used herein, "polysaccharide" refers to a saccharide polymer of any length greater than about 20 residues. Polysaccharides may be highly branched, lightly branched, or unbranched, may comprise any manner of glycosidic bond in any combination, any number of, for example, α or β linkages, and any combination of monomer types, such as glucose, glucosamine, mannose, xylose, galactose, fucose, fructose, glucuronic acid, arabinose, or derivatives thereof such as any combination of the above monomers decorated with acetyl or other groups. The polysaccharide may be a cellulosic or hemicellulosic polymer, hemicellulosic polymers envisaged including xylan, glucuronoxylan, arabinoxylan, glucomannan, and xyloglucan. In some embodiments, cellulose is the preferred cellulosic polymer.

As used herein, "lignocellulose" refers to polysaccharide-comprising aggregates that are, or are derived from, plant cell wall material. For example, they may comprise one or more of the following polysaccharides associated together: cellulose, xylan, mannan, and mixed-linkage glucan.

As used herein "highly branched," "lightly branched," and "unbranched" refer to the number of side-chains per stretch of main chain in a saccharide. Highly branched saccharides have on average from 4 to 10 side chains per 10 main-chain residues, slightly branched saccharides have on average from 1 to 3 side chains per 10 main-chain residues, and unbranched saccharides have only one main chain and no side chains. The average is calculated by dividing the number of side chains in a saccharide by the number of main-chain residues.

As used herein, "saccharide" refers to any polysaccharide and/or oligosaccharide, such as monosaccharide and/or disaccharide.

As used herein, "oligosaccharide" refers to saccharide polymers having chain lengths less than or equal to about 20 saccharide residues. Oligosaccharides may be highly branched, lightly branched, or unbranched, may comprise glycosidic bonds in any combination, any number of α or β linkages, and any combination of monomer types, such as glucose, glucosamine, mannose, xylose, galactose, fucose, fructose, glucuronic acid, arabinose, or derivatives thereof. Suitable derivatives include the above monomers comprising acetyl or other groups.

As used herein, "monosaccharide" and "disaccharide" refer to saccharide compounds consisting respectively of one or two residues. Monosaccharides are compounds such as glucose, glucosamine, xylose, galactose, fucose, fructose, glucuronic acid, arabinose, galacturonic acid; or epimers or other derivatives thereof. Suitable derivatives include acetyl or other groups. Disaccharides are compounds consisting of two monosaccharides joined via any glycosidic bond.

As used herein, "cello-oligosaccharides" refers to oligosaccharides composed of one or more glucose residues linked by β-1,4-glycosidic bonds, and may be chemically related to that by oxidation, reduction, esterification, epimerisation, or another chemical modification.

As used herein, "xylo-oligosaccharides" refers to oligosaccharides composed primarily of xylose residues (typically linked by β-1,4-glycosidic bonds) and may also contain glucuronic acid residues and/or arabinose residues and/or acetyl groups and/or any other modification, and may be chemically related to that by oxidation, reduction, esterification, epimerisation, or another chemical modification.

As used herein, "mixed-linkage glucan-oligosaccharides" refers to oligosaccharides composed of one or more glucose residues linked by at least one β-1,3-glycosidic bond and at least one β-1,4-glycosidic bond, and may be chemically related to that by oxidation, reduction, esterification, epimerisation, or another chemical modification As used herein, "manno-oligosaccharides" refers to oligosaccharides composed of one or more mannose residues and optionally containing one or more glucose and/or galactose residues, and may be chemically related to that by oxidation, reduction, esterification, epimerisation, or another chemical modification;

As used herein, "chito-oligosaccharides" refers to oligosaccharides composed of one or more glucosamine and/or N-acetyl-glucosamine residues, and may be chemically related to that by oxidation, reduction, esterification, epimerisation, or another chemical modification.

As used herein, "cellulose" refers to polysaccharides composed of glucose residues linked by β-1,4-glycosidic bonds, and derivatives thereof "Xylan" refers to polysaccharides composed of a backbone of xylose residues and may also contain glucuronic acid residues and/or arabinose residues and/or acetyl groups and/or any other modification. "Mixed-linkage glucan" refers to polysaccharides composed of glucose residues linked by β-1,3-glycosidic bonds and β-1,4-glycosidic bonds. "Mannan" refers to polysaccharides composed of greater than 40% mannose residues and optionally containing glucose and/or galactose residues. "Chitin" or "chitosan" refer to polysaccharides composed of glucosamine and/or N-acetyl-glucosamine residues.

The term "about" as used herein can mean within 1 or more than 1 standard deviation. Alternatively, "about" can mean a range of up to 10%, up to 5%, or up to 1% of a given value. For example, about can mean up to ±10%, ±9%, ±8%, ±7%, ±6%, ±5%, ±4%, ±3%, ±2%, or ±1% of a given value.

Compositions

The polysaccharide components of the composition may comprise one or more of any type of polysaccharide. Preferably they comprise cellulose, xylan, mixed-linkage glucan, mannan, xyloglucan, chitin or chitosan, or derivatives of any of the aforementioned polysaccharides.

The composition may comprise various oligosaccharides, and at varying amounts, depending on the desired properties. Suitably, the composition may comprise at least 20% by dry weight, preferably at least 30% by dry weight, cello-oligosaccharides having a degree of polymerisation of from two to six and/or the composition may comprise at least 20% by dry weight, preferably at least 30% by dry weight, xylo-oligosaccharides having a degree of polymerisation of from two to twelve and/or the composition may comprise at least 20% by dry weight, preferably at least 30% by dry weight, mixed-linkage glucan oligosaccharides having a degree of polymerisation of from two to five, and/or the composition may comprise at least 20% by dry weight, preferably at least 30% by dry weight, manno-oligosaccharides having a degree of polymerisation of from two to twelve, and/or the composition may comprise at least 20% by dry weight, preferably at least 30% by dry weight, xyloglucan oligosaccharides having a degree of polymerisation of from four to twelve, and/or the composition may comprise at least 20% by dry weight, preferably at least 30% by dry weight, chito-oligosaccharides having a degree of polymerisation of from two to twelve. The skilled person will understand that the composition can comprise a maximum of 100% by dry weight of the above oligosaccharides, therefore the above embodiment, wherein the oligosaccharides are present in at least 20% by dry weight, does not comprise all six types of oligosaccharides.

In another aspect, provided herein is the use of an oligosaccharide mixture in the formation of a foodstuff, cosmetic, or nutraceutical, wherein the oligosaccharide mixture comprises two oligosaccharides selected from the list consisting of:
  i) cello-oligosaccharides having a degree of polymerisation of from two to six;
  ii) xylo-oligosaccharides having a degree of polymerisation of from two to twelve;
  iii) mixed-linkage glucan oligosaccharides having a degree of polymerisation of from two to five;
  iv) manno-oligosaccharides having a degree of polymerisation of from two to twelve;
  v) xyloglucan oligosaccharides having a degree of polymerisation of from four to ten; and/or
  vi) chito-oligosaccharides having a degree of polymerisation of from two to twelve, wherein the two oligosaccharides may be present in a ratio of from 1:9 to 9:1, preferably 1:4 to 4:1, more preferably from 2:3 to 3:2, in relation to each other.

The amounts of each of the oligosaccharides may be varied depending on the desired properties of the resulting foodstuff, cosmetic, or nutraceutical. Preferably the two oligosaccharides may be present in a ratio of 1:9 to 9:1, preferably 1:2 to 2:1, more preferably 2:3 to 3:2, in relation to each other.

The oligosaccharide mixture may further comprise a third oligosaccharide and a fourth oligosaccharide. The oligosaccharide mixture may comprise a third oligosaccharide, a fourth oligosaccharide, and a fifth oligosaccharide. The oligosaccharide mixture may further comprise a third oligosaccharide, a fourth oligosaccharide, a fifth oligosaccharide, and a sixth oligosaccharide. These oligosaccharides may be selected from the same list as the at least two oligosaccharides as provided above.

Preferred oligosaccharide mixtures of the at least two oligosaccharides may comprise the cello-oligosaccharides, for instance, cello-oligosaccharides in combination with the xylo-oligosaccharides. An alternative preferable composition may comprise cello-oligosaccharides in combination with manno-oligosaccharides.

Optionally, the oligosaccharide mixtures of the at least two oligosaccharides may additionally include a polysaccharide, preferably a cellulosic polysaccharide, such as cellulose, or a polysaccharide derivative, preferably a cellulose derivative, such as carboxymethylcellulose, or a polysaccharide aggregate, preferably a portion of lignocellulosic biomass. Suitably, the ratio in the combination may be from 1:100 to 1:1 polysaccharide/polysaccharide derivative/polysaccharide aggregate:oligosaccharide, preferably from 1:90 to 1:2, preferably from 1:80 to 1:3, preferably from 1:70 to 1:4, and preferably from 1:60 to 1:5. As such, the ratio between the first oligosaccharide, the second oligosaccharide, and the polysaccharide may be from 2:2:1 to 30:30:1, preferably about 3:3:1.

Combinations of Oligosaccharides

A composition may comprise a mixture of one or more oligosaccharides. A mixture of oligosaccharides may comprise two forms of oligosaccharides, for instance, cello-oligosaccharides and xylo-oligosaccharides. A mixture of oligosaccharides may comprise three forms of oligosaccharides, for instance, cello-oligosaccharides, manno-oligosaccharides, and xylo-oligosaccharides. A mixture of oligosaccharides may comprise four forms of oligosaccharides, for instance, cello-oligosaccharides, manno-oligosaccharides, mixed-linkage glucan oligosaccharides, chito-oligosaccharides, and xylo-oligosaccharides.

An oligosaccharide mixture may comprise two forms of oligosaccharides, for example, a first oligosaccharide and a second oligosaccharide. An oligosaccharide mixture may comprise about 5% of a first oligosaccharide and about 95% of a second oligosaccharide w/w. An oligosaccharide mixture may comprise about 10% of a first oligosaccharide and about 90% of a second oligosaccharide w/w. An oligosaccharide mixture may comprise about 15% of a first oligosaccharide and about 85% of a second oligosaccharide w/w. An oligosaccharide mixture may comprise about 20% of a first oligosaccharide and about 80% of a second oligosaccharide w/w. An oligosaccharide mixture may comprise about 25% of a first oligosaccharide and about 75% of a second oligosaccharide w/w. An oligosaccharide mixture may comprise about 30% of a first oligosaccharide and about 70% of a second oligosaccharide w/w. An oligosaccharide mixture may comprise about 35% of a first oligosaccharide and about 65% of a second oligosaccharide w/w. An oligosaccharide mixture may comprise about 40% of a first oligosaccharide and about 50% of a second oligosaccharide w/w. An oligosaccharide mixture may comprise 45% of a first oligosaccharide and 55% of a second oligosaccharide w/w. An oligosaccharide mixture may comprise 50% of a first oligosaccharide and 50% of a second oligosaccharide w/w. An oligosaccharide mixture may comprise 55% of a first oligosaccharide and 45% of a second oligosaccharide w/w. An oligosaccharide mixture may comprise 60% of a first oligosaccharide and 30% of a second oligosaccharide w/w. An oligosaccharide mixture may comprise 65% of a first oligosaccharide and 35% of a second oligosaccharide w/w. An oligosaccharide mixture may comprise 70% of a first oligosaccharide and 30% of a second oligosaccharide w/w. An oligosaccharide mixture may comprise 75% of a first oligosaccharide and 25% of a second oligosaccharide w/w. An oligosaccharide mixture may comprise 80% of a first oligosaccharide and 20% of a second oligosaccharide w/w. An oligosaccharide mixture may comprise 85% of a first oligosaccharide and 15% of a second oligosaccharide w/w. An oligosaccharide mixture may comprise 90% of a first oligosaccharide and 10% of a second oligosaccharide w/w. An oligosaccharide mixture may comprise 95% of a first oligosaccharide and 5% of a second oligosaccharide w/w. In some examples, a first oligosaccharide may be cello-oligosaccharides and a second oligosaccharide may be xylo-oligosaccharides. In some examples, a first oligosaccharide may be cello-oligosaccharides and a second oligosaccharide may be manno-oligosaccharides. In some examples, a first oligosaccharide may be xylo-oligosaccharides and a second oligosaccharide may be manno-oligosaccharides. Other combinations of a first oligosaccharide and a second oligosaccharide are also within the scope of this disclosure.

An oligosaccharide mixture may comprise three forms of oligosaccharides, for example a first oligosaccharide, a second oligosaccharide, and a third oligosaccharide. An oligosaccharide mixture may comprise about 20% of a first oligosaccharide, 40% of a second oligosaccharide, and 40% of a third oligosaccharide w/w. An oligosaccharide mixture may comprise about 30% of a first oligosaccharide, 30% of a second oligosaccharide, and 40% of a third oligosaccharide w/w. An oligosaccharide mixture may comprise about 10% of a first oligosaccharide, 10% of a second oligosaccharide, and 80% of a third oligosaccharide w/w. An oligosaccharide mixture may comprise about 20% of a first oligosaccharide, 20% of a second oligosaccharide, and 60% of a third oligosaccharide w/w. An oligosaccharide mixture may comprise about 20% of a first oligosaccharide, 30% of a second oligosaccharide, and 50% of a third oligosaccharide w/w. In some examples, a first oligosaccharide may be manno-oligosaccharides, a second oligosaccharide may be xylo-oligosaccharides, and a third oligosaccharide may be cello-oligosaccharides. In some examples, a first oligosaccharide may be xyloglucan-oligosaccharides, a second oligosaccharide may be xylo-oligosaccharides, and a third oligosaccharide may be cello-oligosaccharides. Other combinations of a first oligosaccharide, a second oligosaccharide, and a third oligosaccharide are also within the scope of this disclosure.

An oligosaccharide mixture may comprise two or more oligosaccharides, a first oligosaccharide and a second oligosaccharide which is different than the first oligosaccharide. For instance, the first oligosaccharide may be a xylo-oligosaccharide or a cello-oligosaccharide or a manno-oligosaccharide or other oligosaccharides as provided herein whereas the second oligosaccharide can be a xylo-oligosaccharide or a cello-oligosaccharide or a manno-oligosaccharide or other oligosaccharides not used as the first oligosaccharides. The ratio of a first oligosaccharide to a second oligosaccharide in the mixture may be about 1:1. The ratio of a first oligosaccharide to a second oligosaccharide in the mixture may be about 1:2. The ratio of a first oligosaccharide to a second oligosaccharide in the mixture may be about 1:3. The ratio of a first oligosaccharide to a second oligosaccharide in the mixture may be about 1:4. The ratio of a first oligosaccharide to a second oligosaccharide in the mixture may be about 1:5. The ratio of a first oligosaccharide to a second oligosaccharide in the mixture may be about 1:6. The ratio of a first oligosaccharide to a second oligosaccharide in the mixture may be about 1:7. The ratio of a first oligosaccharide to a second oligosaccharide in the mixture may be about 1:8. The ratio of a first oligosaccharide to a second oligosaccharide in the mixture may be about 1:9.

The ratio of a first oligosaccharide to a second oligosaccharide in the mixture may be about 2:1. The ratio of a first oligosaccharide to a second oligosaccharide in the mixture may be about 2:3. The ratio of a first oligosaccharide to a second oligosaccharide in the mixture may be about 2:5. The ratio of a first oligosaccharide to a second oligosaccharide in the mixture may be about 2:7. The ratio of a first oligosaccharide to a second oligosaccharide in the mixture may be about 2:9. The oligosaccharides may be cello-oligosaccharides, manno-oligosaccharides, xylo-oligosaccharides, xyloglucan-oligosaccharides, mixed-linkage oligosaccharides, chito-oligosaccharides or other oligosaccharides as provided herein wherein the first oligosaccharide is selected to be a different oligosaccharide than the second oligosaccharide.

The ratio of a first oligosaccharide to a second oligosaccharide in the mixture may be about 3:1. The ratio of a first oligosaccharide to a second oligosaccharide in the mixture may be about 3:2. The ratio of a first oligosaccharide to a second oligosaccharide in the mixture may be about 3:4. The ratio of a first oligosaccharide to a second oligosaccharide in the mixture may be about 3:5. The ratio of a first oligosaccharide to a second oligosaccharide in the mixture may be about 3:7. The ratio of a first oligosaccharide to a second oligosaccharide in the mixture may be about 3:8. The oligosaccharides may be cello-oligosaccharides, manno-oligosaccharides, xylo-oligosaccharides, xyloglucan-oligosaccharides, mixed-linkage oligosaccharides, chito-oligosaccharides or other oligosaccharides provided herein wherein the first oligosaccharide is selected to be a different oligosaccharide than the second oligosaccharide.

The ratio of a first oligosaccharide to a second oligosaccharide in an oligosaccharide mixture comprising two or more oligosaccharides may be from 1:9 to 9:1. The ratio of a first oligosaccharide to a second oligosaccharide may be from 1:4 to 4:1. The ratio of a first oligosaccharide to a second oligosaccharide may be from 1:3 to 3:1. The ratio of a first oligosaccharide to a second oligosaccharide may be from 2:3 to 3:2. The oligosaccharides may be cello-oligosaccharides, manno-oligosaccharides, xylo-oligosaccharides, xyloglucan-oligosaccharides, mixed-linkage oligosaccharides, chito-oligosaccharides or other oligosaccharides provided herein wherein the first oligosaccharide is selected to be a different oligosaccharide than the second oligosaccharide.

Oligosaccharide Compositions with Varying Degrees of Polymerization

The concentration of xylo-oligosaccharides with a degree of polymerization of two in a xylo-oligosaccharide mixture may be about 2% to about 80% w/w. The concentration of xylo-oligosaccharides with a degree of polymerization of two may be at least 2%, 4%, 6%, 8%, 10%, 12%, 15%, 18%, 20%, 25%, or 30% w/w. The concentration of xylo-oligosaccharides with a degree of polymerization of two may be higher in some cases, for instance, up to 35%, 40%, 45%, 50%, 55%, 60%, 65%, 70%, 75%, or 80% w/w.

The concentration of xylo-oligosaccharides with a degree of polymerization of three in a xylo-oligosaccharide mixture may be about 2% to about 20% w/w. The concentration of xylo-oligosaccharides with a degree of polymerization of three may be at least 2%, 4%, 6%, 8%, 10%, 12%, 15%, 18%, or 20% w/w.

The concentration of xylo-oligosaccharides with a degree of polymerization of four in a xylo-oligosaccharide mixture may be about 5% to about 20% w/w. The concentration of xylo-oligosaccharides with a degree of polymerization of four may be at least 5%, 8%, 10%, 12%, 15%, 18%, or 20% w/w.

The concentration of xylo-oligosaccharides with a degree of polymerization of five in a xylo-oligosaccharide mixture may be about 5% to about 20% w/w. The concentration of xylo-oligosaccharides with a degree of polymerization of five may be at least 5%, 7%, 8%, 10%, 12%, 15%, 18%, or 20% w/w.

The concentration of xylo-oligosaccharides with a degree of polymerization of six in a xylo-oligosaccharide mixture may be about 5% to about 25% w/w. The concentration of xylo-oligosaccharides with a degree of polymerization of six may be at least 5%, 8%, 10%, 12%, 15%, 18%, 20%, or 25% w/w.

The concentration of xylo-oligosaccharides with a degree of polymerization of seven in a xylo-oligosaccharide mixture may be about 2% to about 20% w/w. The concentration of xylo-oligosaccharides with a degree of polymerization of seven may be at least 2%, 4%, 6%, 8%, 10%, 12%, 15%, 17%, or 20% w/w.

The concentration of xylo-oligosaccharides with a degree of polymerization of eight in a xylo-oligosaccharide mixture may be about 1% to about 15% w/w. The concentration of xylo-oligosaccharides with a degree of polymerization of eight may be at least 1%, 2%, 3%, 4%, 5%, 6%, 7%, 8%, 9%, 10%, or 15% w/w.

The concentration of xylo-oligosaccharides with a degree of polymerization of nine in a xylo-oligosaccharide mixture may be about 2% to about 15% w/w. The concentration of xylo-oligosaccharides with a degree of polymerization of nine may be at least 1%, 2%, 3%, 4%, 5%, 6%, 7%, 8%, 9%, 10%, or 15% w/w.

The concentration of xylo-oligosaccharides with a degree of polymerization of ten in a xylo-oligosaccharide mixture may be about 2% to about 15% w/w. The concentration of xylo-oligosaccharides with a degree of polymerization of ten may be at least 1%, 2%, 3%, 4%, 5%, 6%, 7%, 8%, 9%, 10%, or 15% w/w.

The concentration of xylo-oligosaccharides with a degree of polymerization of eleven in a xylo-oligosaccharide mixture may be about 2% to about 15% w/w. The concentration of xylo-oligosaccharides with a degree of polymerization of eleven may be at least 1%, 2%, 3%, 4%, 5%, 6%, 7%, 8%, 9%, 10%, or 15% w/w.

The concentration of xylo-oligosaccharides with a degree of polymerization of twelve in a xylo-oligosaccharide mixture may be about 2% to about 15% w/w. The concentration of xylo-oligosaccharides with a degree of polymerization of twelve may be at least 1%, 2%, 3%, 4%, 5%, 6%, 7%, 8%, 9%, 10%, or 15% w/w.

The concentration of cello-oligosaccharides with a degree of polymerization of two in a cello-oligosaccharide mixture may be about 2% to about 80% w/w. The concentration of cello-oligosaccharides with a degree of polymerization of two may be at least 2%, 4%, 6%, 8%, 10%, 12%, 15%, 18%, 20%, 25%, or 30% w/w. The concentration of cello-oligosaccharides with a degree of polymerization of two may be higher in some cases, for instance, at least 35%, 40%, 45%, 50%, 55%, 60%, 65%, 70%, 75%, or 80% w/w.

The concentration of cello-oligosaccharides with a degree of polymerization of three in a cello-oligosaccharide mixture may be about 2% to about 20% w/w. The concentration of cello-oligosaccharides with a degree of polymerization of three may be at least 2%, 4%, 6%, 8%, 10%, 12%, 15%, 18%, or 20% w/w.

The concentration of cello-oligosaccharides with a degree of polymerization of four in a cello-oligosaccharide mixture may be about 5% to about 20% w/w. The concentration of cello-oligosaccharides with a degree of polymerization of four may be at least 5%, 8%, 10%, 12%, 15%, 18%, or 20% w/w.

The concentration of cello-oligosaccharides with a degree of polymerization of five in a cello-oligosaccharide mixture may be about 5% to about 20% w/w. The concentration of cello-oligosaccharides with a degree of polymerization of five may be at least 5%, 7%, 8%, 10%, 12%, 15%, 18%, or 20% w/w.

The concentration of cello-oligosaccharides with a degree of polymerization of six in a cello-oligosaccharide mixture may be about 5% to about 25% w/w. The concentration of cello-oligosaccharides with a degree of polymerization of six may be at least 5%, 8%, 10%, 12%, 15%, 18%, 20%, or 25% w/w.

The concentration of manno-oligosaccharides with a degree of polymerization of two in a manno-oligosaccharide mixture may be about 2% to about 30% w/w. The concentration of manno-oligosaccharides with a degree of polymerization of two may be at least 2%, 4%, 6%, 8%, 10%, 12%, 15%, 18%, 20%, 25%, or 30% w/w.

The concentration of manno-oligosaccharides with a degree of polymerization of three in a manno-oligosaccharide mixture may be about 2% to about 20% w/w. The concentration of manno-oligosaccharides with a degree of polymerization of three may be at least 2%, 4%, 6%, 8%, 10%, 12%, 15%, 18%, or 20% w/w.

The concentration of manno-oligosaccharides with a degree of polymerization of four in a manno-oligosaccharide mixture may be about 5% to about 20% w/w. The concentration of manno-oligosaccharides with a degree of polymerization of four may be at least 5%, 8%, 10%, 12%, 15%, 18%, or 20% w/w.

The concentration of manno-oligosaccharides with a degree of polymerization of five in a manno-oligosaccharide mixture may be about 5% to about 20% w/w. The concentration of manno-oligosaccharides with a degree of polymerization of five may be at least 5%, 7%, 8%, 10%, 12%, 15%, 18%, or 20% w/w.

The concentration of manno-oligosaccharides with a degree of polymerization of six in a manno-oligosaccharide mixture may be about 5% to about 25% w/w. The concentration of manno-oligosaccharides with a degree of polymerization of six may be at least 5%, 8%, 10%, 12%, 15%, 18%, 20%, or 25% w/w.

The concentration of manno-oligosaccharides with a degree of polymerization of seven in a manno-oligosaccharide mixture may be about 2% to about 20% w/w. The concentration of manno-oligosaccharides with a degree of polymerization of seven may be at least 2%, 4%, 6%, 8%, 10%, 12%, 15%, 17%, or 20% w/w.

The concentration of manno-oligosaccharides with a degree of polymerization of eight in a manno-oligosaccharide mixture may be about 1% to about 15% w/w. The concentration of manno-oligosaccharides with a degree of polymerization of eight may be at least 1%, 2%, 3%, 4%, 5%, 6%, 7%, 8%, 9%, 10%, or 15% w/w.

The concentration of manno-oligosaccharides with a degree of polymerization of nine in a manno-oligosaccharide mixture may be about 2% to about 15% w/w. The concentration of manno-oligosaccharides with a degree of polymerization of nine may be at least 1%, 2%, 3%, 4%, 5%, 6%, 7%, 8%, 9%, 10%, or 15% w/w.

The concentration of manno-oligosaccharides with a degree of polymerization of ten in a manno-oligosaccharide mixture may be about 2% to about 15% w/w. The concentration of manno-oligosaccharides with a degree of polymerization of ten may be at least 1%, 2%, 3%, 4%, 5%, 6%, 7%, 8%, 9%, 10%, or 15% w/w.

The concentration of manno-oligosaccharides with a degree of polymerization of eleven in a manno-oligosaccharide mixture may be about 2% to about 15% w/w. The concentration of manno-oligosaccharides with a degree of polymerization of eleven may be at least 1%, 2%, 3%, 4%, 5%, 6%, 7%, 8%, 9%, 10%, or 15% w/w.

The concentration of manno-oligosaccharides with a degree of polymerization of twelve in a manno-oligosaccharide mixture may be about 2% to about 15% w/w. The concentration of manno-oligosaccharides with a degree of polymerization of twelve may be at least 1%, 2%, 3%, 4%, 5%, 6%, 7%, 8%, 9%, 10%, or 15% w/w.

The concentration of xyloglucan-oligosaccharides with a degree of polymerization of four in a xyloglucan-oligosaccharide mixture may be about 5% to about 20% w/w. The concentration of xyloglucan-oligosaccharides with a degree of polymerization of four may be at least 5%, 8%, 10%, 12%, 15%, 18%, or 20% w/w.

The concentration of xyloglucan-oligosaccharides with a degree of polymerization of five in a xyloglucan-oligosaccharide mixture may be about 5% to about 20% w/w. The concentration of xyloglucan-oligosaccharides with a degree of polymerization of five may be at least 5%, 7%, 8%, 10%, 12%, 15%, 18%, or 20% w/w.

The concentration of xyloglucan-oligosaccharides with a degree of polymerization of six in a xyloglucan-oligosaccharide mixture may be about 5% to about 25% w/w. The concentration of xyloglucan-oligosaccharides with a degree of polymerization of six may be at least 5%, 8%, 10%, 12%, 15%, 18%, 20%, or 25% w/w.

The concentration of xyloglucan-oligosaccharides with a degree of polymerization of seven in a xyloglucan-oligosaccharide mixture may be about 2% to about 20% w/w. The concentration of xyloglucan-oligosaccharides with a degree of polymerization of seven may be at least 2%, 4%, 6%, 8%, 10%, 12%, 15%, 17%, or 20% w/w.

The concentration of xyloglucan-oligosaccharides with a degree of polymerization of eight in a xyloglucan-oligosaccharide mixture may be about 1% to about 15% w/w. The concentration of xyloglucan-oligosaccharides with a degree of polymerization of eight may be at least 1%, 2%, 3%, 4%, 5%, 6%, 7%, 8%, 9%, 10%, or 15% w/w.

The concentration of xyloglucan-oligosaccharides with a degree of polymerization of nine in a xyloglucan-oligosaccharide mixture may be about 2% to about 15% w/w. The concentration of xyloglucan-oligosaccharides with a degree of polymerization of nine may be at least 1%, 2%, 3%, 4%, 5%, 6%, 7%, 8%, 9%, 10%, or 15% w/w.

The concentration of xyloglucan-oligosaccharides with a degree of polymerization of ten in a xyloglucan-oligosaccharide mixture may be about 2% to about 15% w/w. The concentration of xyloglucan-oligosaccharides with a degree of polymerization of ten may be at least 1%, 2%, 3%, 4%, 5%, 6%, 7%, 8%, 9%, 10%, or 15% w/w.

The concentration of mixed-linkage glucan-oligosaccharides with a degree of polymerization of two in a mixed-linkage glucan-oligosaccharide mixture may be about 2% to about 30% w/w. The concentration of mixed-linkage glucan-oligosaccharides with a degree of polymerization of two may be at least 2%, 4%, 6%, 8%, 10%, 12%, 15%, 18%, 20%, 25%, or 30% w/w.

The concentration of mixed-linkage glucan-oligosaccharides with a degree of polymerization of three in a mixed-linkage glucan-oligosaccharide mixture may be about 2% to about 20% w/w. The concentration of mixed-linkage glucan-oligosaccharides with a degree of polymerization of three may be at least 2%, 4%, 6%, 8%, 10%, 12%, 15%, 18%, or 20% w/w.

The concentration of mixed-linkage glucan-oligosaccharides with a degree of polymerization of four in a mixed-linkage glucan-oligosaccharide mixture may be about 5% to about 20% w/w. The concentration of mixed-linkage glucan-oligosaccharides with a degree of polymerization of four may be at least 5%, 8%, 10%, 12%, 15%, 18%, or 20% w/w.

The concentration of mixed-linkage glucan-oligosaccharides with a degree of polymerization of five in a mixed-linkage glucan-oligosaccharide mixture may be about 5% to about 20% w/w. The concentration of mixed-linkage glucan-oligosaccharides with a degree of polymerization of five may be at least 5%, 7%, 8%, 10%, 12%, 15%, 18%, or 20% w/w.

The concentration of chito-oligosaccharides with a degree of polymerization of two in a chito-oligosaccharide mixture may be about 2% to about 30% w/w. The concentration of chito-oligosaccharides with a degree of polymerization of two may be at least 2%, 4%, 6%, 8%, 10%, 12%, 15%, 18%, 20%, 25%, or 30% w/w.

The concentration of chito-oligosaccharides with a degree of polymerization of three in a chito-oligosaccharide mixture may be about 2% to about 20% w/w. The concentration of chito-oligosaccharides with a degree of polymerization of three may be at least 2%, 4%, 6%, 8%, 10%, 12%, 15%, 18%, or 20% w/w.

The concentration of chito-oligosaccharides with a degree of polymerization of four in a chito-oligosaccharide mixture may be about 5% to about 20% w/w. The concentration of chito-oligosaccharides with a degree of polymerization of four may be at least 5%, 8%, 10%, 12%, 15%, 18%, or 20% w/w.

The concentration of chito-oligosaccharides with a degree of polymerization of five in a chito-oligosaccharide mixture may be about 5% to about 20% w/w. The concentration of chito-oligosaccharides with a degree of polymerization of five may be at least 5%, 7%, 8%, 10%, 12%, 15%, 18%, or 20% w/w.

The concentration of chito-oligosaccharides with a degree of polymerization of six in a chito-oligosaccharide mixture may be about 5% to about 25% w/w. The concentration of chito-oligosaccharides with a degree of polymerization of six may be at least 5%, 8%, 10%, 12%, 15%, 18%, 20%, or 25% w/w.

The concentration of chito-oligosaccharides with a degree of polymerization of seven in a chito-oligosaccharide mixture may be about 2% to about 20% w/w. The concentration of chito-oligosaccharides with a degree of polymerization of seven may be at least 2%, 4%, 6%, 8%, 10%, 12%, 15%, 17%, or 20% w/w.

The concentration of chito-oligosaccharides with a degree of polymerization of eight in a chito-oligosaccharide mixture may be about 1% to about 15% w/w. The concentration of chito-oligosaccharides with a degree of polymerization of eight may be at least 1%, 2%, 3%, 4%, 5%, 6%, 7%, 8%, 9%, 10%, or 15% w/w.

The concentration of chito-oligosaccharides with a degree of polymerization of nine in a chito-oligosaccharide mixture may be about 2% to about 15% w/w. The concentration of chito-oligosaccharides with a degree of polymerization of nine may be at least 1%, 2%, 3%, 4%, 5%, 6%, 7%, 8%, 9%, 10%, or 15% w/w.

The concentration of chito-oligosaccharides with a degree of polymerization of ten in a chito-oligosaccharide mixture may be about 2% to about 15% w/w. The concentration of chito-oligosaccharides with a degree of polymerization of ten may be at least 1%, 2%, 3%, 4%, 5%, 6%, 7%, 8%, 9%, 10% or 15% w/w.

The concentration of chito-oligosaccharides with a degree of polymerization of eleven in a chito-oligosaccharide mixture may be about 2% to about 15% w/w. The concentration of chito-oligosaccharides with a degree of polymerization of eleven may be at least 1%, 2%, 3%, 4%, 5%, 6%, 7%, 8%, 9%, 10%, or 15% w/w.

The concentration of chito-oligosaccharides with a degree of polymerization of twelve in a chito-oligosaccharide mixture may be about 2% to about 15% w/w. The concentration of chito-oligosaccharides with a degree of polymerization of twelve may be at least 1%, 2%, 3%, 4%, 5%, 6%, 7%, 8%, 9%, 10%, or 15% w/w.

Compositions with Combinations of Polysaccharides and Oligosaccharides

A composition may comprise a combination of polysaccharides and oligosaccharides. The source of the polysaccharides in such compositions may contain cellulose, such as plant biomass, for example the undigested component of partially digested plant biomass, such as the undigested plant biomass from the same reaction as that which produced the oligosaccharides. The polysaccharides in the undigested biomass may comprise lignin, polyphenol, cellulose, lignocellulose, or any other suitable polysaccharides as described herein. Addition of polysaccharides to oligosaccharide mixtures can be done to improve the gastrointestinal tolerance of the oligosaccharide mixtures. Oligosaccharide consumption can cause gastrointestinal distress, including diarrhea, discomfort, and bloating. The compositions described herein may have an improved gastrointestinal tolerance such as, less or no discomfort, bloating, diarrhea or gastrointestinal distress as compared to a saccharide composition available commercially or a saccharide composition comprising primarily monosaccharides and/or disaccharides.

The concentration of undigested biomass in a composition may be 1% to 50% w/w. The concentration of undigested biomass in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of undigested biomass in a composition may be 1%, 5%, 10%, 15%, 20%, 25%, 30%, 35%, 40%, 45%, or 50% w/w. The concentration of undigested biomass in a composition may be at least 1%, 5%, 10%, 15%, 20%, 25%, 30%, 35%, 40%, or 45% w/w. The concentration of undigested biomass in a composition may be at most 5%, 10%, 15%, 20%, 25%, 30%, 35%, 40%, 45%, or 50% w/w.

The concentration of xylo-oligosaccharides in a composition may be 1% to 50% w/w. The concentration of xylo-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of xylo-oligosaccharides in a composition may be 1%, 5%, 10%, 15%, 20%, 25%, 30%, 35%, 40%, 45%, or 50% w/w. The concentration of xylo-oligosaccharides in a composition may be at least 1%, 5%, 10%, 15%, 20%, 25%, 30%, 35%, 40%, or 45% w/w. The concentration of xylo-oligosaccharides in a composition may be at most 5%, 10%, 15%, 20%, 25%, 30%, 35%, 40%, 45%, or 50% w/w.

The concentration of cello-oligosaccharides in a composition may be 1% to 50% w/w. The concentration of cello-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of cello-oligosaccharides in a composition may be 1%, 5%, 10%, 15%, 20%, 25%, 30%, 35%, 40%, 45%, or 50% w/w. The concentration of cello-oligosaccharides in a composition may be at least 1%, 5%, 10%, 15%, 20%, 25%, 30%, 35%, 40%, or 45% w/w. The concentration of cello-oligosaccharides in a composition may be at most 5%, 10%, 15%, 20%, 25%, 30%, 35%, 40%, 45%, or 50% w/w.

The concentration of manno-oligosaccharides in a composition may be 1% to 50% w/w. The concentration of manno-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of manno-oligosaccharides in a composition may be 1%, 5%, 10%, 15%, 20%, 25%, 30%, 35%, 40%, 45%, or 50% w/w. The concentration of manno-oligosaccharides in a composition may be at least 1%, 5%, 10%, 15%, 20%, 25%, 30%, 35%, 40%, or 45% w/w. The concentration of manno-oligosaccharides in a composition may be at most 5%, 10%, 15%, 20%, 25%, 30%, 35%, 40%, 45%, or 50% w/w.

The concentration of chito-oligosaccharides in a composition may be 1% to 50% w/w. The concentration of chito-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of chito-oligosaccharides in a composition may be 1%, 5%, 10%, 15%, 20%, 25%, 30%, 35%, 40%, 45%, or 50% w/w. The concentration of chito-oligosaccharides in a composition may be at least 1%, 5%, 10%, 15%, 20%, 25%, 30%, 35%, 40%, or 45% w/w. The concentration of chito-oligosaccharides in a composition may be at most 5%, 10%, 15%, 20%, 25%, 30%, 35%, 40%, 45%, or 50% w/w.

The concentration of xyloglucan-oligosaccharides in a composition may be 1% to 50% w/w. The concentration of xyloglucan-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of xyloglucan-oligosaccharides in a composition may be 1%, 5%, 10%, 15%, 20%, 25%, 30%, 35%, 40%, 45%, or 50% w/w. The concentration of xyloglucan-oligosaccharides in a composition may be at least 1%, 5%, 10%, 15%, 20%, 25%, 30%, 35%, 40%, or 45% w/w. The concentration of xyloglucan-oligosaccharides in a composition may be at most 5%, 10%, 15%, 20%, 25%, 30%, 35%, 40%, 45%, or 50% w/w.

The concentration of mixed-linkage glucan-oligosaccharides in a composition may be 1% to 50% w/w. The concentration of mixed-linkage glucan-oligosaccharides in a composition may be 1% to 5%, 1% to 10%, 1% to 15%, 1% to 20%, 1% to 25%, 1% to 30%, 1% to 35%, 1% to 40%, 1% to 45%, 1% to 50%, 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 15% to 20%, 15% to 25%, 15% to 30%, 15% to 35%, 15% to 40%, 15% to 45%, 15% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, or 45% to 50% w/w. The concentration of mixed-linkage glucan-oligosaccharides in a composition may be 1%, 5%, 10%, 15%, 20%, 25%, 30%, 35%, 40%, 45%, or 50% w/w. The concentration of mixed-linkage glucan-oligosaccharides in a composition may be at least 1%, 5%, 10%, 15%, 20%, 25%, 30%, 35%, 40%, or 45% w/w. The concentration of mixed-linkage glucan-oligosaccharides in a composition may be at most 5%, 10%, 15%, 20%, 25%, 30%, 35%, 40%, 45%, or 50% w/w.

A composition may comprise polysaccharides and one or more oligosaccharides. The composition may comprise a polysaccharide and one type of oligosaccharide. The composition may comprise a polysaccharide and two forms of oligosaccharides. The composition may comprise a polysaccharide and three forms of oligosaccharides. The composition may comprise a polysaccharide and four forms of oligosaccharides. The composition may comprise a polysaccharide and five forms of oligosaccharides. The oligosaccharides may be xylo-oligosaccharides, cello-oligosaccharides, manno-oligosaccharides, xyloglucan-oligosaccharides, chito-oligosaccharides, or any other suitable oligosaccharides described herein.

The composition may comprise about 5% to 50% polysaccharides w/w, such as in the type of undigested biomass, and about 5% to about 95% oligosaccharides w/w. The composition of polysaccharides may be at least about 5%, 10%, 15%, 20%, 25%, 30%, 35%, 40%, or 50% w/w w/w. Oligosaccharides in such mixtures may be present at greater than 5%, 10%, 15%, 20%, 25%, 30%, 35%, 40%, 45%, 50%, 55%, 60%, 65%, 70%, 75%, 80%, 85%, 90%, or 95% w/w. The oligosaccharides may be a mixture of one or more oligosaccharides. For instance, a composition may comprise 5% undigested biomass and 50% oligosaccharide mixture w/w as described elsewhere herein.

The composition may comprise about 5% polysaccharides w/w, such as in the type of undigested biomass, and about 5% to about 95% oligosaccharides w/w. Oligosaccharides in such mixtures may be present at greater than 5%, 10%, 15%, 20%, 25%, 30%, 35%, 40%, 45%, 50%, 55%, 60%, 65%, 70%, 75%, 80%, 85%, 90% or 95% w/w. The oligosaccharides may be a mixture of one or more oligosaccharides. For instance, a composition may comprise 5% undigested biomass and 50% oligosaccharide mixture w/w as described elsewhere herein.

The composition may comprise about 7% polysaccharides w/w, such as in the type of undigested biomass and about 5% to about 93% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85%, 90% or 93% w/w of such mixtures. The oligosaccharides may be a mixture of one or more oligosaccharides. For instance, a composition may comprise 7% undigested biomass and 50% oligosaccharide mixture w/w as described elsewhere herein.

The composition may comprise about 10% polysaccharides w/w, such as in the type of undigested biomass and about 5% to about 90% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85% or 90% w/w of such mixtures. The oligosaccharides may be a mixture of one or more oligosaccharides. For instance, a composition may comprise 10% undigested biomass and 50% oligosaccharide mixture w/w as described elsewhere herein.

The composition may comprise about 12% polysaccharides w/w, such as in the type of undigested biomass and about 5% to about 95% oligosaccharides w/w. Oligosaccharides may form at least 5%, 10%, 15%, 20%, 25%, 30%, 35%, 40%, 45%, 50%, 55%, 60%, 65%, 70%, 75%, 80%, 85% or 88% w/w of such mixtures. The oligosaccharides may be a mixture of one or more oligosaccharides. For instance, a composition may comprise 12% undigested biomass and 50% oligosaccharide mixture w/w as described elsewhere herein.

The composition may comprise about 15% polysaccharides w/w, such as in the type of undigested biomass and about 5% to about 85% oligosaccharides w/w. Oligosaccharides may form at least 5%, 10%, 15%, 20%, 25%, 30%, 35%, 40%, 45%, 50%, 55%, 60%, 65%, 70%, 75%, 80% or 85% w/w of such mixtures. The oligosaccharides may be a mixture of one or more oligosaccharides. For instance, a composition may comprise 15% undigested biomass and 50% oligosaccharide mixture w/w as described elsewhere herein.

The composition may comprise about 20% polysaccharides w/w, such as in the type of undigested biomass and about 5% to about 80% oligosaccharides w/w. Oligosaccharides may form at least 5%, 10%, 15%, 20%, 25%, 30%, 35%, 40%, 45%, 50%, 55%, 60%, 65%, 70%, 75% or 80% w/w of such mixtures. The oligosaccharides may be a mixture of one or more oligosaccharides. For instance, a composition may comprise 20% undigested biomass and 50% oligosaccharide mixture w/w as described elsewhere herein.

The composition may comprise about 25% polysaccharides w/w, such as in the type of undigested biomass and about 5% to about 75% oligosaccharides w/w. Oligosaccharides may form at least 5%, 10%, 15%, 20%, 25%, 30%, 35%, 40%, 45%, 50%, 55%, 60%, 65%, 70% or 75% w/w of such mixtures. The oligosaccharides may be a mixture of one or more oligosaccharides. For instance, a composition may comprise 25% undigested biomass and 50% oligosaccharide mixture w/w as described elsewhere herein.

The composition may comprise about 30% polysaccharides w/w, such as in the type of undigested biomass and about 5% to about 70% oligosaccharides w/w. Oligosaccharides may form at least 5%, 10%, 15%, 20%, 25%, 30%, 35%, 40%, 45%, 50%, 55%, 60%, 65% or 70% w/w of such mixtures. The oligosaccharides may be a mixture of one or more oligosaccharides. For instance, a composition may comprise 30% undigested biomass and 50% oligosaccharide mixture w/w as described elsewhere herein.

The composition may comprise about 40% polysaccharides w/w, such as in the type of undigested biomass and about 5% to about 60% oligosaccharides w/w. Oligosaccharides may form at least 5%, 10%, 15%, 20%, 25%, 30%, 35%, 40%, 45%, 50%, 55% or 60% w/w of such mixtures. The oligosaccharides may be a mixture of one or more oligosaccharides. For instance, a composition may comprise 40% undigested biomass and 50% oligosaccharide mixture w/w as described elsewhere herein.

The composition may comprise about 50% polysaccharides w/w, such as in the type of undigested biomass and about 5% to about 50% oligosaccharides w/w. Oligosaccharides may form at least 5%, 10%, 15%, 20%, 25%, 30%, 35%, 40%, 45% or 50% w/w of such mixtures. The oligosaccharides may be a mixture of one or more oligosaccharides. For instance, a composition may comprise 50% undigested biomass and 50% oligosaccharide mixture w/w as described elsewhere herein.

Use of Compositions as Ingredients

In some embodiments, the composition is an ingredient. As used herein, "ingredient" is any composition suitable for incorporation into a foodstuff, cosmetic, or nutraceutical product, which may include those which are used directly as the product itself.

In some embodiments, the ingredient comprises at least 50%, 60%, 70%, 80%, 90%, 95%, 99%, 99.5% by dry weight of saccharide present. The ingredient may consist essentially of saccharides. As used herein, "consist essentially of" means that the material (for instance the ingredient) has less than 0.5% by dry weight, such as 0.3% by dry weight, for instance 0.1% by dry weight, of other substances.

The ingredient may comprise an oligosaccharide mixture as described elsewhere herein. The ingredient may comprise at least two of the oligosaccharides. For instance, it may comprise three of the oligosaccharides. It may comprise four oligosaccharides. It may comprise five oligosaccharides. It may comprise six oligosaccharides.

In some embodiments, the ingredient comprises cello-oligosaccharides, for instance cello-oligosaccharides in combination with the xylo-oligosaccharides. An alternative ingredient may comprise cello-oligosaccharides in combination with manno-oligosaccharides.

Ingredients may be used to prepare finished products. The ingredient may also be treated in some physical or chemical way before or during incorporation into a foodstuff, cosmetic, or nutraceutical. It may be directly incorporated into a product, or it may be incorporated into, for example, a dough, cake mixture, chocolate mixture, or other foodstuff precursor; a cosmetic base composition; or a nutraceutical, and be optionally cooked or otherwise treated in a way which may cause chemical modification, a change of texture a change of colour, or other modification.

A foodstuff, cosmetic, or nutraceutical may be produced from an ingredient described herein. For example, in the food industry the saccharide formulations produced by the current method may be used as sweeteners, bulking agents, added dietary fibre, or humectants. The ingredient may be used as a sugar substitute. The ingredient may be incorporated into cakes, bread, or other baked goods, or into chocolate or other confectionery such as toffee, fudge, meringue, jam, jelly or caramel; or drinks, for example, to provide favourable taste or colour characteristics or to increase dietary fibre content. Or they may be incorporated into animal feed, for example either as an isolated ingredient or by utilising the enzymatic reaction mixture directly as feed.

In the cosmetics industry, saccharides can be useful as ingredients, as they may improve texture and moisture retention, act as UV-absorbing molecules, maintain a gel or cream structure, and/or serve as bulking agents. The compositions described herein can be incorporated into nutraceutical compositions, as the dietary fibre they provide has been shown to encourage digestive health, well-regulated gut flora, and other benefits to wellbeing. In this context, they may also function as an ingredient in a probiotic drink or other prebiotic or probiotic formulation.

Compositions or ingredients as described herein may be used to alter one or more properties of the finished product. Such properties include, but are not limited to, sweetness, texture, mouthfeel, binding, glazing, smoothness, moistness, viscosity, color, hygroscopicity, flavor, bulking, water-retention, caramelization, surface texture, crystallization, structural properties and dissolution.

In some cases, the compositions and/or ingredients described herein may provide a property to a finished product which is comparable to or better than the same property as provided by a saccharide mixture comprising primarily monosaccharides and/or disaccharides. The control composition may be a saccharide used commonly in consumables, for instance, a monosaccharide composition such as glucose, fructose, etc, a disaccharide composition such as sucrose or an artificial sugar composition. The term "comparable" as used herein may mean that the two compositions may be up to 100%, up to 95%, up to 90%, up to 80% identical. For instance, comparable can mean that the composition is up to 90% identical to the control composition.

In some cases, the compositions described herein may be used as sweetener compositions. Sweetener compositions may be used by themselves or as an ingredient in a finished product. The compositions described herein may provide about the same level of sweetness or greater sweetness than an identical amount of a control composition wherein the control composition comprises primarily monosaccharides and/or disaccharides. The compositions described herein may be used to replace the control composition as the sweetener in a finished product. In some cases, the sweetness of a composition may be 5%, 10%, 15%, 20%, 30%, 40%, 50%, 70%, 80%, 90% or 100% more than an identical amount of the control composition.

The compositions described herein may provide a comparable flavor profile or better flavor profile than an identical amount of a control composition wherein the control composition comprises primarily monosaccharides and/or disaccharides. The compositions described herein may be used to replace the control composition as a flavor enhancer in a finished product. In some cases, the flavor of a composition may be 5%, 10%, 15%, 20%, 30%, 40%, 50%, 70%, 80%, 90% or 100% more than an identical amount of the control composition.

The compositions described herein may provide a comparable texture profile or better texture profile than an identical amount of a control composition wherein the control composition comprises primarily monosaccharides and/or disaccharides. The compositions described herein may be used to replace the control composition as a texture enhancer in a finished product.

The compositions described herein may provide a comparable binding profile or better binding profile than an identical amount of a control composition wherein the control composition comprises primarily monosaccharides and/or disaccharides. The compositions described herein may be used to replace the control composition as a binding enhancer in a finished product.

The compositions described herein may provide a comparable glazing profile or better glazing profile than an identical amount of a control composition wherein the control composition comprises primarily monosaccharides and/or disaccharides. The compositions described herein may be used to replace the control composition as a glazing enhancer in a finished product.

The compositions described herein may provide a comparable moistness or better moistness than an identical amount of a control composition wherein the control composition comprises primarily monosaccharides and/or disaccharides. The compositions described herein may be used to replace the control composition to provide moistness in a finished product.

The compositions described herein may provide a comparable color profile or better color profile than an identical amount of a control composition wherein the control composition comprises primarily monosaccharides and/or disaccharides. The compositions described herein may be used to replace the control composition as a color enhancer in a finished product.

The compositions described herein may provide a comparable dissolution profile or better dissolution profile than an identical amount of a control composition wherein the control composition comprises primarily monosaccharides and/or disaccharides. The compositions described herein may be used to replace the control composition as a dissolution enhancer in a finished product. In some cases, the dissolution of a composition may be 5%, 10%, 15%, 20%, 30%, 40%, 50%, 70%, 80%, 90% or 100% more than an identical amount of the control composition.

The compositions described herein may provide a comparable mouthfeel or better mouthfeel than an identical amount of a control composition wherein the control composition comprises primarily monosaccharides and/or disaccharides.

The compositions described herein may provide a comparable viscosity or better viscosity than an identical amount of a control composition wherein the control composition comprises primarily monosaccharides and/or disaccharides.

The compositions described herein may provide a comparable hygroscopicity or better hygroscopicity than an identical amount of a control composition wherein the control composition comprises primarily monosaccharides and/or disaccharides. In some cases, the hygroscopicity of a composition may be 5%, 10%, 15%, 20%, 30%, 40%, 50%, 70%, 80%, 90% or 100% more than an identical amount of the control composition.

The compositions described herein may provide a comparable water-retention or better water-retention than an identical amount of a control composition wherein the control composition comprises primarily monosaccharides and/or disaccharides. In some cases, the water-retention of a composition may be 5%, 10%, 15%, 20%, 30%, 40%, 50%, 70%, 80%, 90% or 100% more than an identical amount of the control composition.

The compositions described herein may provide a lower calorie composition than an identical amount of a control composition wherein the control composition comprises primarily monosaccharides and/or disaccharides. In some cases, the calorie count of a composition may be 5%, 10%, 15%, 20%, 30%, 40%, 50%, 70%, 80%, 90% or 100% less than an identical amount of the control composition.

The compositions described herein may provide a lower glycemic index than an identical amount of a control composition wherein the control composition comprises primarily monosaccharides and/or disaccharides. In some cases, the glycemic index of a composition may be 5%, 10%, 15%, 20%, 30%, 40%, 50%, 70%, 80%, 90% or 100% less than an identical amount of the control composition.

The compositions described herein may provide a comparable bulking or better bulking than an identical amount of a control composition wherein the control composition comprises primarily monosaccharides and/or disaccharides.

The compositions described herein may provide a comparable caramelization or better caramelization than an identical amount of a control composition wherein the control composition comprises primarily monosaccharides and/or disaccharides.

The compositions described herein may provide a comparable surface texture or better surface texture than an identical amount of a control composition wherein the control composition comprises primarily monosaccharides and/or disaccharides.

The compositions described herein may provide a comparable crystallization or better crystallization than an identical amount of a control composition wherein the control composition comprises primarily monosaccharides and/or disaccharides.

The compositions described herein may provide comparable structural properties as an identical amount of a control composition wherein the control composition comprises primarily monosaccharides and/or disaccharides.

The compositions described herein may provide less aftertaste compared to an identical amount of a control composition wherein the control composition comprises primarily monosaccharides and/or disaccharides.

Different compositions of oligosaccharides may have improved dissolution profiles, hygroscopicity profiles, and taste profiles compared to the oligosaccharides used alone.

The compositions or ingredients as described herein may be used to increase the fibre content of a finished product such as a foodstuff or a nutraceutical. The compositions may provide a higher level of fibre in the finished product as compared to an identical amount of a control composition wherein the control composition comprises primarily monosaccharides and/or disaccharides. In some cases, the compositions may improve the fibre content of the finished product without negatively affecting any other properties such as taste, sweetness, mouthfeel, texture, binding, or any other properties described herein. In some cases, the fibre content of a composition may be 5%, 10%, 15%, 20%, 30%, 40%, 50%, 70%, 80%, 90% or 100% more than an identical amount of the control composition.

Ingredients may be used to alter the properties of a finished product such as foodstuff or nutraceutical or cosmetic. In order to alter the properties of the finished products, the finished products may additionally comprise a polysaccharide, preferably a cellulosic polysaccharide, such as cellulose, or a polysaccharide derivative, preferably a cellulose derivative, such as carboxymethylcellulose, or a polysaccharide aggregate, preferably a portion of lignocellulosic biomass. Suitably, the finished products can comprise from greater than 0% to 40% by dry weight of polysaccharide, polysaccharide derivative, or polysaccharide aggregate, preferably from greater than 1% to 30% by dry weight of polysaccharide, polysaccharide derivative, or polysaccharide aggregate, preferably from greater than 5% to 25% by dry weight of polysaccharide, polysaccharide derivative, or polysaccharide aggregate, preferably from greater than 10% to 20% by dry weight of polysaccharide, polysaccharide derivative, or polysaccharide aggregate.

The concentration of a composition comprising polysaccharides and a mixture of oligosaccharides in a finished product may be anywhere from 0.1% to 40% w/w. The concentration of a composition comprising polysaccharides and a mixture of oligosaccharides in a finished product may be about 0.1% to about 0.5%, about 0.1% to about 1%, about 0.1% to about 5%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.5% to about 1%, about 0.5% to about 5%, about 0.5% to about 10%, about 0.5% to about 15%, about 0.5% to about 20%, about 0.5% to about 25%, about 0.5% to about 30%, about 0.5% to about 35%, about 0.5% to about 40%, about 1% to about 5%, about 1% to about 10%, about 1% to about 15%, about 1% to about 20%, about 1% to about 25%, about 1% to about 30%, about 1% to about 35%, about 1% to about 40%, about 5% to about 10%, about 5% to about 15%, about 5% to about 20%, about 5% to about 25%, about 5% to about 30%, about 5% to about 35%, about 5% to about 40%, about 10% to about 15%, about 10% to about 20%, about 10% to about 25%, about 10% to about 30%, about 10% to about 35%, about 10% to about 40%, about 15% to about 20%, about 15% to about 25%, about 15% to about 30%, about 15% to about 35%, about 15% to about 40%, about 20% to about 25%, about 20% to about 30%, about 20% to about 35%, about 20% to about 40%, about 25% to about 30%, about 25% to about 35%, about 25% to about 40%, about 30% to about 35%, about 30% to about 40%, or about 35% to about 40% w/w. The concentration of a composition comprising polysaccharides and a mixture of oligosaccharides in a finished product may be about 0.1%, about 0.5%, about 1%, about 5%, about 10%, about 15%, about 20%, about 25%, about 30%, about 35%, or about 40% w/w. The concentration of a composition comprising polysaccharides and a mixture of oligosaccharides in a finished product may be at least 0.1%, 0.5%, 1%, 5%, 10%, 15%, 20%, 25%, 30%, or 35% w/w. The concentration of a composition comprising polysaccharides and a mixture of oligosaccharides in a finished product may be at most 0.5%, 1%, 5%, 10%, 15%, 20%, 25%, 30%, 35%, or 40% w/w.

Enzymatic Reactions

One step of the method of forming or manufacturing the composition??? may be an enzymatic reaction, in which one or more enzymes are placed in a suitable reaction vessel together with one or more feedstocks, which may be soluble or insoluble in water, and a suitable solvent.

A variety of enzymes may be suitable for use in the enzymatic reaction. Any enzyme which produces oligosaccharides when acting on a polysaccharide-containing feedstock may be appropriate, and it is within the ability of the skilled person to select suitable enzymes. Preferably, the enzymatic reaction comprises a cellulase, an endo-glucanase, a cellobiohydrolase, a lytic polysaccharide monooxygenase (LPMO), a lichenase, a xyloglucan endoglucanase (XEG), a mannanase, a chitinase, and/or a xylanase.

More preferably, the enzymatic reaction comprises a cellulolytic preparation from a species, such as *Trichoderma reesei*, which may be purified and/or pre-treated and/or may be supplemented with one or more additional enzymes, for example, adding a beta-glucanase (SEQ ID NO: 14), a beta-xylanase (SEQ ID NO: 16) and a cellobiohydrolase, or a beta-glucanase, a beta-xylanase, an LPMO and a cellobiohydrolase, or an LPMO and a xylanase, or an LPMO, a xylanase, and a lichenase. Each enzyme may be provided to the enzymatic reaction as a purified enzyme, a semi-purified mixture derived from some natural source or lab-grown culture, in the form of a microbial strain engineered to produce the enzyme, or in any other manner. Fusions of these enzymes, either with other enzymes or with non-enzymatic modules such as carbohydrate-binding modules (CBMs), are also envisaged within each respective term, for example, an LPMO fused to a CBM, a xylanase fused to a CBM, or a xylanase fused to an LPMO.

As used herein, "cellulase" refers to an enzyme that has, or a group of enzymes that collectively have, hydrolytic activity against cellulose, for example, an enzyme preparation containing endo-1,4-beta-glucanase, cellobiohydrolase, and/or beta-glucosidase activities. Such enzymes may be able to cleave glycosidic bonds in one or more forms of cellulose, including cellulose found in plant biomass. In doing so, they can produce products including glucose and cello-oligosaccharides.

As used herein, "cellobiohydrolase" refers to an enzyme that has hydrolytic activity against cellulose and produces mainly cellobiose as a product. Cellobiose is a disaccharide and is a cello-oligosaccharide. Such enzymes are able to cleave glycosidic bonds in one or more forms of cellulose, including cellulose found in plant biomass. Preferable cellobiohydrolases are from the GH6 and GH7 enzyme families, such as cellobiohydrolase 12 and 13 from *Aspergillus niger* (SEQ ID NO:20 and 21) more preferably, Cel6A or Cel7A enzymes derived from *Trichoderma reesei* (SEQ ID NOs:10 and 11).

As used herein, "beta-glucosidase" refers to an enzyme that has hydrolytic activity against cellulose and produces mainly glucose as a product. Such enzymes are able to cleave glycosidic bonds in one or more forms of cellulose, including cellulose found in plant biomass. Preferred beta-glucosidases include GH3 beta-glucosidases from *Trichoderma reesei* (SEQ ID NO:22).

As used herein, "lytic polysaccharide monooxygenase" and "LPMO" refer to a class of enzymes able to oxidatively cleave polysaccharides using a copper comprising moiety and using an oxygen source, such as a molecule of dioxygen, peroxide, or any other oxygen source; and a suitable reducing agent. As such, when an LPMO is used, the enzymatic reaction may be carried out under aerobic conditions. Suitable reducing agents are not particularly limited, but examples include ascorbic acid, gallic acid, cysteine, NADH, NADPH, pyrogallol, dithiothreitol, cyanoborohydrides, borohydrides, photosynthetic pigments, lignin, lignols, and a combination of cellobiose and cellobiose dehydrogenase. While the skilled person knows a wide variety of photosynthetic pigments which may be used, thylakoids and purified fractions, or chlorophyllin, are preferred, and light may be supplied. Preferably, LPMOs are selected from the following families: AA9, AA10, AA11, AA13, AA14, and AA15. More preferably, the LPMO is PaLPMO9E (SEQ ID NO:1), an AA9 LPMO originally isolated from the ascomycete fungus *Podospora anserina*. More preferably still, the LPMO is an AA9 LPMO from *Trichoderma reesei* (SEQ ID NO:25).

Aerobic conditions may comprise the addition of oxygen, which may be provided by aeration of the substrate mixture with an oxygen-comprising gas, such as air. Aeration may be conducted by the introduction of oxygen-comprising air bubbles into the aqueous substrate mixtures by various systems, such as an air-injector, an aeration frit, a membrane system, or an internal-loop airlift reactor. Preferably, the concentration of molecular oxygen in the enzymatic reaction is from about 4 mg/L to about 14 mg/L.

Another exemplary enzyme is a lichenase, which may be selected from the GH5, GH7, GH8, GH9, GH12, GH16, GH17, or GH26 families, preferably a GH16 enzyme, more preferably a GH16 enzyme derived from *Bacillus subtilis* (SEQ ID NO:2). The enzyme may be able to act on, for example, mixed-linkage glucans, which are glucans comprising a mixture of β-1,3 and β-1,4 linkages, and may cleave them at β-1,4 glycosidic bonds. In the preferable case in which the lichenase acts on a mixed-linkage glucan, the β-glucans produced may fall largely within the size range of from 3 to about 7 residues, so they are particularly useful in the food, cosmetics, and nutraceutical industries. Mixed-linkage glucans are abundant in members of the grass and horsetail families, and as such, grass-based feedstocks such as straw have high levels of mixed-linkage glucans and may be acted upon usefully with lichenases. Preferred lichenases include GH5 lichenase from *Bacillus subtilis* (SEQ ID NO:2).

Another alternative enzyme is a xylanase, which may act on, for example, feedstocks comprising a xylan backbone. The xylanase may be, for example, a glucuronoxylanase, an arabinoxylanase, or a glucuronoarabinoxylanase. The enzyme may be active on a variety of polymers having a xylan backbone, such as glucuronoxylan, arabinoxylan, and glucuronoarabinoxylan. These polymers are abundant in various plant-derived feedstocks, for example, both hardwood and softwood may comprise appropriate polysaccharides, with hardwood often comprising glucuronoxylan and softwood often comprising arabinoglucuronoxylan. Preferred xylanases include GH5 xylanases from *Ruminiclostridium thermocellum* (SEQ ID NO:3) and *Gonapodya prolifera* (SEQ ID NO:4), and GH30 xylanases from *Dickeya chrysanthemi* (SEQ ID NO:5), *Bacillus subtilis* (SEQ ID NO:6) and *Bacteroides ovatus* (SEQ ID NO:7) and *Trichoderma reesei* (SEQ ID NO:15 and 16).

Another alternative enzyme is a mannanase, which may act on, for example, feedstocks comprising a mannan backbone. The mannanase may be, for example, a mannanase, an glucomannanase, a galactomannanase or a galactoglucomannanase. The enzyme may be active on a variety of polymers having a mannan backbone, such as mannan, glucomannan, galactomannan or galactoglucomannan. These polymers are abundant in various plant-derived feedstocks, for example both hardwood and softwood may comprise appropriate polysaccharides. Preferred mannanases include GH5 mannanases from *Trichoderma reesei* (SEQ ID NO:17) and *Aspergillus niger* (SEQ ID NO:19) and a GH26 mannanase from *Aspergillus niger* (SEQ ID NO:18).

Other enzymes include xyloglucanases and xyloglucan endoglucanases (XEGs), which are produced by numerous organisms, including plant-pathogenic microbes. Xyloglucanases and XEGs may be able to act on xyloglucan, a hemicellulosic β-1,4 glucan chain abundant in the primary cell wall of higher plants, which is decorated with xylose, some of the xylose residues being further decorated with other residues, such as galactose. When appropriate xyloglucanases or XEGs act on xyloglucan, the products may comprise xyloglucan oligosaccharides having a main chain of a length useful in the foodstuff, cosmetics, and nutraceutical industries. Preferred xyloglucanases include is a GH5 xyloglucanase from *Bacteroides ovatus* (SEQ ID NO:8), and a GH74 xyloglucanase from *Trichoderma reesei* (SEQ ID NO:9).

Enzymes used in such enzymatic reactions may have a sequence which has at least 70%, 75%, 80%, 85%, 90%, 95%, or 100% identity to a sequence of SEQ ID Nos: 1-25. Enzymes used herein may be functional equivalents of enzymes described herein or functional equivalents of SEQ ID Nos: 1-25.

The enzymatic reaction may take place in solution and/or suspension or in a suitable reaction vessel. At a temperature or temperature protocol appropriate for the particular combination of enzyme and feedstock, the reaction may be allowed to progress for a certain amount of time (e.g., a predetermined amount of time), until the products have reached a desired concentration, or until some other requirement has been met.

As used herein, "suspension" refers to a composition comprising at least two immiscible phases, for example, a solid and a liquid phase, wherein the weight of the solid phase may be, as a percentage of the weight of the composition, in the range of from 0.5% to 30%, preferably from 1% to 20%, more preferably from 2% to 15%, yet more preferably from 3% to 10%. The suspension may comprise a suitable solvent, which is preferably water.

In order to ensure optimal contact between the enzymes and feedstock, the reaction mixture may be agitated, either constantly or at intervals. The agitation may take the form of (i) rhythmically moving the entire reaction vessel, (ii) a fan or other stirring device, (iii) a bubble spurging, or any other suitable method of agitation.

The enzymatic reaction may be a microbial fermentation. The temperature and reaction time may be suitable for the growth of the microbial organism used. The microbial organism may be genetically altered to produce an enzyme suitable for the production of an oligosaccharide composition. The microbe may be, for example, a bacterium, for example *Escherichia coli*, or a fungus, such as *Saccharomyces cerevisiae* or *Trichoderma reesei*.

In some embodiments, an expression vector suitable for modifying the subject microorganism may be used such that it produces an enzyme or mixture of enzymes as described elsewhere herein. Where desired, the expression vector, which may be a plasmid or any other nucleic acid able to induce production of the enzyme, may comprise one or more of the following regulatory sequences so as to control the expression of the exogenous enzyme: regulatory sequences of a heat shock gene, regulatory sequences of a toxicity gene, regulatory sequences of a spore formation gene, or any other suitable regulatory sequence.

The enzymatic reaction can be carried out at a temperature or temperature protocol appropriate to the enzymes and substrates used. For example, the enzymatic reaction may be carried out at a constant temperature in the range of from 10° C. to 100° C., preferably from 20° C. to 80° C., more preferably from 40° C. to 60° C. If the enzymatic reaction takes the form of a microbial fermentation the temperature may be appropriate for such, for example, the enzymatic reaction may comprise the growth of *E. coli* and/or the temperature may be substantially constant and about 37° C.

The pH of the solution or suspension may affect the activity of the enzymes. Control of pH may aid in assuring that an enzymatic reaction proceeds at a suitable rate. The enzymatic reaction may take place at a pH in the range of from 2 to 10, preferably 3 to 8, more preferably 4 to 6.

The enzymatic reaction may be allowed to continue for a certain time period before optionally being quenched and the products isolated or otherwise collected. This time period may be from 1 minute to 6 days, and is preferably from 0.5 days to 5 days, more preferably from 16 hours to 96 hours. The reaction may alternatively be allowed to proceed until no further catalysis occurs.

The one or more feedstocks added to the enzymatic reaction may comprise polysaccharides. Such polysaccharides may have been produced by a separate reaction proceeding simultaneously or substantially simultaneously in the reaction vessel. The polysaccharides present in the enzymatic reaction may be partially cleaved by enzymes into useful oligosaccharides, leaving partially cleaved or uncleaved polysaccharides, which may include, but are not limited to, cellulose, xylan (such as glucuronoxylan, arabinoxylan, or glucuronoarabinoxylan), mannan (such as glucomannan, galactomannan, or galactoglucomannan), mixed-linkage glucan, xyloglucan chitin, chitosan, or lignocellulose.

The enzymatic reaction may be allowed to continue to run until there is from 5% to 75% undigested polysaccharide-containing feedstocks remaining, preferably 5% to 70%, preferably 5% to 65%, more preferably 5% to 55%, or more preferably 10% to 50%. This can be monitored or checked by reducing end assays, such as the anthrone assay and/or by chromatographic methods such as thin-layer chromatography and/or high-performance anion exchange chromatography.

Any substance which comprises appropriate polysaccharides may form part of the feedstock. As the foodstuff, cosmetic, and nutraceutical industries generally use a broad variety of oligosaccharides, the polysaccharides appropriate for taking part in the enzymatic reaction are not particularly limited. Feedstocks suitable for producing the oligosaccharide profile may comprise, for example, cellulose, lignocellulose, chitin, chitosan, xylan (such as glucuronoxylan, arabinoxylan, and glucuronoarabinoxylan) and/or mannan (such as glucomannan, galactomannan, or galactoglucomannan), however, any feedstock which can be suitably acted upon is envisaged. Preferably the feedstocks comprise sugar cane, corn stover, corn cob, wheat bran, wheat straw, hardwood, or softwood.

The feedstocks comprising such polysaccharides are also not particularly limited, as most plant matter is rich in such polymers. As such, the feedstock may comprise plant biomass such as grain, grain chaff, bean pods, seed coats, and/or other seed materials; seaweeds; corn stover, straw, bagasse, miscanthus, sorghum residue, switch grass, bamboo, and/or other monocotyledonous tissue; water hyacinth, leaf tissue, roots, and/or other vegetative matter; hardwood, hardwood chips, hardwood pulp, softwood, softwood chips, softwood pulp, paper, paper pulp, cardboard, and/or other wood-based feedstocks; crab shells, squid biomass, shrimp shells, and/or other marine biomass, and/or any combination of appropriate feedstocks. Preferably, the feedstock comprises wheat straw or wood. As any given natural feedstock is likely to comprise a mixture of different polysaccharides, it will sometimes be the case that a mixture of different enzymes is beneficial. Such a mixture may comprise one or more of any other enzyme. For example, such a mixture might comprise an LPMO with an endo-glucanase, a xylanase with a lichenase, a cellobiohydrolase with a mannanase, or an endo-glucanase with a cellobiohydrolase, in which the enzyme partners are present in molar ratios preferably from 1:100 to 100:1. In addition, as many appropriate feedstocks are recalcitrant, pre-treatment of the feedstock is envisaged.

As used herein, "pre-treatment" is any process which makes a feedstock more easily acted upon by the enzymes inherent in the enzymatic reaction step. The pre-treatment can occur before the enzymatic reaction, and may comprise acid treatment by, for example, sulphuric acid, phosphoric acid, or trifluoroacetic acid; alkali treatment by, for example, potassium hydroxide, sodium hydroxide, or ammonia fibre expansion; heat treatment by, for example, hot water, hot steam, or hot acid; ionic liquid treatment, and related technologies; Alcell pulping, and related technologies; supercritical solvent, such as supercritical water treatment; and/or enzyme treatment by, for example, a hydrolase, lyase, or LPMO, or any mixture of the above processes.

After the enzymatic reaction has progressed to a desired point, the one or more oligosaccharides and the one or more polysaccharides from the enzymatic reaction mixture are separated. This process can be performed in a variety of ways depending on the composition of the biomass used and the specificity of the enzymes used. As the reaction mixture will often comprise a mixture of soluble oligosaccharides and insoluble polysaccharides, the reaction mixture may be filtered to remove insoluble matter and prepare the soluble oligosaccharide obtained for further processing.

When used herein and otherwise unqualified, "soluble," "solubility," and grammatical variants refer to solubility in water.

The oligosaccharides may also be separated from the polysaccharides in a number of ways. They may be isolated based on solubility, so that a composition of soluble saccharides only is extracted for further processing, and/or isolated chromatographically to produce a composition with a narrower band of oligosaccharide chain lengths. Isolation may, for example, be based on precipitation, size-exclusion chromatography, ion-exchange chromatography, or filtration, ultrafiltration, or nanofiltration. In the case that isolation based on solubility is carried out, the profile of saccharides present in the isolated composition will depend on the original enzymatic reaction, as different polysaccharides decrease in solubility with length at different rates.

Also envisaged is the further treatment of all or part of the produced oligosaccharides to produce further products before incorporation into a foodstuff, cosmetic, or nutraceutical. This further treatment may comprise any chemical, physical, or enzymatic step, such as reduction, preferably reductive amination where appropriate; oxidation, caramelisation, modification with a Schiff base, or via the Maillard reaction, or by any combination of such steps, and may provide different products having properties which are improved for the desired purpose. For example, the caramelisation properties, calorific value, flavour, and colour may be modified. The oligosaccharides may also be purified, for example, through precipitation, size-exclusion chromatography, ion-exchange chromatography, or filtration, ultrafiltration, or nanofiltration.

Also envisaged is the further treatment of all or part of the produced polysaccharide fraction to produce products with improved properties before incorporation into a foodstuff, cosmetic, or nutraceutical. This further treatment may comprise any chemical, physical, or enzymatic step, such as alkylation or acid-treatment. The polysaccharides may also be purified, for example, through precipitation, size-exclusion chromatography, ion-exchange chromatography, or filtration, ultrafiltration, or nanofiltration.

Following optional modification and/or purification of the oligosaccharide and polysaccharide fractions, all or part of the fractions are then recombined at a ratio of from 1:100 to 1:1 polysaccharide:oligosaccharide, preferably from 1:10 to 1:1, preferably from 1:90 to 1:2, preferably from 1:80 to 1:3, preferably from 1:70 to 1:4, or preferably from 1:60 to 1:5. The specific ratio may depend on the desired properties of the final ingredient as well as the modifications and purifications that have been applied to the fractions. It may not be required to recombine all of the oligosaccharide and polysaccharide isolated from the enzymatic reaction. An example of a composition that can be generated by recombination of oligosaccharides is shown in FIG. 1. As shown in FIG. 1, the composition can have one or more oligosaccharides, wherein each type of oligosaccharide may have oligosaccharides with varying degrees of polymerization.

The fractions can be recombined in a variety of ways, for example, by mixing a solution comprising all or part of the oligosaccharide fraction and a solution and/or suspension comprising all or part of the polysaccharide fraction, which may further be spray-dried, lyophilised, or condensed in some other way. The fractions may also be recombined by mixing a dry form comprising all or part of the oligosaccharide fraction produced by spray-drying, lyophilisation, or condensation in some other way, with a dry form comprising all or part of the polysaccharide fraction, produced by spray-drying, lyophilisation, or condensation in some other way.

The oligosaccharide components of the final composition may comprise one or more of any type of oligosaccharide. Preferably they comprise cello-oligosaccharides, xylo-oligosaccharides, mixed-linkage glucan oligosaccharides, manno-oligosaccharides, xyloglucan oligosaccharides or chito-oligosaccharides, or derivatives of any of the aforementioned oligosaccharides.

Any such dry or liquid composition may be deemed an ingredient suitable for incorporation into a foodstuff, cosmetic, or nutraceutical at any stage of this process. This includes compositions that may be deemed to be an intermediate during the method, such as a composition formed after the recombining of the oligosaccharide and polysaccharide fractions prior to any further purification, optimisation, drying, dissolving, or any other such steps, as well as including the final composition obtained from the method.

As described herein, dry compositions may be formed by well-known methods in the art such as spray-drying and/or lyophilisation. The dry compositions can be dissolved into a solution of various liquids including water, syrups, pastes, solvents, alcohols, etc. to form the liquid composition ingredient suitable for incorporation into a foodstuff, cosmetic, or nutraceutical. Liquid compositions may be particularly useful in foods that require a smooth texture such as candy, chocolate, and yoghurts.

Following optional modification and/or purification of the oligosaccharide and polysaccharide fractions, all or part of the fractions may then be recombined at a ratio of from 1:100 to 1:1 polysaccharide:oligosaccharide, preferably from 1:10 to 1:1, preferably from 1:90 to 1:2, preferably from 1:80 to 1:3, preferably from 1:70 to 1:4, or preferably from 1:60 to 1:5. The specific ratio may depend on the desired properties of the final ingredient as well as the modifications and purifications that have been applied to the fractions.

Once a composition of the oligosaccharide products suitable for the application being considered is obtained, and further treatment and/or isolation is optionally carried out, the derivation of a foodstuff, cosmetic, or nutraceutical from the composition can furnish a very broad array of potential uses. The ingredients as described herein, can be useful in applications in which oligosaccharides, sugar, bulking sweeteners, low-intensity sweeteners, or other related food ingredients are conventionally used.

In some embodiments, a method for producing a foodstuff, cosmetic, or nutraceutical ingredient is described. The ingredient may comprise one or more oligosaccharides and one or more polysaccharides. The method may comprise the steps of:
  a) forming the one or more oligosaccharides and the one or more polysaccharides by an enzymatic reaction, said enzymatic reaction comprising the step of contacting, in a solution or suspension, one or more polysaccharide-cleaving enzymes and one or more feedstocks, wherein the one or more feedstocks comprise sugar cane, sugar cane bagasse, corn stover, corn cob, wheat bran, wheat straw, hardwood, softwood, cellulose, chitin, chitosan, xylan, xyloglucan, mixed-linkage glucan, mannan or lignocellulose;
  b) separating the one or more oligosaccharides and the one or more polysaccharides from the enzymatic reaction mixture; and then
  c) recombining the one or more oligosaccharides and the one or more polysaccharides to form the ingredient.

The one or more oligosaccharides may comprise cello-oligosaccharides, xylo-oligosaccharides, mixed-linkage glucan oligosaccharides, manno-oligosaccharides, xyloglucan oligosaccharides or chito-oligosaccharides, or derivatives of any of the aforementioned oligosaccharides.

The polysaccharide-cleaving enzymes may be one of cellulase, xylanase, xyloglucanase, endo-glucanase, cello-biohydrolase, mannanase, lichenase or a lytic polysaccharide monooxygenase (LPMO), preferably selected from the group consisting of AA9, AA10, AA11, AA13, AA14 and AA15. The polysaccharide-cleaving enzyme may be prepared from T. reesei fungi and/or the enzymatic reaction runs until there is 5-75% undigested polysaccharide-containing feedstocks remaining, preferably 5-65%, more preferably 5-50%.

The one or more polysaccharides may comprise cellulose, xylan, mannan, mixed-linkage glucan, chitin, chitosan or lignocellulose. The polysaccharide-containing feedstock may be pre-treated by acid, alkali, heat, pressure, and/or enzyme treatment. The polysaccharide-cleaving enzyme(s) may be operably linked to a catalytic or non-catalytic module, preferably wherein the polysaccharide-cleaving enzyme may be operably linked to a non-catalytic module and the non-catalytic module is a carbohydrate-binding module.

In this embodiment, after the separating of the one or more oligosaccharides and one or more polysaccharides, the one or more oligosaccharides and one or more polysaccharides may be: purified; and/or undergo chemical, physical, or enzymatic treatment, such as reduction, oxidation, caramelisation, or Maillard reaction; and/or may be recombined by combining a spray-dried powder of oligosaccharides with a dried polysaccharide powder.

In some embodiments, the ingredient comprises three or more oligosaccharides of different molecular weights, wherein the method may comprise forming the three or more oligosaccharides by an enzymatic reaction, said enzymatic reaction comprising the step of contacting, in a solution or suspension, one or more polysaccharide-cleaving enzymes and one or more feedstocks.

The polysaccharide-containing feedstock may comprise plant biomass, preferably sugar cane, corn stover, corn cob, wheat bran, wheat straw, hardwood, softwood, cellulose, chitin, chitosan, xylan, xyloglucan, mixed-linkage glucan, mannan or lignocellulose.

At least one of the polysaccharide-cleaving enzymes may comprise one of cellulase, xylanase, xyloglucanase, endoglucanase, cellobiohydrolase, mannanase, lichenase or a lytic polysaccharide monooxygenase (LPMO) and the polysaccharide-cleaving enzyme may be prepared from *T. reesei* fungi.

The composition may comprise monosaccharides at <5% w/w of total oligosaccharide component (comprising glucose, xylose and/or mannose), disaccharides at >20% w/w of total oligosaccharide component (comprising cello-, xylo- and/or manno-oligosaccharides), trisaccharides at >5% w/w of total oligosaccharide component (comprising cello-, xylo- and/or manno-oligosaccharides) and tetrasaccharides at >2% w/w of total oligosaccharide component (comprising cello-, xylo- and/or manno-oligosaccharides).

The polysaccharide-containing feedstock may be pre-treated by acid, alkali, heat, pressure, and/or enzyme treatment. The polysaccharide-cleaving enzyme(s) may be operably linked to a catalytic or non-catalytic module, preferably wherein the polysaccharide-cleaving enzyme is operably linked to a non-catalytic module and the non-catalytic module is a carbohydrate-binding module.

The oligosaccharides may be purified; and/or undergo chemical, physical, or enzymatic treatment, such as reduction, oxidation, caramelisation, or Maillard reaction; and/or are recombined by combining a spray-dried powder of oligosaccharides with a dried polysaccharide powder.

EXAMPLES

Example 1—Improved Dissolution of a Cello-Oligosaccharide and Xylo-Oligosaccharide Combination Composition Combining cellobiose with xylo-oligosaccharide improves the dissolution of xylo-oligosaccharides in jam.
1. 280 g strawberries were brought to boil in a saucepan.
2. After heating, the strawberries were blended.
3. 5 g of xylo-oligosaccharides in powder form, or 10 g of a 50:50 mix of xylo-oligosaccharides and cellobiose in powder form, was added to the blend.
4. After being left for 1 minute the powder was mixed in to the jam.
5. The xylo-oligosaccharide sample formed a clump that was difficult to mix into the blended strawberries, whereas the xylo-oligosaccharides and cellobiose mixture readily dispersed into the jam and did not form any clumps.

Example 2—Improved Dissolution of Oligosaccharide Combinations in Water

Dissolution of xylo-oligosaccharides into water are improved when mixed with other oligosaccharides such as cello-oligosaccharide, manno-oligosaccharide, and mixed-linkage glucan oligosaccharides (MLGOs).
1. 50 mg xylo-oligosaccharide powder was (a) left alone, or (b) mixed with 10 mg cellobiose, (c) mixed with 10 mg MLGOs or (d) mixed with 10 mg manno-oligosaccharides.
2. 0.5 mL water was added, and the tubes were incubated at room temperature for 5 minutes until water had fully soaked into the powder.
3. Each tube was then vortexed at high speed for 30 seconds.
4. An undissolved pellet remained in the xylo-oligosaccharide-only tube (a), which was absent from all of the others, whereas none of the other tubes (b-d) had pellets remaining.

Example 3—Baked Goods with Improved Characteristics

Combinations of cellobiose (cell$_2$), xylo-oligosaccharides (XOS), and cellulose produce cookies with improved characteristics
1. 40 g all-purpose flour, ⅛ teaspoon baking soda, and ¹⁄₁₆ teaspoon salt were mixed together.
2. 1 oz unsalted butter, half large egg yolk, and ¼ teaspoon vanilla extract were whisked with 20 g oligosaccharide mix (comprising xylo-oligosaccharides and/or cell$_2$) and optionally 6 g cellulose polysaccharide and was added to the mixture. There were 4 oligosaccharide mixes tested: 100% xylo-oligosaccharides, 67% xylo-oligosaccharides; 33% cell$_2$, 33% xylo-oligosaccharides; 67% cell$_2$, and 100% cell$_2$.
3. 30 g chocolate chips were mixed into the mixture.
4. 40 g balls were baked for 15 minutes at 350° F.

Figure 2:
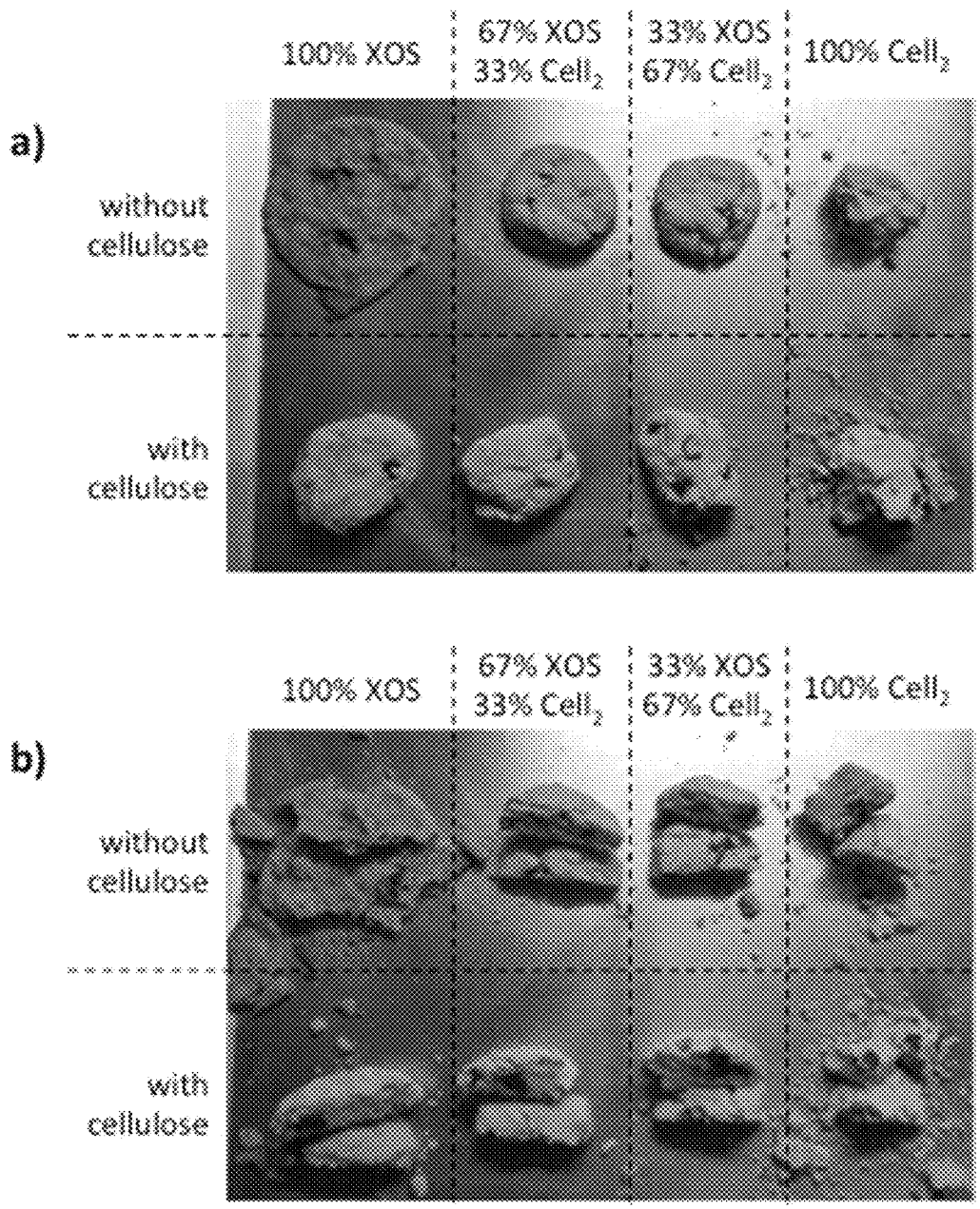
FIG. 2 shows cookies fresh out of the oven (panel a) and cut in half after a cooling period (panel b). The cookies were made using various compositions comprising combinations of cellobiose, xylo-oligosaccharides, and cellulose.

Without cellulose, the xylo-oligosaccharide-only cookies melted too quickly and formed crisp cookies that were too thin, and the cell$_2$-only cookies were dry and crumbly, as shown in FIG. 1. Cookies with combinations of cell$_2$ and xylo-oligosaccharides held their structure better and looked more like cookies. Of the cookies that contained cellulose polysaccharide, all developed cookie properties except for the cell$_2$-cellulose cookie, which was too crumbly. FIG. 2 shows the cookies fresh out of the oven (FIG. 2, panel a) and cut in half after a cooling period (FIG. 2, panel b). When cut, the cookies with combinations of oligosaccharide types, or oligosaccharide-polysaccharide combinations maintained their structure best. Cookies with combinations of cellobiose and xylo-oligosaccharides had better structure and mouthfeel than those made using only a single type of oligosaccharide. In conclusion, oligosaccharide combinations and oligosaccharide-polysaccharide combinations perform better as sugar substitutes in cookies than individual oligosaccharides.

Example 4—Improved Sweetness

Demonstrating improved sweetness of combinations of cello-oligosaccharide and xylo-oligosaccharide combinations
1. Five oligosaccharide solutions were created:
    a. 40 mg/mL xylo-oligosaccharide
    b. 80 mg/mL xylo-oligosaccharide
    c. 120 mg/mL cellobiose
    d. 120 mg/mL cellobiose, 40 mg/mL xylo-oligosaccharide
    e. 120 mg/mL cellobiose, 80 mg/mL xylo-oligosaccharide
2. Eleven participants were asked to taste 2 mL samples of the solutions sequentially from (a)-(e). Before each tasting, participants washed their mouths with water and after each tasting they were asked to assign a numerical value to the sweetness of the solution. The first solution in which they could taste sweetness was arbitrarily assigned a 1, and later solutions were assigned a number based on the factor by which they were sweeter than the former. Values were standardised to 1 for comparison.

Figure 3:
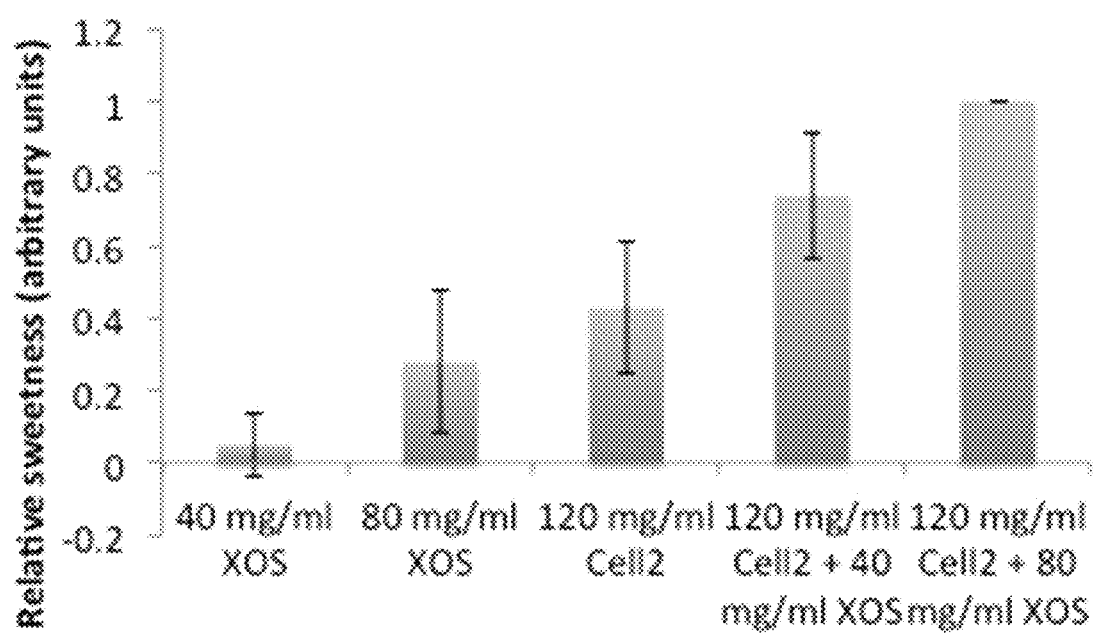
FIG. 3 shows the relative sweetness of various combinations of xylo-oligosaccharide-cellobiose in solution.

As shown in FIG. 3, the results show a synergistic impact of sweetness in the solutions with combinations of cellobiose and xylo-oligosaccharides compared to the solutions with only cellobiose or xylo-oligosaccharides.

Figure 4:
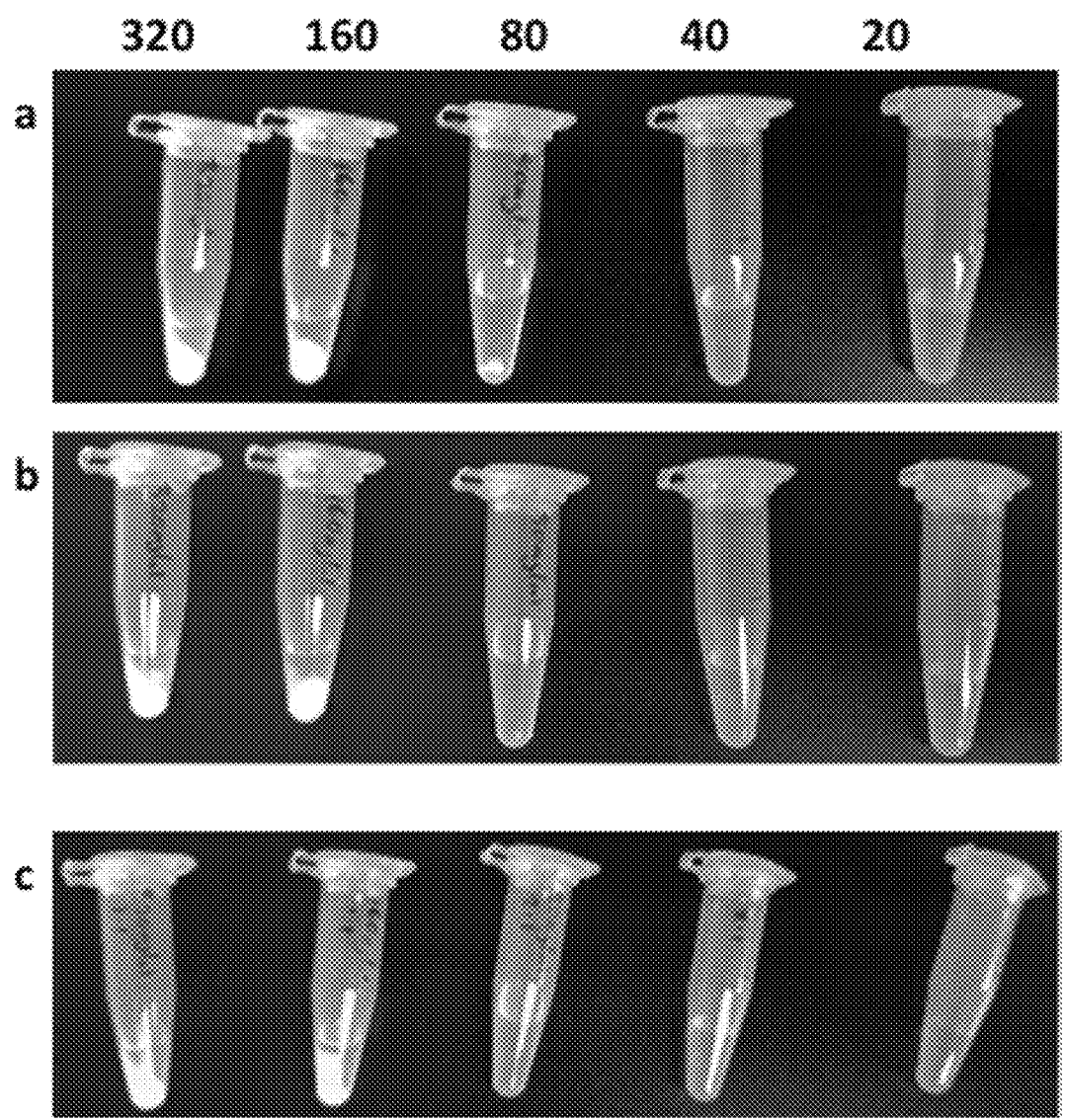
FIG. 4 shows solutions/suspensions of cellobiose at concentrations from 20-320 mg/mL after being vortexed for 30 seconds alone (panel a), or in the presence of half the concentration of xylo-oligosaccharides (panel b) or the same concentration of xylo-oligosaccharides (panel c).

Example 5—Improved Solubility of Cellobiose when Combined with Xylo-Oligosaccharides 1. Solutions/suspensions of cellobiose at concentrations from 20-320 mg/mL were vortexed for 30 seconds alone (FIG. 4, panel a), in the presence of half the concentration of xylo-oligosaccharides (FIG. 4, panel b), or the same concentration of xylo-oligosaccharides (FIG. 4, panel c).
2. Dissolution was enabled more readily at higher concentrations through the presence of xylo-oligosaccharides (e.g., at 80 mg/mL).

Figure 5:
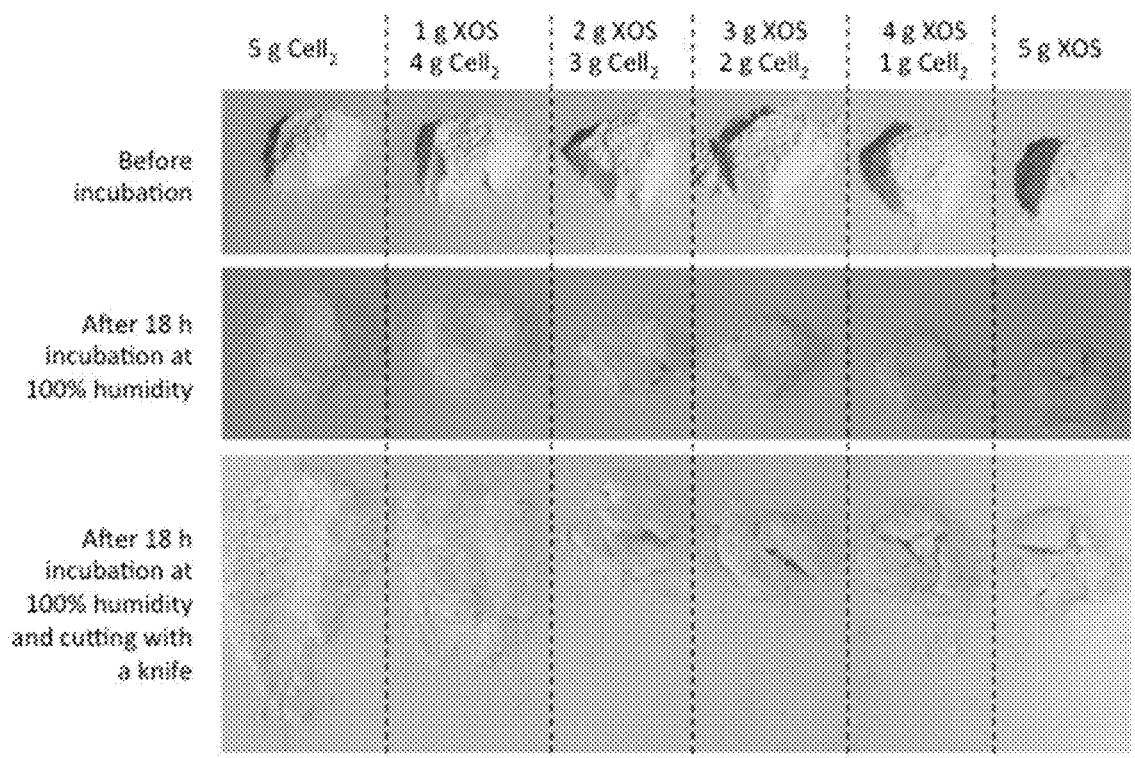
FIG. 5 shows the hygroscopicity of various cellobiose-xylo-oligosaccharide compositions.

Example 6—Modifying Hygroscopicity of Oligosaccharide Powder by Changing Compositions The compositions are to be used in a wide range of foodstuff, cosmetic, or nutraceutical applications, therefore the required hygroscopicity for each application can vary. The aim of this example was to test if hygroscopicity can be adapted by altering the oligosaccharide compositions.
1. 5 g of oligosaccharide compositions (cellobiose, 4:1 cellobiose:xylo-oligosaccharide, 3:2 cellobiose:xylo-oligosaccharide, 2:3 cellobiose:xylo-oligosaccharide, 1:4 cellobiose:xylo-oligosaccharide, xylo-oligosaccharide) were incubated for 10 hours at 25° C. in 100% humidity.
2. After incubation, oligosaccharide samples were cut using a kitchen knife to demonstrate water capture. The cellobiose and the 4:1 cellobiose:xylo-oligosaccharide samples effectively resisted water uptake, whereas the other samples increasingly absorbed water, as shown in FIG. 5. This shows that the hygroscopicity of the composition can be modified to the desired level in order to meet the requirements of its application.

Example 7—Baked Goods Made Using Undigested Polymeric Cellulose

Figure 6:
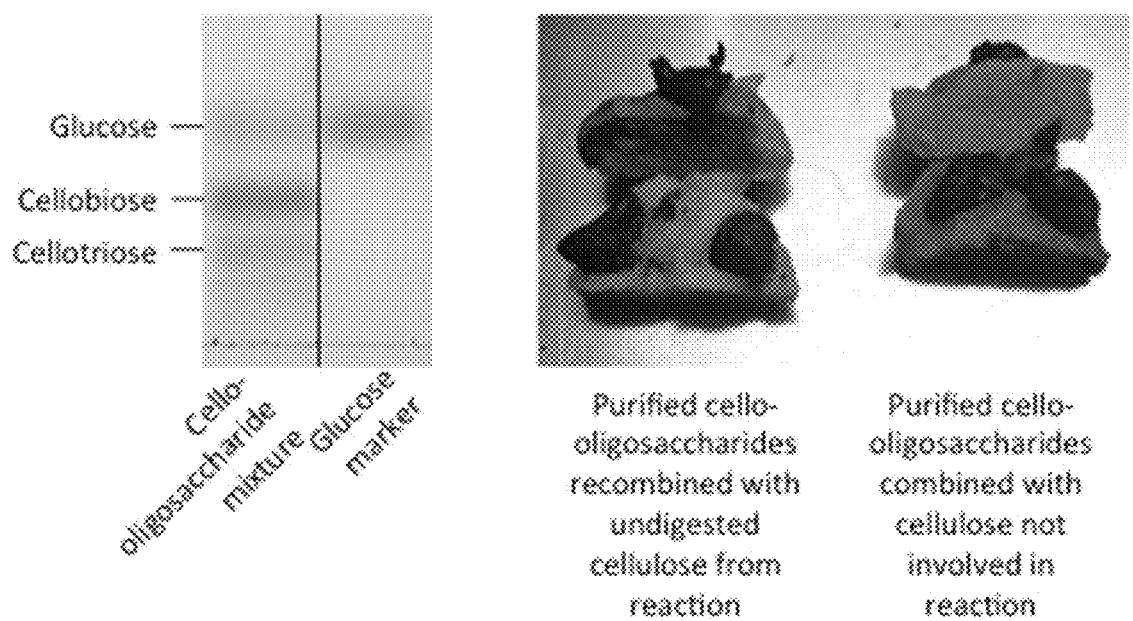
FIG. 6 shows the oligosaccharide profile analysed by thin-layer chromatography of the cello-oligosaccharide mixture produced by the enzymatic reaction on microcrystalline cellulose, and cakes made using the oligosaccharides with either the dried undigested microcrystalline cellulose from cellulolytic reactions or untreated microcrystalline cellulose.

Undigested polymeric cellulose from hydrolase reaction can perform functionally in cakes as well as untreated polymeric cellulose
1. 10 g microcrystalline cellulose was incubated for 36 hours at 37° C. in 400 mL solution containing 2 mg GH7 cellobiohydrolase I (*Trichoderma longibrachiatum*), 5 mg GH12 cellulase (*Aspergillus niger*), and 0.3 mg GH6 cellobiohydrolase II (microbial) (all purchased from Megazyme, Ireland) with constant agitation at 800 rpm.
2. After the reaction, the oligosaccharide profile was analysed by thin-layer chromatography showing 41% breakdown of polymeric cellulose into cello-oligosaccharides comprising mainly cellobiose with some cellotriose, cellotetraose, and glucose (shown in FIG. 6).
3. The cello-oligosaccharide mixture was separated from the undigested cellulose through filtration and both were dried.
4. The undigested cellulose from the reaction was heated at 100° C. for 1 hour in 1M NaOH before being washed with water until neutral and dried.
5. 2 g dried cello-oligosaccharide mixture was mixed with either 2 g dried undigested cellulose from the reaction or 2 g microcrystalline cellulose.
6. The two samples were whipped with 4 g unsalted butter, before mixing in 4 g egg, and then 4 g flour.
7. 4 g semi-sweet chocolate chips were added to the batter.
8. Mini cupcakes were baked at 37° C. for 10 minutes.
9. Cakes were cooled and cut in half. Results showed that the dried undigested cellulose from cellulolytic reactions performed identically to microcrystalline cellulose in cake structure.

Example 8—Baked Goods Made Using Undigested Polymeric Lignocellulose

Figure 7:
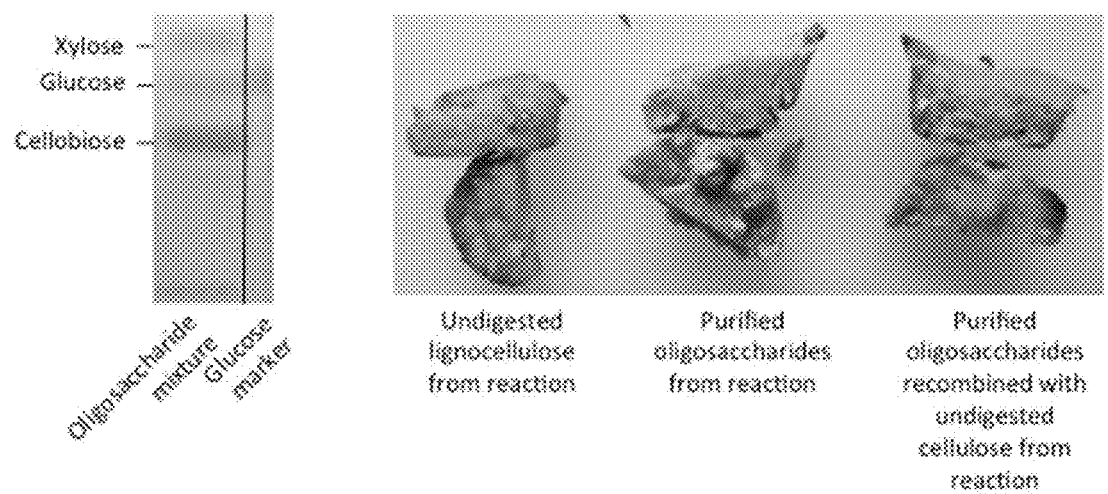
FIG. 7 shows the oligosaccharide profile analysed by thin-layer chromatography of the oligosaccharide mixture produced by the enzymatic reaction on wheat bran lignocellulose, and cakes made using the undigested lignocellulose from cellulolytic reaction alone, the oligosaccharides from cellulolytic reaction alone, and the undigested lignocellulose from cellulolytic reaction in combination with oligosaccharides from cellulolytic reaction.

Undigested polymeric lignocellulose from partial cleavage of corn cob can be added to cake mix without decrease in cake properties.
1. 10 g dried corn cob was grated into very fine pieces, ground in a slurry using a pestle and mortar, and incubated at 100° C. for 30 minutes.
2. The slurry was then incubated for 36 hours at 37° C. in 400 ml solution containing 1.6 ml *T. reesei* cellulase extract.
3. After the reaction, the oligosaccharide profile was analysed by thin-layer chromatography showing 68% breakdown of polymeric lignocellulose into oligosaccharide comprising mainly cellobiose with some xylose and glucose.
4. The oligosaccharide mixture was separated from the undigested lignocellulose through filtration and dried.
5. Three samples (4 g dried oligosaccharide mixture; 2 g dried oligosaccharide mixture plus 2 g dried undigested lignocellulose; and 4 g dried undigested lignocellulose) were whipped with 4 g unsalted butter, before mixing in 4 g egg, and then 4 g flour.
6. Mini cupcakes were baked at 37° C. for 10 minutes.
7. Cakes were cooled and cut in half. As shown in FIG. 7, the results showed that undigested lignocellulose from cellulolytic reactions alone gave poor structural support to the cake. However, in combination with oligosaccharides, undigested lignocellulose gave comparable support to cake structure.

Figure 8:
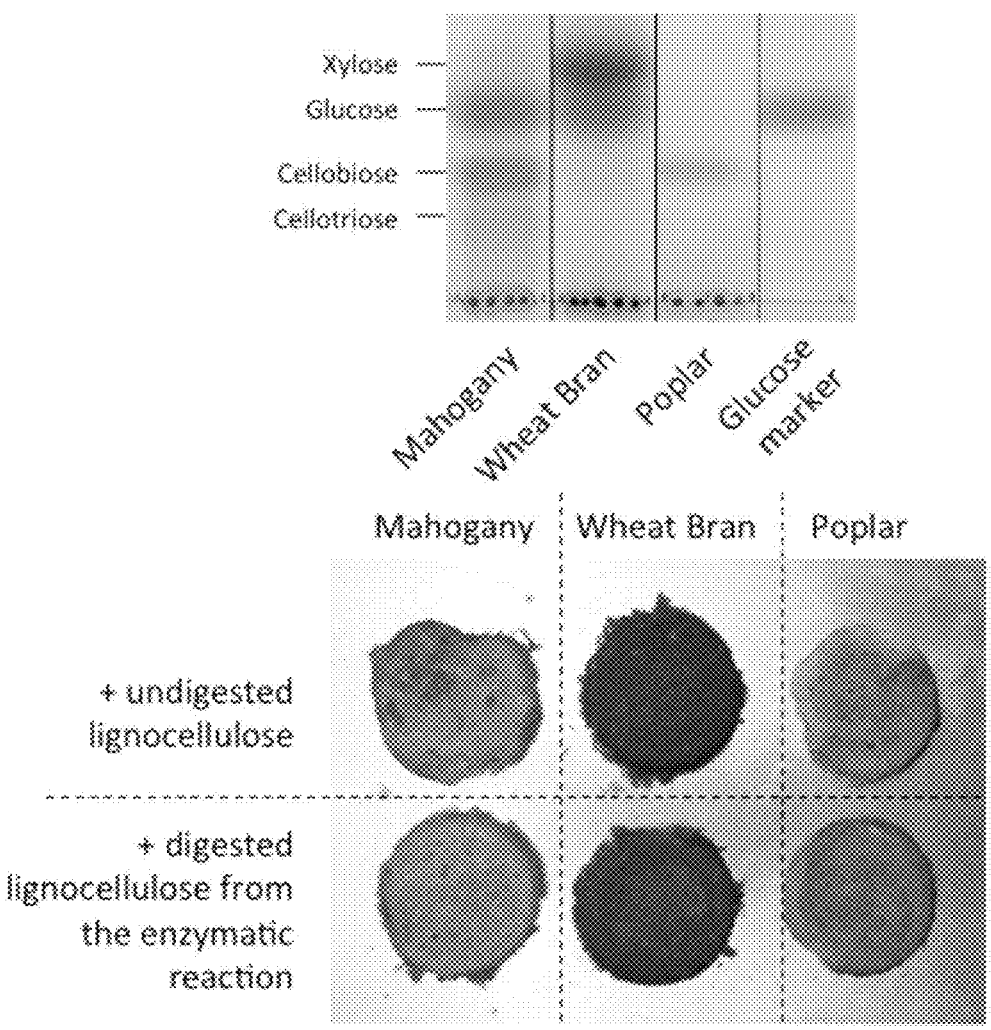
FIG. 8 shows the oligosaccharide profile analysed by thin-layer chromatography of the oligosaccharide mixture produced by the enzymatic reaction, and cakes made using the oligosaccharides from cellulolytic reaction along with the undigested lignocellulose from cellulolytic reactions or with fresh lignocellulose.

Example 9—Baked Goods with Undigested Polymeric Lignocellulose from Partial Cleavage of Mahogany Wood, Wheat Bran, and Poplar Wood Undigested polymeric lignocellulose from partial cleavage of mahogany wood, wheat bran, and poplar wood functions better in cakes than fresh mahogany wood, wheat bran, and poplar wood
1. 10 g dried mahogany wood, wheat bran, and poplar wood were ground in a slurry using a pestle and mortar and incubated at 100° C. for 30 minutes.
2. The mahogany slurry was incubated for 36 hours at 37° C. in 400 ml solution containing 1.6 ml *T. reesei* cellulase extract and 2 mg GH26 Mannanase (*Cellvibrio japonicas*; purchased from Megazyme, Ireland). The wheat bran slurry was incubated for 36 hours at 37° C. in 400 mL solution containing 1.6 ml *T. reesei* cellulase extract. The poplar slurry was incubated for 36 hours at 37° C. in 400 mL solution containing 2 mg GH7 cellobiohydrolase I (*Trichoderma longibrachiatum*), 5 mg GH12 cellulase (*Aspergillus niger*), 0.3 mg GH6 cellobiohydrolase II (microbial) (all purchased from Megazyme, Ireland), 10 mg *Aspergillus oryzae* xylanase (purchased from Sigma).
3. After the reaction, the oligosaccharide profile was analysed by thin-layer chromatography showing 68% breakdown of polymeric lignocellulose into oligosaccharide comprising mainly cellobiose with some xylose and glucose.
4. The oligosaccharide mixture was separated from the undigested lignocellulose through filtration and dried.
5. For each of the three lignocellulose types, 2 g dried oligosaccharide mixture was mixed with 1 g dried undigested polysaccharide from the reaction or 1 g fresh lignocellulose. For each of the three lignocellulose types, the two 3 g saccharide compositions made were whipped with 3 g unsalted butter, before mixing in 3 g egg, and then 3 g flour.
6. Mini cupcakes were baked at 37° C. for 10 minutes.
7. Cakes were cooled and analysed. As shown in FIG. 8, the results showed that the fresh lignocellulose incorporated less-well into the structure of the cake than the recombined undigested lignocellulose from the enzymatic reactions did. In the former, distinct pieces of lignocellulose were conspicuous in the mahogany and wheat bran cakes, and less so in the poplar cake. In contrast, lignocellulose pieces were hardly noticeable in the cakes containing recombined undigested lignocellulose from the enzymatic reactions.

Example 10—Gastrointestinal Tolerance

Addition of polymeric cellulose to cellobiose-xylo-oligosaccharide compositions improves gastrointestinal tolerance.

The compositions are to be used in a wide range of foodstuffs, ideally up to levels comparable to sugar consumption in the average Western diet (~80 g/day). It is known that, at these levels, oligosaccharides, such as xylo-oligosaccharides, can cause gastrointestinal distress, including diarrhoea, discomfort, and bloating. For xylo-oligosaccharides the highest tolerated dose is 12 g/day. The aim of this example was to test if adding different polysaccharides to the oligosaccharide preparation before consumption would increase the gastrointestinal tolerance of the oligosaccharides, for example, by slowing gastric emptying, and enable far higher volumes to be comfortably consumed.
1. The experiments were performed on 2 healthy male volunteers aged 22 and 31.
2. For 17 days, each volunteer consumed an average of 30 g test oligosaccharides comprising cellobiose and xylo-oligosaccharides at ratios from 0:1 to 4:1. The maximum consumed on a single day was 50 g and the minimum was 20 g.
3. One volunteer reported diarrhea on day 2 and heavy diarrhoea on day 17. The second volunteer reported minor discomfort and bloating on some days.
4. For the next 12 days, each volunteer consumed an average of 70 g of test saccharides comprising cellobiose and xylo-oligosaccharides at ratios from 0:1 to 4:1, supplemented with microcrystalline cellulose or carboxymethylcellulose at 5-33% of the total test saccharide. The maximum consumed on a single day was 110 g and the minimum was 40 g.
5. No gastrointestinal symptoms were observed.

This confirmed that concomitant consumption of polysaccharides with the oligosaccharides improves tolerance and enables comfortable consumption of much larger amounts of oligosaccharide and at levels comparable to sugar consumption in the average Western diet (~80 g/day).

Example 11—Moisture Content

Four different compositions were made by mixing individual saccharide powders and undigested biomass. Sample 1 comprises 15% undigested biomass mixed with 45% xylo-oligosaccharide and 40% cellobiose w/w. Sample 2 comprises 50% xylo-oligosaccharide mixed with 50% cellobiose w/w. Sample 3 comprises 10% xylo-oligosaccharide mixed with 90% cellobiose w/w. Sample 4 comprises 90% xylo-oligosaccharide mixed with 10% cellobiose w/w.

The TES-AC-097 (UKAS) method was used to measure the moisture content. In this method the sample was heated to 70° C. in a vacuum chamber overnight and the loss in weight was measured. The moisture content results are given in Table 1 below. Sample 1 had the highest moisture content whereas sample 3 had the lowest. Samples 2 and 4 had intermediate moisture content between these two extremes and had similar moisture content to each other. The effect of moisture on flowability of particles can vary depending on the nature of the material. When particles absorb water, they can become cohesive and flow properties can be adversely affected. The higher moisture content found in Sample 1 may provide improved characteristics such as binding, moistness, etc. in baked goods.

TABLE 1

| Moisture content of powders (TES-AC-097 (UKAS)) | |
|---|---|
| Sample number | Moisture content (g/100 g) |
| Sample 1 | 4.01 |
| Sample 2 | 1.2 |
| Sample 3 | 0.7 |
| Sample 4 | 1.4 |

Example 12—Digi Eye Imaging

Figure 9:
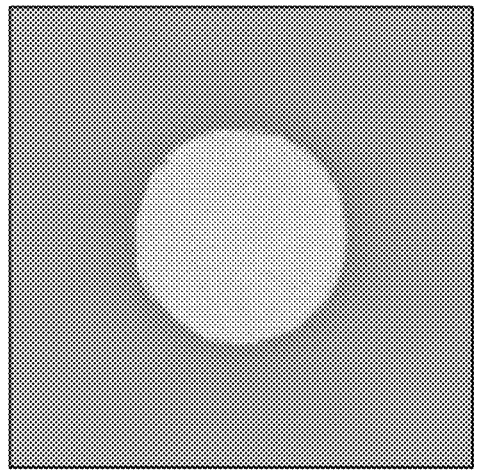
FIG. 9 shows colour images captured for samples 1, 2, 3, and 4 using a Digi Eye system.
Figure 9:
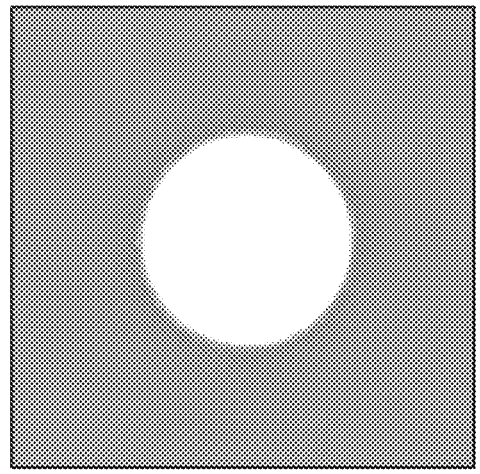
Figure 9:
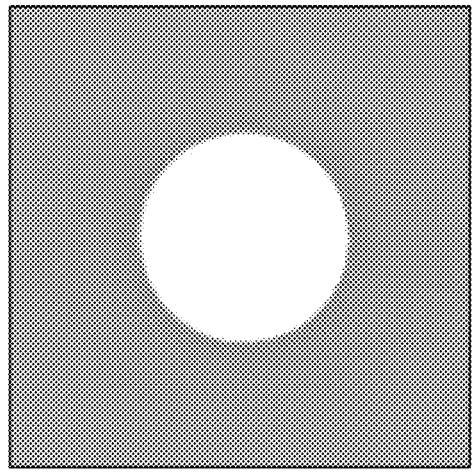
Figure 9:
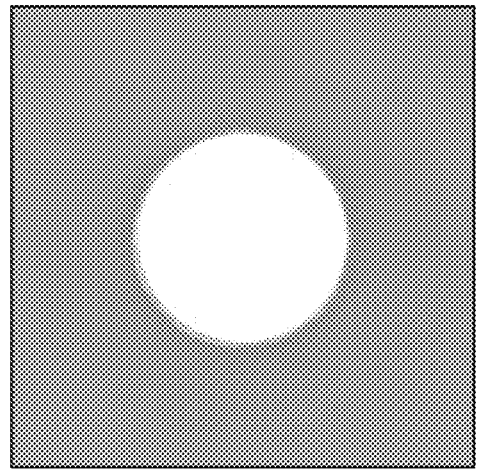

Samples from Example 11 were used and colour images were captured using a DigiEye system (Verivide). This instrument comprises an imaging cabinet with controlled D65 lighting conditions and a camera. Diffuse lighting, a fixed magnification, and consistent presentation conditions were used for all images. FIG. 9 shows colour calibrated DigiEye images for all samples. The results for the imaging show that Sample 1 has a different colour due to the presence of biomass as compared to oligosaccharide mixtures in samples 2, 3 and 4.

Example 13—Colour Analysis

Colour measurements for samples from Example 11 were taken in triplicate using a CM-5 instrument (Konica Minolta) according to method TES-CM-126. The samples were transferred into a glass petri dish and the average colour measurements were performed on a 30 mm diameter surface area in reflectance mode using a D65 illumination and 10° observation.

Figure 10A:
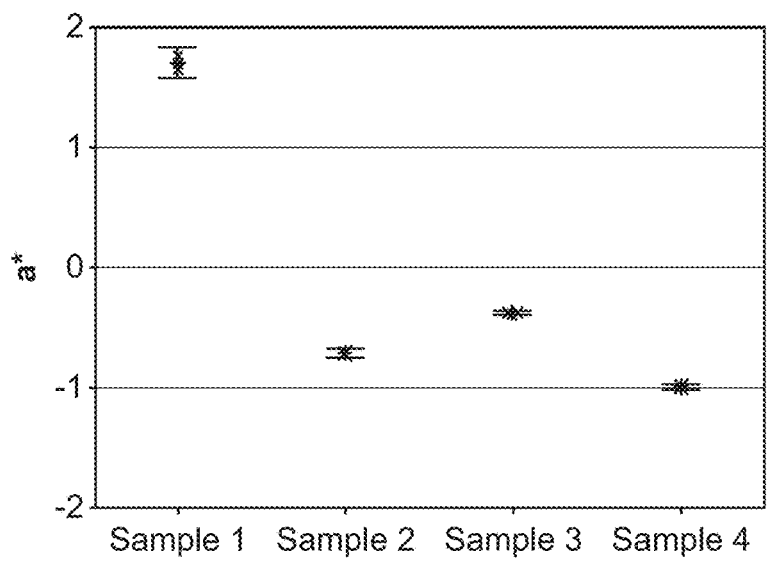
FIGS. 10A-10C show colour measurements of oligosaccharide samples.
Figure 10B:
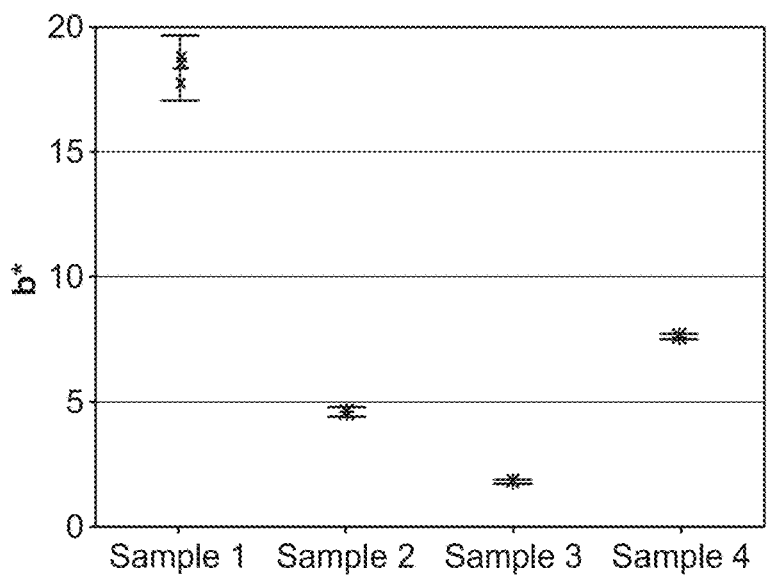
Figure 10C:
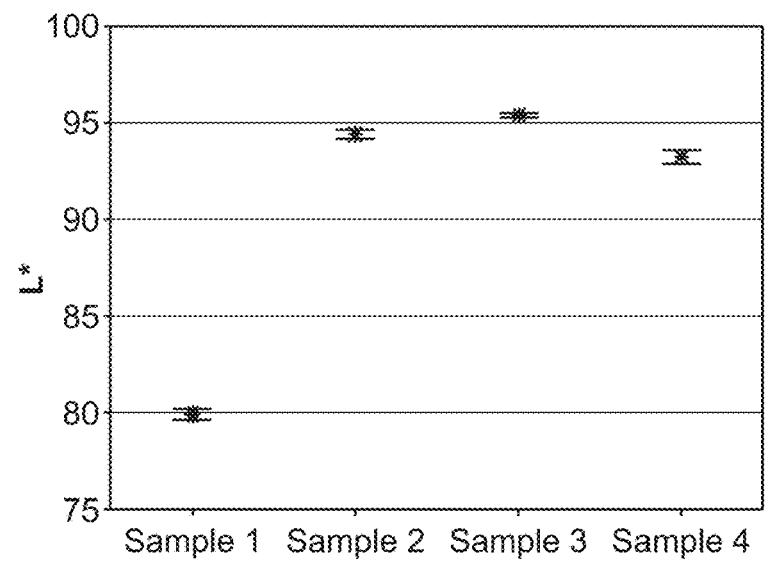

Colour measurements were recorded using CIELAB colour space, three coordinates (L*, a*, b*) are associated with each colour:
L*: Lightness (where L*=0 is black and L*=100 is white) is as shown in FIG. 10C.

a*: Position along an axis from green to red (where positive a* values indicate redness and negative a* values indicate greenness) is as shown in FIG. 10A.

b*: Position along an axis from blue to yellow (where positive b* values indicate yellowness and negative b* values indicate blueness) is as shown in FIG. 10B.

The four samples all had significantly different L*, a*, b* values from each other, Sample 1 being the most different as shown by the colour differences ΔE in Table 2. Sample 3 had the whitest colour, white being defined by the L*, a*, b* values 100, 0, 0, respectively. Sample 1 had the darkest colour and had the strongest red and yellow colour. Sample 1 also showed the widest confidence intervals due to the non-uniformity of the powder with some dark and light particles. The colour differences ΔE between all the samples are greater than 1, representing a visually perceptible colour difference. In summary, the colour of Sample 1 was the most different from the other samples and Sample 3 was the closest to a white colour.

TABLE 2

Table of the colour differences ΔE between samples

|  | Sample 1 | Sample 2 | Sample 3 | Sample 4 | White |
|---|---|---|---|---|---|
| Sample 1 | — | 20.13 | 22.77 | 17.34 | 27.28 |
| Sample 2 | 20.13 | — | 2.99 | 3.25 | 7.30 |
| Sample 3 | 22.77 | 2.99 | — | 6.23 | 5.00 |
| Sample 4 | 17.34 | 3.25 | 6.23 | — | 10.24 |
| White | 27.28 | 7.30 | 5.00 | 10.24 | — |

Example 14—Hygroscopicity Measurements

Figure 11:
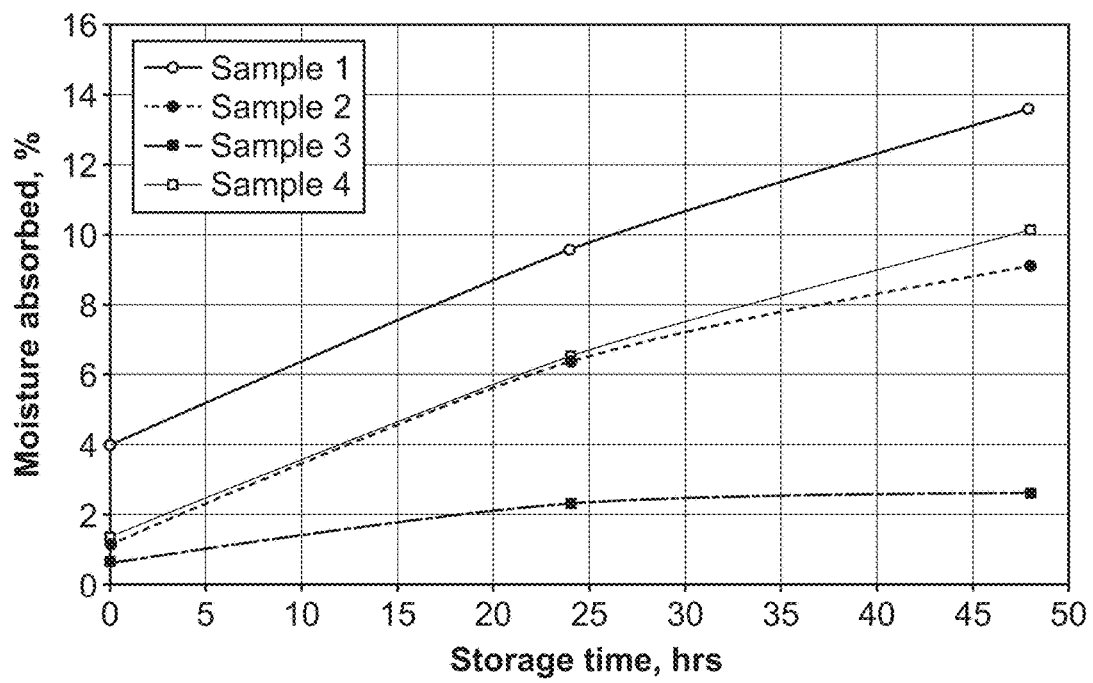
FIG. 11 shows hygroscopicity profiles of samples 1, 2, 3, and 4.

Approximately 5 g of each sample from Example 11 was weighed into aluminium foil dishes and covered with foil. Several holes were made in the foil cover to allow moisture to enter the dish but prevent contamination from airborne debris or powder being lost. The samples were stored in a temperature and humidity-controlled room (20° C. and 70% relative humidity) and the change in weight of the samples measured after 24 and 48 hours. Each sample was measured in duplicate. The results of the hygroscopicity measurements as shown in FIG. 11 show that all samples had the tendency to pick up moisture from the atmosphere at 20° C. and 70% relative humidity. Sample 3 had the lowest moisture content to begin with and picked up less moisture than the other samples. The trend on graph for sample 3 suggests that moisture pickup had reached an equilibrium or was very close to an equilibrium with the surrounding atmosphere. This sample had not clumped together after 48 hours. Sample 1 had the highest moisture content and absorbed moisture at a faster rate than sample 3 which is unexpected. The rate of moisture pick-up of sample 1 was similar to samples 2 and 4. After 48 hours, sample 1 had formed some clumps. Samples 2 and 4 had intermediate moisture content between samples 1 and 3 and absorbed moisture from the atmosphere at a similar rate to each other up to 24 hours. Sample 4 absorbed more moisture between 24 and 48 hours compared with sample 2. Sample 3 did not show any clump formation but sample 4 had lost its particulate nature and formed a viscous liquid. It could therefore be described as deliquescent.

The hygroscopicity measurements were repeated on samples that had been dried overnight at 70° C. under vacuum. This was to ensure that any historical moisture absorbed by the samples was removed and were dry when the hygroscopicity test was started. It was noteworthy to report that after drying sample 1 was in the form of hard lumps of various sizes and difficult to break. The lumps were broken up and the powder sieved through a 500 μm sieve to obtain free flowing particles of the sample. Samples 2-4 were free-flowing powders after drying. The percentage moisture gained is given in FIG. 6 and as before sample 3 absorbed the least amount of moisture from the atmosphere over the 96-hour period. Sample 4 absorbed the highest amount of moisture in the same period and had changed to a viscous liquid as was found in the first study. The rate of moisture pickup by sample 4 was greater than the other three samples. Sample 1 absorbed more moisture than sample 2, but the rate of moisture pickup appeared to be similar for these two samples Example 15—Cohesion Strength of Powders The cohesion strength describes a powder's internal flow resistance, which depends on the adhesive forces between the particles. The measurements for samples made in Example 11 were conducted with an Anton Paar MCR Rheometer MCR102 equipped with a Powder Cell, a powder fluidizer with mass-flow controller (Fluidization Set Scientific), and a two-blade stirrer. The cohesion strength is determined with the two-blade stirrer from the torque recorded during the measurement and a geometry-specific factor. The method consists of two steps. During the first interval, residual influences from previous powder handling are erased. This is known as the Pressure-Drop Method. This was achieved by fully fluidizing the sample for 60 seconds. During the second interval, a constant rotational speed of 8 rpm was set while the volumetric flow was zero. The cohesion strength S in Pa was calculated by using linear regression over the last 20 data points.

Figure 12:
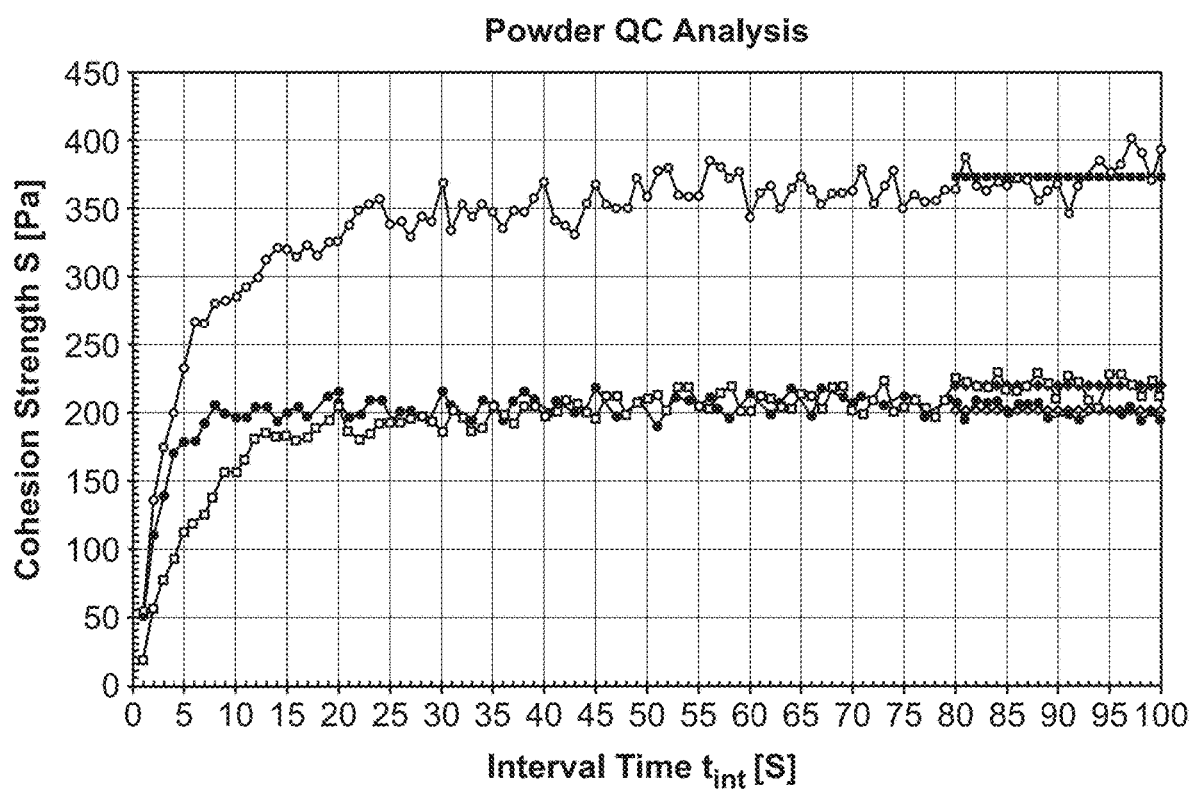
FIG. 12 shows cohesion strength of samples 1, 2, 3, and 4.

The examples of the traces of the cohesion strength obtained of samples 2 to 4 are shown in FIG. 12. The analysis of the traces is given in Table 3. The cohesion strength of samples 2 and 3 was significantly lower than that of sample 4. The higher value of sample 4 indicate higher cohesive forces between the particles. This might be due to different particle sizes and particle-size distributions and thus, different cohesion strengths. Sample 4 also had higher bulk density, suggesting greater inter-particle interaction and this may also be a factor contributing to the higher cohesion strength. Sample 1 was not measured as it could not be fluidised. This suggests that the cohesion strength of this powder was high, and this may be due to the high moisture content of this sample as well as other factors.

TABLE 3

Cohesion strength of powder samples.

| Sample number | Cohesion Strength (Pa) |
|---|---|
| Sample 1 | Did not fluidise |
| Sample 2 | 207.1 ± 4.6 |
| Sample 3 | 217.5 ± 2.6 |
| Sample 4 | 380.5 ± 7.6 |

Example 16—Viscosity

Figure 13:
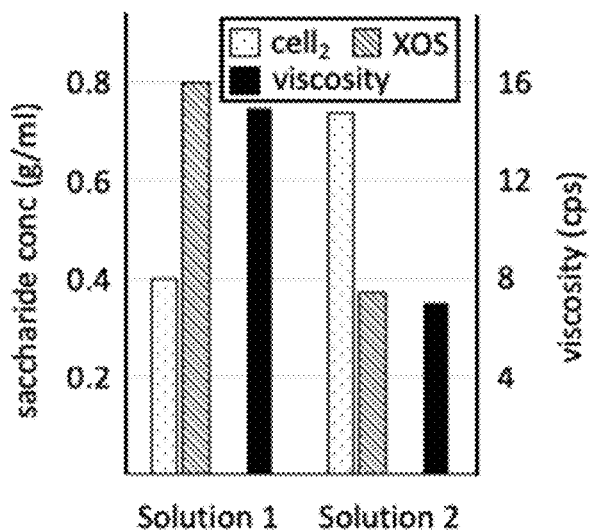
FIG. 13 shows viscosity of cellobiose and xylo-oligosaccharide mixtures.

For viscosity measurements, 2 solutions were made comprising a 1:2 and a 2:1 ratio of cellobiose and xylo-oligosaccharides. The samples were tested using a Brookfield HDB VE roto-viscometer using standard testing procedures, a 400 mL sample is taken in a tall-form beaker to ensure that no container effects occur. The instrument is operated as per the manufacturer's instructions with respect to ranges. Roto-viscometry using spindle code 61, spindle speed 100 rpm, and at 22° C. (see FIG. 13).

Figure 14:
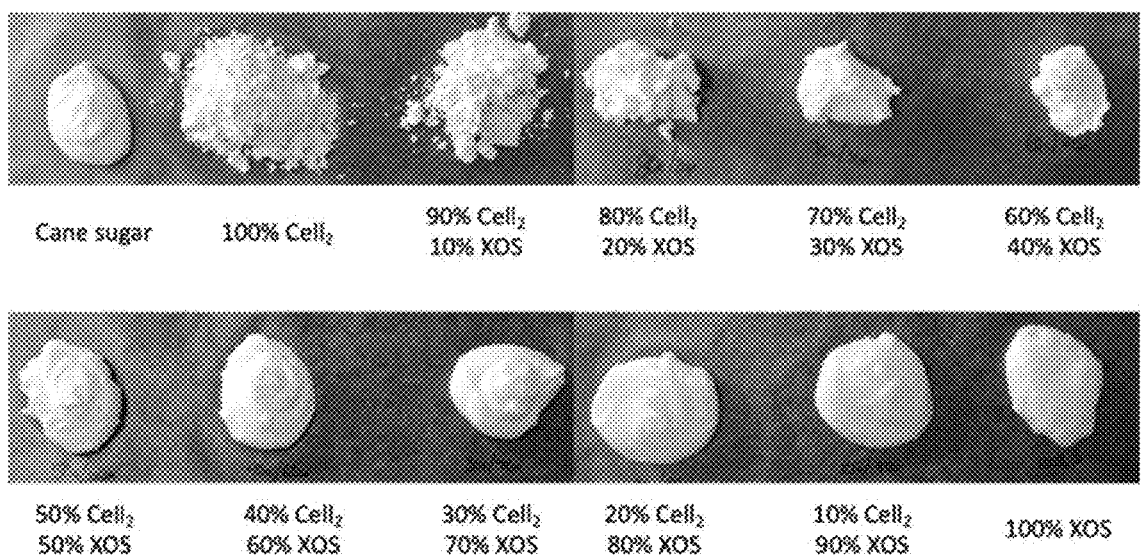
FIG. 14 shows examples of cream cheese icing made using oligosaccharide mixtures.

Example 17—Cream Cheese Icing Made Using Oligosaccharide Mixtures 7 g butter and 21 g cream cheese were combined. 50 g icing sugar or premade $Cell_2$/XOS mixture were mixed in. Results are shown in FIG. 14.

When $Cell_2$ is used alone the structure of the icing is very dry and crumbly and as a result it is unable to hold a proper structure of icing and function as icing properly. As $Cell_2$ is replaced by XOS in 10% increments the structure becomes increasingly better able to stick together. Between about 50:50 and about 20:80 $Cell_2$:XOS w/w ratios the texture of the icing compositions is similar to that when using sugar and has a sturdy thick cream cheese icing consistency. Between about 50:50 and about 20:80 $Cell_2$:XOS w/w ratios the surface appearance of the icing compositions is similar to that when using sugar and has a smooth, shiny surface that retains structure like it does when sugar is used. As the mixture approaches and reaches 100% XOS the texture becomes increasingly thick and lumpy and/or crystallised as the XOS fails to incorporate properly into the icing, and the surface is unable to hold the whipped appearance of icing. Acceptable $Cell_2$:XOS w/w ratio ranges for cream cheese icing include 50:50 to 20:80 with optimal being 30:70.

Example 18—Meringue Made Using Oligosaccharide Mixtures

The product was made as follows:
1. Whisk 30 g egg whites until foamy.
2. Add 30 g sugar or premade $Cell_2$/XOS mixture half at a time.
3. Whisk to stiff peaks.

Figure 15:
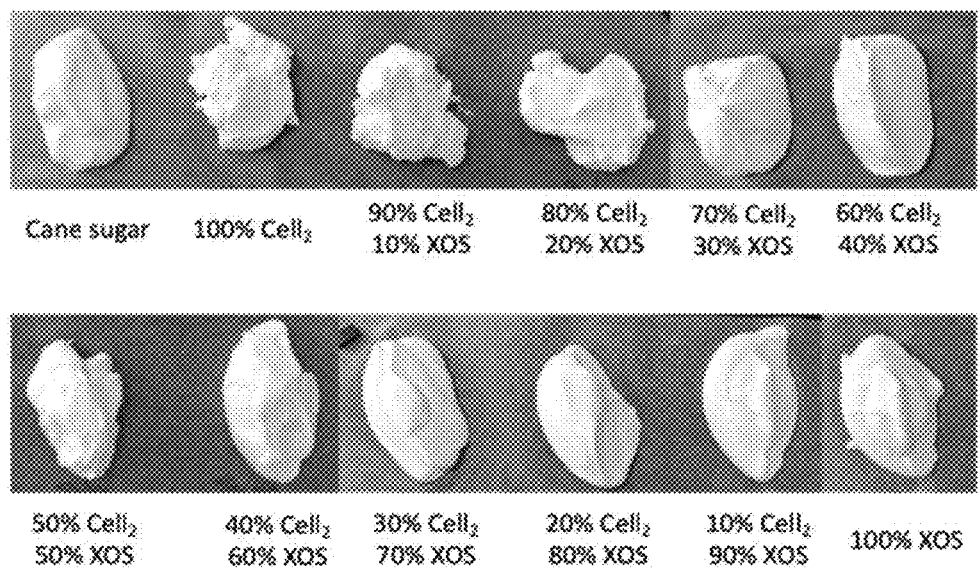
FIG. 15 shows examples of meringue made using oligosaccharide mixtures.

Results are shown in FIG. 15. When $Cell_2$ is used alone the structure of the meringue is dry, dull and brittle and as a result it is unable to hold a proper structure of meringue and function as meringue properly. As $Cell_2$ is replaced by XOS in 10% increments the structure becomes increasingly better able to stick together. Between about 70:30 and about 10:90 $Cell_2$:XOS w/w ratios the texture of the meringue composition is similar to that when using sugar and has a sturdy thick meringue consistency. Between about 70:30 and about 10:90 $Cell_2$:XOS w/w ratios the surface appearance of the meringue compositions is similar to that when using sugar and has a smooth, shiny surface that retains structure like it does when sugar is used. As the mixture approaches and reaches 100% XOS the texture becomes increasingly thin and the surface becomes shinier. Acceptable $Cell_2$:XOS w/w ratio ranges for meringue include 70:30 to 10:90 with optimal being 30:70

Example 19: Chocolate Chip Muffin/Cupcakes Made Using Oligosaccharide Mixtures

The products were made as follows:
1. Combine 64 g flour, ¾ tsp baking powder, ⅛ tsp salt, and 25 g sugar or premade Cell2/XOS mixture.
2. Separately combine 45 g milk, 17 g sunflower oil, and 13 g egg.
3. Mix the wet ingredients into the dry.
4. Fold in 30 g chocolate chips.
5. Weigh out 55 g batter per muffin.
6. Bake 12 minutes in a preheated oven at 170° C.

Figure 16:
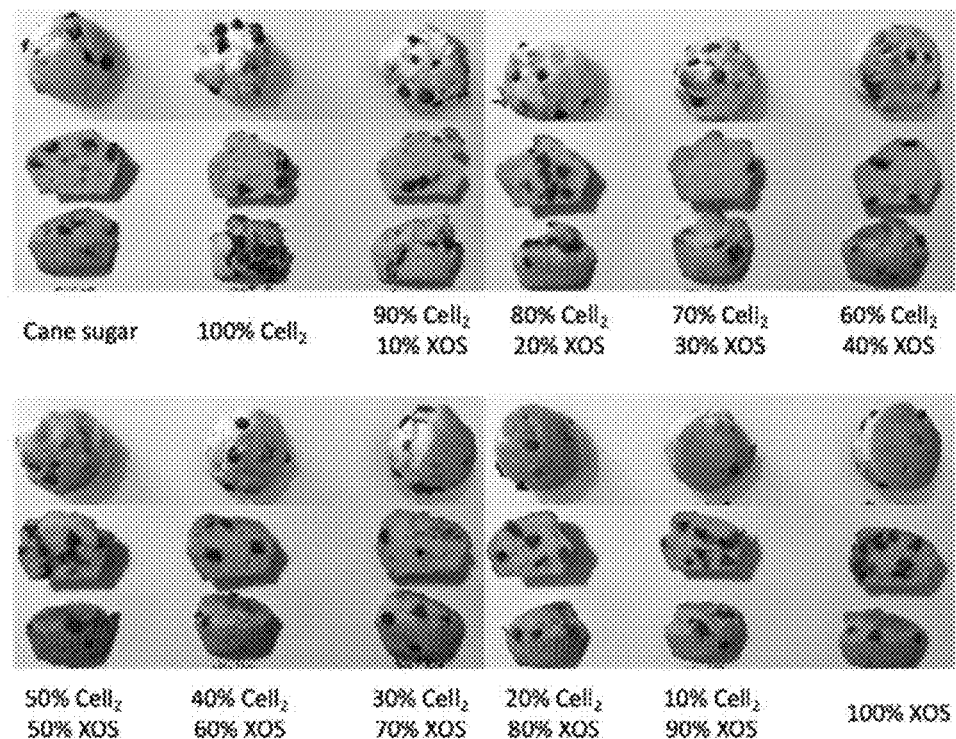
FIG. 16 shows examples of chocolate chip muffin or cupcakes made using oligosaccharide mixtures.

Results are shown in FIG. 16. When $Cell_2$ is used alone the structure of the muffin is dry, dense, lumpy and readily crumbles and as a result it is unable to hold a proper structure of muffin and function as muffin properly. The surface browns unevenly and wrinkles far more and is far lumpier than with sugar. As $Cell_2$ is replaced by XOS in 10% increments the structure becomes increasingly better able to stick together. Between about 90:10 and about 10:90 $Cell_2$:XOS w/w ratios the texture of the muffin compositions is similar to that when using sugar and has a soft, cakey, chewy consistency, is able to hold moisture better and has a more sugar-like rise and colour. Between about 90:10 and about 10:90 $Cell_2$:XOS w/w ratios the surface appearance of the muffin compositions is similar to that when using sugar: it browns more evenly and has a more cake-like wrinkling structure.

As the mixture approaches and reaches 100% XOS the texture becomes increasingly thick and dense, and the surface becomes excessively brown and does not display the typical wrinkled/cracked structure of a muffin surface, instead forming a solid film-like surface. Acceptable $Cell_2$:XOS w/w ratio ranges for muffins/cupcakes include 90:10 to 10:90 with optimal being between 60:40 and 40:60.

Example 20: Peanut Butter Cookies Made Using Oligosaccharide Mixtures

The products were made as follows:
1. Cream 14 g butter and 23 g sugar or premade Cell2/XOS mixture.
2. Add 7 g egg and 0.7 g vanilla extract and combine thoroughly.
3. Add 15 g peanut butter and mix until combined.
4. Mix in 20 g flour, 0.35 g baking powder, and 0.35 g baking soda.
5. Weigh out 20 g of dough, roll into a ball.
6. Bake 9 minutes in a preheated oven at 160° C.

Figure 17:
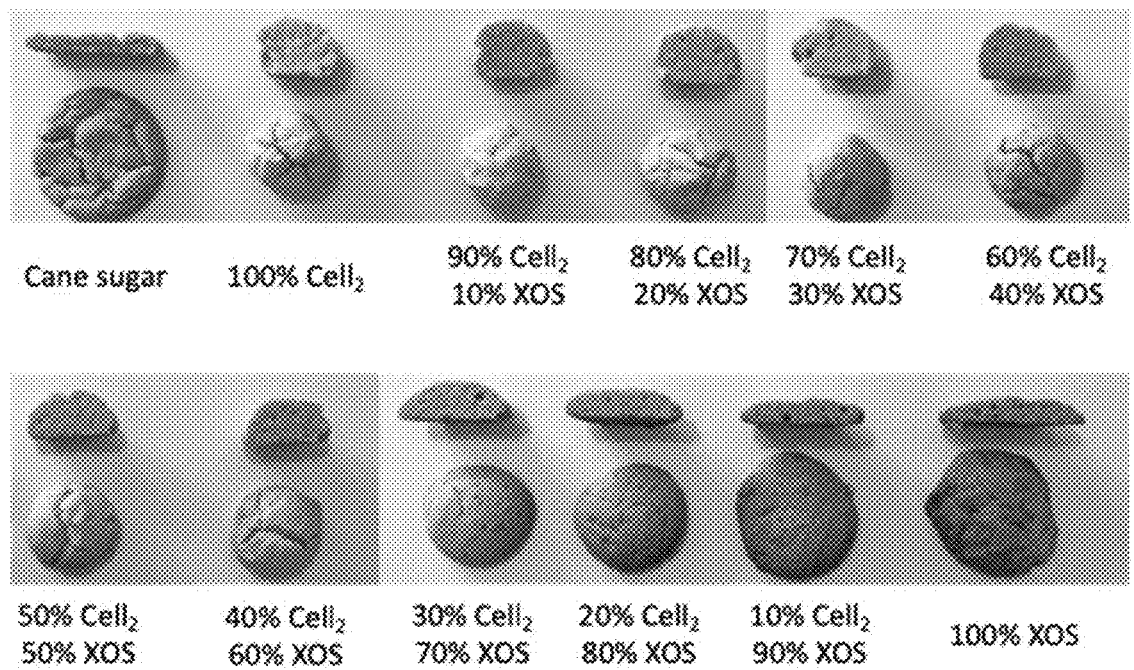
FIG. 17 shows examples of peanut butter cookie made using oligosaccharide mixtures.

Results are shown in FIG. 17. When $Cell_2$ is used alone the structure of the cookie is very dry and dense as $Cell_2$ does not incorporate well into the dough. As a result the composition is unable to hold a proper structure of a cookie. When $Cell_2$ is used alone the surface is also too light-colored and does not brown enough. As $Cell_2$ is replaced by XOS in 10% increments the structure becomes increasingly better able to stick together. Between about 30:70 and about 10:90 $Cell_2$:XOS w/w ratios the texture of the cookie compositions is similar to that when using sugar and has a chewy, crumbly consistency. Between about 30:70 and about 10:90 $Cell_2$:XOS w/w ratios the surface appearance of the cookie compositions is similar to that when using sugar and has a cracked, wrinkled, evenly-browned surface that retains structure like it does when sugar is used. As the mixture approaches and reaches 100% XOS the surface becomes too dark and pitted, the shape is unevenly distributed and partly burns at the edges, and the texture becomes increasingly thick, lumpy and granular as the XOS fails to incorporate properly into the cookie and sometimes forms clumps that will not readily break apart. Acceptable $Cell_2$:XOS w/w ratio ranges for cookies include about 30:70 to about 10:90 with optimal being between about 20:80 and about 10:90.

Example 21: Jams Made Using Oligosaccharide Mixtures

Products were made as follows:
1. Combine 60 g raspberries and 30 g sugar or premade $Cell_2$/XOS mixtures in a small sauce pan.
2. Cook over medium low heat until it reaches thread stage.

Figure 18:
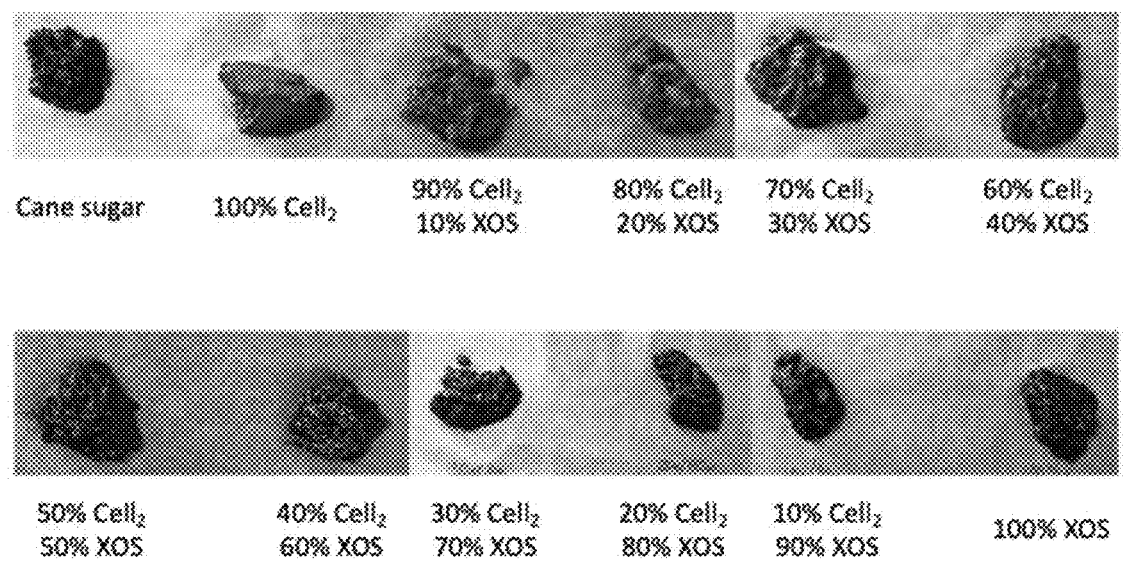
FIG. 18 shows examples of jam made using oligosaccharide mixtures.

Results are shown in FIG. 18. When $Cell_2$ is used alone the structure of the jam is dry, sandy, dull, dense and solid and so unable to hold a proper structure of jam and function as jam properly.

As $Cell_2$ is replaced by XOS in 10% increments the structure becomes increasingly better able to stick together and hold moisture. Between about 50:50 and about 10:90 $Cell_2$:XOS w/w ratios the texture of the jam compositions is similar to that when using sugar and has a moist, smooth, and soft consistency that easily flows and can be spread. Between about 50:50 and about 10:90 $Cell_2$:XOS w/w ratios the surface appearance of the jam compositions is similar to that when using sugar and has a smooth, shiny surface like it does when sugar is used. As the mixture approaches and reaches 100% XOS the texture becomes increasingly thin and translucent and the XOS can fail to incorporate properly into the jam and sometimes forms clumps that will not readily break apart. Acceptable $Cell_2$:XOS w/w ratio ranges for jam icing include about 50:50 to about 10:90 with optimal being about 30:70 to about 10:90.

Example 22: Ice Cream Made Using Oligosaccharide Mixtures

A recipe that can be used to make such products is as follows:
1. Place ice cream maker insert into the freezer at least one day ahead of making ice cream.
2. Heat 284 g double cream, 300 g full fat milk, and 57.5 g sugar or premade $Cell_2$/XOS mixture in a medium sauce pan until just steamy.
3. Whisk together 60 g egg yolks and 57.5 g sugar or premade Cell2/XOS mixture until lightened in colour.
4. Pour about ⅓ of the steamy cream mixture into the egg mixture. Combine and pour back into the sauce pan.
5. Cook, stirring constantly until the mixture thickens enough to coat the back of a spoon.
6. Chill custard overnight.
7. Pour custard into ice cream machine and churn for 10-30 minutes.
8. Scoop into a container and freeze at least 3 hours before serving.

100% $Cell_2$ is expected to be too dull, thick and grainy and 100% XOS is expected to be shiny, lumpy with crystallised XOS and too liquid. A combination of the two would be expected to hold well, be smooth, and have the proper amount of shine.

Example 23: Chocolate Made Using Oligosaccharide Mixtures

A recipe that can be used to make such products is as follows:
1. Combine 700 g cocoa mass, 50 g cocoa butter and 250 g sugar or premade $Cell_2$/XOS mixture with mild heat until sugar or premade $Cell_2$/XOS mixture melts and everything is well combined.
2. Temper the chocolate and use as needed.

100% $Cell_2$ is expected to be dry, crumbly, and dull. 100% XOS is expected to be runny, shiny, and crystallised/lumpy. A combination of the two is expected to result in shiny chocolate with the proper density and texture.

Example 24: Pate De Fruits Made Using Oligosaccharide Mixtures

A recipe that can be used to make such products is as follows:
1. Bring 500 g fruit puree to boil.
2. Combine 100 g sugar or premade $Cell_2$/XOS mixture with 12.5 g pectin powder.
3. Add the dry mix to the puree and bring to boil whisking continually.
4. Add 200 g sugar or premade $Cell_2$/XOS mixture and bring to softball stage (112° C.-116° C.).
5. Remove from heat and add 5 g lemon juice.
6. Pour into paper lined mould.
7. Allow to set before removing from the pan.
8. Cut into pieces.

100% $Cell_2$ is expected to be dull, dry, opaque, and crumbly. 100% XOS is not expected to set properly and will be shiny and translucent (neither will reach temperatures). A combination of the two is expected to result in a pate de fruits that is soft, chewy/sticky, and slight translucent.

Example 25: Soft Caramels Made Using Oligosaccharide Mixtures

A recipe that can be used to make such products is as follows:
1. In a sauce pan cook 250 g sugar or premade $Cell_2$/XOS mixture, 250 g double cream, and 125 g glucose to 112° C.
2. Remove from heat and add 65 g soft butter.
3. Cook further to firm ball stage (118-120° C.).
4. Pour into a paper lined fudge tray and allow to cool.
5. Once cold cut into bite sized pieces.

100% $Cell_2$ is expected to be dry, dull, and crumbly. 100% XOS is not expected to set properly and will be shiny and crystallised/lumpy (neither will reach temperatures). A combination of the two should result in a soft chewy caramel that is slightly shiny.

Example 26: Marshmallows Made Using Oligosaccharide Mixtures

A recipe that can be used to make such products is as follows:
1. Bloom 25 g gelatine in 180 g of water in a bowl of a mixer.
2. Once the gelatine is bloomed, heat the over a bain-marie to dissolve the gelatin.
3. Heat 180 g of water, 300 g sugar or premade $Cell_2$/XOS mixture, and 150 g glucose to 116° C., remove and stir in the remaining 60 g of glucose.
4. Pour the syrup into the gelatine mixture and whisk till cooled and thickened. Transfer to a piping bag.
5. Sieve 500 g icing sugar and 500 g corn flour together and divide onto trays.
6. Pipe marshmallow mix onto icing sugar mixture.
7. Allow to set.
8. Cut into bite sized pieces and dust-off excess sugar.

100% $Cell_2$ is expected to be dry, dull, and crumbly. 100% XOS is expected to be shiny but will not set (neither will reach temperatures). A combination of the two may result in a properly set marshmallow that has the correct aeration and chewy texture.

TABLE 4

Sequence listings

| Name | SEQ ID | Sequence | | | | |
|---|---|---|---|---|---|---|
| LPMO: AA9 LPMO from *Podospora anserine* | 1 | MKGLLSVAAL | SLAVSEVSAH | YIFQQLSTGS | TKHGVFQYIR | QNTNYNSPVT DLSSNDLRCN |
| | | EGGASGANTQ | TVTVRAGDSF | TFHLDTPVYH | QGPVSVYLSK | APGSASSYDG SGTWFKIKDW |
| | | GPTFPGGQWT | LAGSYTAQLP | SCITDGEYLL | RIQSLGIHNP | YPAGTPQFYI SCAQIKVTGG |
| | | GSVNPSGVAI | PGAFKATDPG | YTANIYSNFN | SYTVPGPSVF | SCGSNGGGSS PVEPQPQPTT |
| | | TLVTSTRAPV | ATQPAGCAVA | KWGQCGGNGW | TGCTTCAAGS | TCNTQNAYYH QCV |

TABLE 4-continued

Sequence listings

| Name | SEQ ID | Sequence |
|---|---|---|
| Lichenase GH16 Lichenase from *Bacillus subtilis* subsp. subtilis str. 168 | 2 | MPYLKRVLLL LVTGLFMSLF AVTATASAQT GGSFFDPFNG YNSGFWQKAD GYSNGNMFNC TWRANNVSMT SLGEMRLALT SPAYNKFDCG ENRSVQTYGY GLYEVRMKPA KNTGIVSSFF TYTGPTDGTP WDEIDIEFLG KDTTKVQFNY YTNGAGNHEK IVDLGFDAAN AYHTYAFDWQ PNSIKWYVDG QLKHTATNQI PTTPGKIMMN LWNGTGVDEW LGSYNGVNPL YAHYDWVRYT KK |
| Xylanase: GH5 Arabinoxylanase from *Ruminiclostridium thermocellum* | 3 | MGASIKTSIK IRTVAFVSII AIALSILSFI PNRAYASPQR GRPRLNAART TFVGDNGQPL RGPYTSTEWT AAAPYDQIAR VKELGFNAVH LYAECFDPRY PAPGSKAPGY AVNEIDKIVE RTRELGLYLV ITIGNGANNG NHNAQWARDF WKFYAPRYAK ETHVLYEIHN EPVAWGPPYS SSTANPPGAV DMEIDVYRII RTYAPETPVL LFSYAVFGGK GGAAEALKDI RAFNKAVFGN ENAVWTNEAV AFHGYAGWQE TTIAVEELLK AGYPCFMTEY AGGAWGSGMG GLDVELTYEL ERLGVSWLTF QYIPPTGVSD DVTKPEYFSA LVENSGLSWT PDYGNWPAAR GVYGNGGLAR ETATWINNPL TGTTRIEAED FDWGGNGVSY YDTDSVNVGG QYRPDEGVDI EKTSDTGGGY NVGWISEGEW LEYTIRVRNP GYYNLSLRVA GISGSRVQVS FGNQDKTGVW ELPATGGFQT WTTATRQVFL GAGLQKLRIN ALSGGFNLNW IELSPISTGT IPDGTYKFLN RANGKTLQEV TGNNSIITAD YKGITEQHWK IQHIGGGQYR ISSAGRGWNW NWWMGFGTVG WWGTGSSTCF IISPTGDGYY RIVLVGDGTN LQISSGDPSK IEGKAFHGGA NQQWAILPVS APAFPTGLSA VLDSSGNTAN LTWNAAPGAN SYNVKRSTKS GGPYTTIATN ITSTNYTDTG VATGTKYYYV VSAVSNGVET LNSAEAILQY PKLTGTVIGT QGSWNNIGNT IHKAFDGDLN TFFDGPTANG CWLGLDFGEG VRNVITQIKF CPRSGYEQRM IGGIFQGANK EDFSDAVTLF TITSLPGSGT LTSVDVDNPT GFRYVRYLSP DGSNGNIAEL QFFGTPAGEE NDDVHLGDIN DDGNINSTDL QMLKRHLLRS IRLTEKQLLN ADTNRDGRVD STDLALLKRY ILRVITTL |
| Xylanase: GH5 Xylanase from *Gonapodya* prolifera | 4 | MARLSSLIAL VLAFVAVSAP ALAARGRPRL NGKTFVADSG VPLRGPFTST EWTPAVPAAN IANMRNYNFN AIHLYAETFD PNYPAAGSQK PGYAATRVDQ IVAATKAANM YVVIVLANGA NNGKFNLNYA KDFWSFYAAR YKNETHVIYE RINEPVQWGP PYISSTQSPG AVSMNADCYK IIRAVAPDTP VLLFTYASIG GGSSAAGAVK DAQSFNTAVF GNANAQWTNE AIAIHGYWGA QGASDAAKAL NAAGFSVVLT EFAAATSPTS PNGGQDTVLT GFMEQQGVSW LTFLHVPPTG VSGDVTDPNQ YTNRMTAAGI GFDRDPGLNA VGGGQAAPVP VPAPAPVPSP VPAPVPAVPA VRTTTARPAP SPSPVPAPVP APAPVPAPVP APVPAPVPAP VPAPVPASPA ATTTRRHRTR PPRTTTAPAV PAPPPAATPK VCG |
| Xylanase: GH30 xylanase from *Dickeya chrysanthemi* | 5 | MNGNVSLWVR HCLHAALFVS ATAGSFSVYA DTVKIDANVN YQIIQGFGGM SGVGWINDLT TEQINTAYGS GVGQIGLSIM RVRIDPDSSK WNIQLPSARQ AVSLGAKIMA TPWSPPAYMK SNNSLINGGR LLPANYSAYT SHLLDFSKYM QTNGAPLYAI SIQNEPDWKP DYESCEWSGD EFKSYLKSQG SKFGSLKVIV AESLGFNPAL TDPVLKDSDA SKYVSIIGGH LYGTTPKPYP LAQNAGKQLW MTEHYVDSKQ SANNWTSAIE VGTELNASMV SNYSAYVWWY IRRSYGLLTE DGKVSKRGYV MSQYARFVRP GALRIQATEN PQSNVHLTAY KNTDGKMVIV AVNTNDSDQM LSLNISNANV TKFEKYSTSA SLNVEYGGSS QVDSSGKATV WLNPLSVTTF VSK |
| Xylanase: GH30 xylanase from *Bacillus subtilis* subsp. *subtilis* str. 168 | 6 | MIPRIKKTIC VLLVCFTMLS VMLGPGATEV LAASDVTVNV SAEKQVIRGF GGMNHPAWAG DLTAAQRETA FGNGQNQLGF SILRIHVDEN RNNWYKEVET AKSAVKHGAI VFASPWNPPS DMVETFNRNG DTSAKRLKYN KYAAYAQHLN DFVTFMKNNG VNLYAISVQN EPDYAHEWTW WTPQEILRFM RENAGSINAR VIAPESFQYL KNLSDPILND PQALANMDIL GTHLYGTQVS QFPYPLFKQK GAGKDLWMTE VYYPNSDTNS ADRWPEALDV SQHIHNAMVE GDFQAYVWWY IRRSYGPMKE DGTISKRGYN MAHFSKFVRP GYVRIDATKN PNANVYVSAY KGDNKVVIVA INKSNTGVNQ NFVLQNGSAS NVSRWITSSS SNLQPGTNLT VSGNHFWAHL PAQSVTTFVVNR |
| Xylanase: GH30 Xylanase from *Bacteroides ovatus* | 7 | MKNITLLFCL FLANILLGAC SGGEDEKKEM DEGKGAYALF LKKSITVSTG ESQTDVVVEW AKTSWEITLG EGDIVKSVTP TSGGSNTGEK QYTKVRVSCG ANSTMKKRTQ TIHLFDKTNE TTVDLLVEQE PPFKSVLTLV DPSVKYQPVV GFGGMYNPKI WCGDNLISAS QLDKMYGAGG LGYSILRLMI YPNESDWSAD VEAAKAAQAN GAIIFACPWD CTDALADKIT VNGKEMKHLK KENYEAYANH LIRYVTFMKE KGVNLYAISV QNEPDMEFTY WTPSEVVDFV KQYGARIRET GVKLMSPEAC GMQPEYTDPI INNAEAFAQT DILAGHLYQG FTDLSSGYVK NRHDYICGVY SRIQGKTWWM TEHLFNDGEN SDDSSKWEFL KWQYSLNHLG KEIHMCMEGY CSAYIWYLK RFYGLMGDTD KRSPTSEGEI TKNGYIMAHY AQYATETTRI KVVTNNEEVC ATAYWDEKTG EVTIVLLNLN GASQWLEIPL AGIKKASAVE TNETKNMEVI DTGLMESAEG ITVLLSANSI TSVRLTF |

TABLE 4-continued

Sequence listings

| Name | SEQ ID | Sequence |
|---|---|---|
| Xyloglucanase: GH5 Xyloglucanase from *Bacteroides ovatus* | 8 | MEKQSFSDGL FSPLGIKRVI FMLVLLTTSF ISCSNSDEKG GSLEVAQEYR NLEFDARGSR QTIQIDGPAE WHISTSESWC KSSHTIGEGK QYVNITVEAN DTQKERTATV TVSASGAPDI LINVKQSLYS VPAYDEYLAP DNTGMRDLTS MQLSALMKAG VNVGNTFEAV IVGNDGSLSG DETCWGNPTP NKVLFEGLKA AGFDVVRLPV AYSHQFEDAA TYKIKSAWMD KVEAAVKAAL DAGLYVIINI HWEGGWLNHP VDANKEALDE RLEAMWKQIA LRFRDYDDRL LFAGTNEVNN DDANGAQPTE ENYRVQNGFN QVFVNTVRAT GGRNHYRHLI VQAYNTDVAK AVAHFTMPLD IVQNRIFLEC HYYDPYDFTI MPNDENFKSQ WGAAFAGGDV SATGQEGDLE ATLSSLNVFL NNNVPVLIGE YGPTLRDQLT GEALENHLKS RNDYLEYVVK TCVKNKLVPL YVVDAGYTEKL FDRTTGQPHN AASIAALMKG LN |
| Xyloglucanase: GH74 Xyloglucanase from *Trichoderma reesei* | 9 | MKVSRVLALV LGAVLPAHAA FSWKNVKLGG GGGFVPGILF HPKTKGVAYA RTDIGGLYRL NADDSWTAVT DGIADNAGWH NWGIDAVALD PQDDQKVYAA VGMYTNSWDP SNGAIIRSSD RGATWSFTNL PFKVGGNMPG RGAGERLAVD PANSNILYFG ARSGNGLWKS TDGGVTFSKV SSFTATGTYL PDPSDSNGYN SDKQGLMWVT FDSTSSTTGG ATSRIFVGTA DNITASVYVS TNAGSTWSAV PGQPGKYFPH KAKLQPAEKA LYLTYSDGTG PYDGTLGSVW RYDIAGGTWK DITPVSGSDL YFGFGGLGLD LQKPGTLVVA SLNSWWPDAQ LFRSTDSGTT WSPIWAWASY PTETYYYSIS TPKAPWIKNN FLDVTSESPS DGLIKRLGWM LESLELDPTD SNHWLYGTGM TLFGGHDLTN WDTRHNVSLQ SLADGLEEFS VQDLASAPGG SELLAAVGDD NGFTFASRND LGTSPQTVWA TPTWATSTSV DYAGNSVKSV VRVGNTAGTQ QVAISSDGGA TWSLDYAADT SMNGGTVAYS ADGDTLLWST ASSGVQRSQF QGSFASVSSL PAGAVIASDK KTNSVFYAGS GSTFYVSKDT GSSFTRGPKL GSAGTIRDIA AHPTTAGTLY VSTDVGIFRS TDSGTTFGQV STALTNTYQL ALGVGSGSNW NLYAFGTGPS GARLYASGDS GASWTDIQGS QGFGSIDSTK VAGSGSTAGQ VYVGTNGRGV FYAQGTVGGG TGGTSSSTKQ SSSSTSSASS STTLRSSVVS TTRASTVTSS RTSSAAGPTG SGVAGHYAQC GGIGWTGPTQ CVAPYVCQKQ NDYYYQCV |
| Cellobiohydrolase: GH7 Cel7A cellobiohydrolase from *Trichoderma reesei* | 10 | MYRKLAVISA FLATARAQSA CTLQSETHPP LTWQKCSSGG TCTQQTGSVV LDANWRWTHA TNSSTNCYDG NTWSSTLCPD NETCAKNCCL DGAAYASTYG VTTSGNSLSI GFVTQSAQKN VGARLYLMAS DTTYQEFTLL GNEFSFDVDV SQLPCGLNGA LYFVSMDADG GVSKYPTNTA GAKYGTGYCD SQCPRDLKFL NGQANVEGWE PSSNNANTGI GGHGSCCSEM DIVVEANSIE ALTPHPCTTV GQEICEGDGC GGTYSDNRYG GTCDPDGCDW NPYRLGNTSF YGPGSSFTLD TTKKLTVVTQ FETSGAINRY YVQNGVTFQQ PNAELGSYSG NELNDDYCTA EEAEFGGSSF SDKGGLTQFK KATSGGMVLV MSLWDDYYAN MLWLDSTYPT NETSSTPGAV RGSCSTSSGV PAQVESQSPN AKVTFSNLKF GPIGSTGNPS GGNPPGGNRG TTTTRRPATT TGSSPGPTQS HYGQCGGIGY SGPTVCASGT TCQVLNPYYS QCL |
| Cellobiohydrolase: GH6 Cel6A cellobiohydrolase from *Trichoderma reesei* | 11 | MIVGLLTTLA TLATLAASVP LEERQACSSV WGQCGGQNWS GPTCCASGST CVYSNDYYSQ CLPGAASSSS STRAASTTSR VSPTTSRSSS ATPPPGSTTT RVPPVGSGTA TYSGNPFVGV TPWANAYYAS EVSSLAIPSL TGAMATAAAA VAKVPSFMWL DTLDKTPLME QTLADLRTAN KNGGNYAGQF VVYDLPDRDC AALASNGEYS IADGGVAKYK NYLDTIRQIV VEYSDLRTLL VIEPDSLANL VTNLGTPKCA NAQSAYLECI NYAVTQLNLP NVAMYLDAGH AGWLGWPANQ DPAAQLFANV YKNASSPRAL RGLATNVANY NGWNITSPPS YTQGNAVYNE KLYIFIALGPL LANHGWSNAF FITDQGRSGK QPTGQQQWGD WCNVIGTGFG LRPSANTGDS LLDSFVWVKP GGECDGTSDS SAPRFDSHCA LPDALQPAPQ AGAWFQAYFV QLLTNANPSF L |
| Endoglucanase A eg1A- *Aspergillus niger* GH12 | 12 | MKLPVTLAML AATAMGQTMC SQYDSASSPP YSVNQNLWGE YQGTGSQCVY VDKLSSSGAS WHTEWTWSGG EGTVKSYSNS GVTFNKKLVS DVSSIPTSVE WKQDNTVNVA DVAYDLFTAA NVDHATSSGD YELMIWLARY GNIQPIGKQI ATATVGGKSW EVWYGSTTQA GAEQRTYSFV SESPINSYSG DINAFFSYLT QNQGFPASSQ YLINLQFGTE AFTGGPATFT VDNWTASVN |
| *Aspergillus niger* Endo-β-1,4-glucanase GH5, CBM1 | 13 | MRISNLIVAA SAASMVSALP SRQMKKRDSG FKWVGTSESG AEFGSALPGT LGTDYTWPET SKIQVLRNKG MNIFRIPFLM ERLTPDGLTS SFASTYLSDL KSTVEFVTNS GAYAVLDPHN YGRFDGSIIT TSDFKTWWK NVATEFADND KVIFDTNNEY HDMEQSLVLD LNQAAINGIR AAGATTQYIF VEGNAYTGAW DWTTYNDNLS GLTDSEDKII YEMFIQYLDSD SSGTSETCVS STIGQERLEK ATEWLKTNNK QGIVGEFAGG VNSVCEEAVE GMLAYMSENS DVWVGASWWS AGPWWGTMY SLEPTDGTAY STYLPILEKY FPSGDASASS SASVSVAAAT STASTTTAAF EQTTTPATQG PSATNSAGEV NQYYQCGGIN WTGPTVCASP YTCKVQNDYY YQCVAE |

TABLE 4-continued

Sequence listings

| Name | SEQ ID | Sequence |
|---|---|---|
| *Aspergillus niger* Endo-β-1,4-glucanase B GH5 | 14 | MKFQSTLLLA AAAGSALAVP HGSGHKKRAS VFEWFGSNES GAEFGTNIPG VWGTDYIFPD PSTISTLIGK GMNFFRVQFM MERLLPDSMT GSYDEEYLAN LTTVVKAVTD GGAHALIDPH NYGRYNGEII SSTSDFQTFW QNLAGQYKDN DLVMFDTNNE YYDMDQDLVL NLNQAAINGI RAAGASQYIF VEGNSWTGAW TWVDVNDNMK NLTDPEDKIV YEMHQYLDSD GSGTSETCVS GTIGKERITD ATQWLKDNKK VGFIGEYAGG SNDVCRSAVS GMLEYMANNT DVWKGASWWA AGPWWGDYIF SLEPPDGTAY TGMLDILETY L |
| GH30 Xylanase from *Trichoderma reesei* | 15 | MKSSISVVLA LLGHSAAWSY ATKSQYRANI KINARQTYQT MIGGGCSGAF GIACQQFGSS GLSPENQQKV TQILFDENIG GLSIVRNDIG SSPGTTILPT CPATPQDKFD YVWDGSDNCQ FNLTKTALKY NPNLYVYADA WSAPGCMKTV GTENLGGQIC GVRGTDCKHD WRQAYADYLV QYVRFYKEEG IDISLLGAWN EPDFNPFTYE SMLSDGYQAK DFLEVLYPTL KKAFPKVDVS CCDATGARQE RNILYELQQA GGERYFDIAT WHNYQSNPER PFNAGGKPNI QTEWADGTGP WNSTWDYSGQ LAEGLQWALY MHNAFVNSDT SGYTHWWCAQ NTNGDNALIR LDRDSYEVSA RLWAFAQYFR FARPGSVRIG ATSDVENVYV TAYVNKNGTV AIPVINAAHF PYDLTIDLEG 42 IKKRKLSEYL TDNSHNVTLQ SRYKVSGSSL KVTVEPRAMK TFWLE |
| *Aspergillus niger* Endo-β-1,4-xylanase 1 GH11 | 16 | MKVTAAFAGL LVTAFAAPVP EPVLVSRSAG INYVQNYNGN LGDFTYDESA GTFSMYWEDG VSSDFVVGLG WTTGSSKAIT YSAEYSASGS SSYLAVYGWV NYPQAEYYIV EDYGDYNPCS SATSLGTVYS DGSTYQVCTD TRTNEPSITG TSTFTQYFSV RESTRTSGTV TVANHENFWA QHGFGNSDFN YQVMAVEAWS GAGSASVTIS S |
| GH5 mannanase from *Trichoderma reesei* | 17 | MMMLSKSLLS AATAASALAA VLQPVPRASS FVTISGTQFN IDGKVGYFAG TNCYWCSFLT NHADVDSTFS HISSSGLKVV RVWGFNDVNT QPSPGQIWFQ KLSATGSTIN TGADGLQTLD YVVQSAEQHN LKLIIPFVNN WSDYGGINAY VNAFGGNATT WYTNTAAQTQ YRKYVQAVVS RYANSTAIFA WELGNEPRCN GCSTDVIVQW ATSVSQYVKS LDSNHLVTLG DEGLGLSTGD GAYPYTYGEG TDFAKNVQIK SLDFGTFHLY PDSWGTNYTW GNGWIQTHAA ACLAAGKPCV FEEYGAQQNP CTNEAPWQTT SLTTRGMGGD MFWQWGDTFA NGAQSNSDPY TVWYNSSNWQ CLVKNHVDAI NGGTTTPPPV SSTTTTSSRT SSTPPPPGGS CSPLYGQCGG SGYTGPTCCA QGTCIYSNYW YSQCLNT |
| *Aspergillus niger* Endo-β-1,4-mannanase GH26 | 18 | MFAKLSLLSL LFSSAALGAS NQTLSYGNID KSATPEARAL LKYIQLQYGS HYISGQQDID SWNWVEKNIG VAPAILGSDF TYYSPSAVAH GGKSHAVEDV IQHAGRNGIN ALVWHWYAPT CLLDTAKEPW YKGFYTEATC FNVSEAVNDH GNGTNYKLLL RDIDAIAAQI KRLDQAKVPI LFRPLHEPEG GWFWWGAQGP APFKKLWDIL YDRITRYHNL HNMVWVCNTA DPAWYPGNDK CDIATIDHYP AVGDHGVAAD QYKKLQTVTN NERVLAMAEV GPIPDPDKQA RENVNWAYWM VWSGDFIEDG KQNPNQFLHK VYNDTRVVAL NWEGA |
| *Aspergillus niger* β-mannanase GH5 | 19 | MKLSNALLTL ASLALANVST ALPKASPAPS TSSSAASTSF ASTSGLQFTI DGETGYFAGT NSYWIGFLTD NADVDLVMGH LKSSGLKILR VWGFNDVTSQ PSSGTVWYQL HQDGKSTINT GADGLQRLDY VVSSAEQHDI KLIINFVNYW TDYGGMSAYV SAYGGSGETD FYTSDTMQSA YQTYIKTVVE RYSNSSAVFA WELANEPRCP SCDTSVLYNW IEKTSKFIKG LDADRMVCIG DEGFGLNIDS DGSYPYQFSE GLNFTMNLGI DTIDFGTLHL YPDSWGTSDD WGNGWITAHG AACKAAGKPC LLEEYGVTSN HCSVEGSWQK TALSTTGVGA DLFWQYGDDL STGKSPDDGN TIYYGTSDYQ CLVTDHVAAI GSA |
| *Aspergillus niger* Cellobiohydrolase A GH7 | 20 | MHQRALLFSA LLTAVRAQQA GTLTEEVHPS LTWQKCTSEG SCTEQSGSVV IDSNWRWTHS VNDSTNCYTG NTWDATLCPD DETCAANCAL DGADYESTYG VTTDGDSLTL KFVTGSNVGS RLYLMDTSDE GYQTFNLLDA EFTFDVDVSN LPCGLNGALY FTAMDADGGV SKYPANKAGA KYGTGYCDSQ CPRDLKFIDG QANVDGWEPS SNNDNTGIGN HGSCCPEMDI WEANKISTAL TPHPCDSSEQ TMCEGNDCGG TYSDDRYGGT CDPDGCDFNP YRMGNDSFYG PGKTIDTGSK MTVVTQFITD GSGSLSEIKR YYVQNGNVIA NADSNISGVT GNSITTDFCT AQKKAFGDED IFAEHNGLAG ISDAMSSMVL ILSLWDDYYA SMEWLDSDYP ENATATDPGV ARGTCDSESG VPATVEGAHP DSSVTFSNIK FGPINSTFSA SA |

TABLE 4-continued

Sequence listings

| Name | SEQ ID | Sequence |
|---|---|---|
| *Aspergillus niger* Cellobiohydrolase B GH7, CBM1 | 21 | MSSFQIYRAA LLLSILATAN AQQVGTYTTE THPSLTWQTC TSDGSCTTND GEVVIDANWR<br>WVHSTSSATN CYTGNEWDTS ICTDDVTCAA NCALDGATYE ATYGVTTSGS ELRLNFVTQG<br>SSKNIGSRLY LMSDDSNYEL FKLLGQEFTF DVDVSNLPCG LNGALYFVAM DADGGTSEYS<br>GNKAGAKYGT GYCDSQCPRD LKFINGEANC DGWEPSSNNV NTGVGDHGSC CAEMDVWEAN<br>SISNAFTAHP CDSVSQTMCD GDSCGGTYSA SGDRYSGTCD PDGCDYNPYR LGNTDFYGPG<br>LTVDTNSPFT VVTQFITDDG TSSGTLTEIK RLYVQNGEVI ANGASTYSSV NGSSITSAFC<br>ESEKTLFGDE NVFDKHGGLE GMGEAMAKGM VLVLSLWDDY AADMLWLDSD YPVNSSASTP<br>GVARGTCSTD SGVPATVEAE SPNAYVTYSN IKFGPIGSTY SSGSSSGSGS SSSSSSTTTK<br>ATSTTLKTTS TTSSGSSSTS AAQAYGQCGG QGWTGPTTCV SGYTCTYENA YYSQCL |
| GH3 beta-glucosidase from *Trichoderma reesei* | 22 | MRYRTAAALA LATGPFARAD SHSTSGASAE AVVPPAGTPW GTAYDKAKAA LAKLNLQDKV<br>GIVSGVGWNG GPCVGNTSPA SKISYPSLCL QDGPLGVRYS TGSTAFTPGV QAASTWDVNL<br>IRERGQFIGE EVKASGIHVI LGPVAGPLGK TPQGGRNWEG FGVDPYLTGI AMGQTINGIQ<br>SVGVQATAKH YILNEQELNR ETISSNPDDR TLHELYTWPF ADAVQANVAS VMCSYNKVNT<br>TWACEDQYTL QTVLKDQLGF PGYVMTDWNA QHTTVQSANS GLDMSMPGTD FNGNNRLWGP<br>ALTNAVNSNQ VPTSRVDDMV TRILAAWYLT GQDQAGYPSF NISRNVQGNH KTNVRAIARD<br>GIVLLKNDAN ILPLKKPASI AVVGSAAIIG NHARNSPSCN DKGCDDGALG MGWGSGAVNY<br>PYFVAPYDAI NTRASSQGTQ VTLSNTDNTS SGASAARGKD VAIVFITADS GEGYITVEGN<br>AGDRNNLDPW HNGNALVQAV AGANSNVIVV VHSVGAIILE QILALPQVKA VVWAGLPSQE<br>SGNALVDVLW GDVSPSGKLV YTIAKSPNDY NTRIVSGGSD SFSEGLFIDY KHFDDANITP<br>RYEFGYGLSY TKFNYSRLSV LSTAKSGPAT GAVVPGGPSD LFQNVATVTV DIANSGQVTG<br>AEVAQLYITY PSSAPRTPPK QLRGFAKLNL TPGQSGTATF NIRRRDLSYW DTASQKWVVP<br>SGSFGISVGA SSRDIRLTST LSVA |
| Beta-xylosidase from *Trichoderma reesei* | 23 | MVNNAALLAA LSALLPTALA QNNQTYANYS AQGQPDLYPE TLATLTLSFP DCEHGPLKNN<br>LVCDSSAGYV ERAQALISLF TLEELILNTQ NSGPGVPRLG LPNYQVWNEA LHGLDRANFA<br>TKGGQFEWAT SPPMPILTTA ALNRTLIHQI ADIISTQARA FSNSGRYGLD VYAPNVNGFR<br>SPLWGRGQET PGEDAFILSS AYTYEYITGI QGGVDPEHLK VAATVKHFAG YDLENWNNQS<br>RLGFDAIITQ QDLSEYYTPQ FLAAARYAKS RSLMCAYNSV NGVPSCANSF FLQTLLRESW<br>GFPEWGYVSS DCDAVYNVFN PHDYASNQSS AAASSLRAGT DIDCGQTYPW HLNESFVAGE<br>VSRGEIERSV TRLYANLVRL GYFDKKNQYR SLGWKDVVKT DAWNISYEAA VEGIVLLKND<br>GTLPLSKKVR SIALIGPWAN ATTQMQGNYY GPAPYLISPL EAAKKAGYHV NFELGTEIAG<br>NSTTGFAKAI AAAKKSDAII YLGGIDNTIE QEGADRTDIA WPGNQLDUK QLSEVGKPLV<br>VLQMGGGQVD SSSLKSNKKV NSLVWGGYPG QSGGVALFDI LS GKRAPAGR LVTTQYPAEY<br>VHQFPQNDMN LRPDGKSNPG QTYIWYTGKP VYEFGSGLFY TTFKETLASH PKSLKFNTSS<br>ILSAPHPGYT YSEQIPVFIF EANIKNSGKT ESPYTAMLFV RTSNAGPAPY PNKWLVGFDR<br>LADIKPGHSS KLSIPIPVSA LARVDSHGNR IVYPGKYELA LNTDESVKLE FELVGEEVTI<br>ENWPLEEQQI KDATPDA |
| Beta-mannosidase from *Trichoderma reesei* | 24 | MARHSIQLDK GWTFRQHQGS SPEWLPVEKV PTQVHMDLLA NKQIPDPFVD LNERAVQWIG<br>YKDWEYQVTF TPEAAQVEDA TRDLVFNGLD TFATVYLNEA KILEAENMFV SYRVNVTDRI<br>KASSENTLRI VFHSAIVRGE ELIKEHPEHN FLVRQTERSR VPVRKAQYNW GWDWGPILMT<br>AGPWKPVALE TYVARIDDVW AQSDVSQDLK TVSGIIFARV AGRPSQDDQV SLTLSLDGKA<br>VFQQTVDVAS AKDGLIKVPF KLEDPKLWYP RGYGSQPRYQ LNADLARKAS DASQIDSLSK<br>LVGPRRAELV QEPDAFGKSF YFRINNVDVF AGGSCWIPAD SYLAGVPPER YHAWAKLIAD<br>GNQVMLRVWG GGVYEEDALI EACDELGILV FHDFQFACAS YPAYPSYLEN LEVEARQQIR<br>RLRTHPSVII WAGNNEDYQV QERYKLDYEF ENKDPESWLK SSFPARYIYE HFLPKLVEEE<br>DPGKIYHPSS PWGDGKPTAD PTVGDIHQWN XPPPPISTQI THTQHPTDHP LHTVWHGTMN<br>KYQEAVNMGG RFVSEFGMEA YPHLSTTRRM ASDPAQLYPG SMVLDAHNKA IGHERRMMSY<br>VVDNFRPRHD LGGYTHLTQV VQSETMRAAY KAWRRQWGKP GARRCGGALV WQLNDCWPTM<br>SWAVVDYRLV KKPAYYAIAR ALRRVDVGVC RTWHDWTQTG AWVDENSGLV TGQVDHTLAA<br>REGIFDVWVV SSDTQPVALD LVVRFISVRT GRDVDPILH SRVVAAANSA TDILQGKTLP<br>PSIPNPEDIT KPFPLAEYDP YVVHATITDA ATGTVIAADT AWPEPIKYLD LSDRGIAFEV<br>SSAGDEVVVS AEKPVKGFVF EEVEGLELSD NGFDVVPGEK QLVKVGGALK AGELLWTCIG<br>ADSASLKIEA SSSLAPR |

TABLE 4-continued

Sequence listings

| Name | SEQ ID | Sequence |
|---|---|---|
| AA9 LPMO from *Trichoderma reesei* | 25 | MIQKLSNLLV TALAVATGVV GHGHINDIVI NGVWYQAYDP TTFPYESNPP IVVGWTAADL<br>DNGFVSPDAY QNPDIICHKN ATNAKGHASV KAGDTILFQW VPVPWPHPGP<br>IVDYLANCNG<br>DCETVDKTTL EFFKIDGVGL LSGGDPGTWA SDVLISNNNT WVVKIPDNLA PGNYVLRHEI<br>IALHSAGQAN GAQNYPQCFN IAVSGSGSLQ PSGVLGTDLY HATDPGVLIN IYTSPLNYII<br>PGPTVVSGLP TSVAQGSSAA TATASATVPG GGSGPTSRTT TTARTTQASS RPSSTPPATT<br>SAPAGGPTQT LYGQCGGSGY SGPTRCAPPA TCSTLNPYYA QCLN |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A sugar substitute comprising:
   at least 50% saccharides by dry weight, wherein said saccharides comprise:
   i) at least 30% by dry weight xylo-oligosaccharides having a degree of polymerization from 2-12 in the saccharides, and
   ii) at least 1% by dry weight polysaccharide in the saccharides,
   wherein the sugar substitute comprises less than 15% monosaccharides by dry weight of the sugar substitute.

2. The sugar substitute of claim 1, wherein said sugar substitute comprises less than 10% monosaccharides by dry weight.

3. The sugar substitute of claim 1, wherein said xylo-oligosaccharides comprise at least 4% w/w xylobiose.

4. The sugar substitute of claim 1, wherein said xylo-oligosaccharides comprise up to 60% w/w xylobiose.

5. The sugar substitute of claim 1, wherein a portion of the xylo-oligosaccharides comprise arabinosyl residues.

6. The sugar substitute of claim 1, wherein said xylo-oligosaccharides have a degree of polymerization from two to five.

7. The sugar substitute of claim 6, wherein the xylo-oligosaccharides comprise at least 2% w/w of xylo-oligosaccharides with a degree of polymerization of 3.

8. The sugar substitute of claim 1, wherein said monosaccharides comprise glucose, xylose, galactose, fucose, fructose, arabinose, or any combination thereof.

9. The sugar substitute of claim 1, wherein said saccharides further comprise a second oligosaccharide.

10. The sugar substitute of claim 9, said second oligosaccharide is a cello-oligosaccharide having a degree of polymerization from two to six.

11. The sugar substitute of claim 10, wherein the cello-oligosaccharides comprise at least 2% w/w of cello-oligosaccharides with a degree of polymerization of 3.

12. The sugar substitute of claim 9, wherein said second oligosaccharide is a manno-oligosaccharide.

13. The sugar substitute of claim 12, said manno-oligosaccharide having a degree of polymerization from two to twelve.

14. The sugar substitute of claim 1, comprising at least 75% saccharides by dry weight.

15. The sugar substitute of claim 1, comprising at least 85% saccharides by dry weight.

16. The sugar substitute of claim 1, wherein said saccharides comprise at least 40% by dry weight of said xylo-oligosaccharides having a degree of polymerization from 2-12.

17. The sugar substitute of claim 1, wherein said saccharides comprise at least 5% by dry weight of a cellulosic polysaccharide.

18. The sugar substitute of claim 1, wherein said saccharides comprise at least 10% by dry weight of a cellulosic polysaccharide.

19. The sugar substitute of claim 1, wherein said saccharides comprise at least 20% by dry weight of a cellulosic polysaccharide.

20. A food product comprising the sugar substitute of claim 1.

* * * * *

SEQUENCE LISTING

<160> NUMBER OF SEQ ID NOS: 25

<210> SEQ ID NO 1
<211> LENGTH: 293
<212> TYPE: PRT
<213> ORGANISM: Podospora anserine

<400> SEQUENCE: 1

Met Lys Gly Leu Leu Ser Val Ala Ala Leu Ser Leu Ala Val Ser Glu
1               5                   10                  15

Val Ser Ala His Tyr Ile Phe Gln Gln Leu Ser Thr Gly Ser Thr Lys
            20                  25                  30

His Gly Val Phe Gln Tyr Ile Arg Gln Asn Thr Asn Tyr Asn Ser Pro
        35                  40                  45

Val Thr Asp Leu Ser Ser Asn Asp Leu Arg Cys Asn Glu Gly Gly Ala
    50                  55                  60

Ser Gly Ala Asn Thr Gln Thr Val Thr Val Arg Ala Gly Asp Ser Phe
65                  70                  75                  80

Thr Phe His Leu Asp Thr Pro Val Tyr His Gln Gly Pro Val Ser Val
                85                  90                  95

Tyr Leu Ser Lys Ala Pro Gly Ser Ala Ser Ser Tyr Asp Gly Ser Gly
            100                 105                 110

Thr Trp Phe Lys Ile Lys Asp Trp Gly Pro Thr Phe Pro Gly Gly Gln
        115                 120                 125

Trp Thr Leu Ala Gly Ser Tyr Thr Ala Gln Leu Pro Ser Cys Ile Thr
    130                 135                 140

Asp Gly Glu Tyr Leu Leu Arg Ile Gln Ser Leu Gly Ile His Asn Pro
145                 150                 155                 160

Tyr Pro Ala Gly Thr Pro Gln Phe Tyr Ile Ser Cys Ala Gln Ile Lys
                165                 170                 175

Val Thr Gly Gly Gly Ser Val Asn Pro Ser Gly Val Ala Ile Pro Gly
            180                 185                 190

Ala Phe Lys Ala Thr Asp Pro Gly Tyr Thr Ala Asn Ile Tyr Ser Asn
        195                 200                 205

Phe Asn Ser Tyr Thr Val Pro Gly Pro Ser Val Phe Ser Cys Gly Ser
    210                 215                 220

Asn Gly Gly Gly Ser Ser Pro Val Glu Pro Gln Pro Gln Pro Thr Thr
225                 230                 235                 240

```
Thr Leu Val Thr Ser Thr Arg Ala Pro Val Ala Thr Gln Pro Ala Gly
                245                 250                 255

Cys Ala Val Ala Lys Trp Gly Gln Cys Gly Gly Asn Gly Trp Thr Gly
            260                 265                 270

Cys Thr Thr Cys Ala Ala Gly Ser Thr Cys Asn Thr Gln Asn Ala Tyr
        275                 280                 285

Tyr His Gln Cys Val
    290

<210> SEQ ID NO 2
<211> LENGTH: 242
<212> TYPE: PRT
<213> ORGANISM: Bacillus subtilis

<400> SEQUENCE: 2

Met Pro Tyr Leu Lys Arg Val Leu Leu Leu Val Thr Gly Leu Phe
 1               5                  10                  15

Met Ser Leu Phe Ala Val Thr Ala Thr Ala Ser Ala Gln Thr Gly Gly
                20                  25                  30

Ser Phe Phe Asp Pro Phe Asn Gly Tyr Asn Ser Gly Phe Trp Gln Lys
            35                  40                  45

Ala Asp Gly Tyr Ser Asn Gly Asn Met Phe Asn Cys Thr Trp Arg Ala
        50                  55                  60

Asn Asn Val Ser Met Thr Ser Leu Gly Glu Met Arg Leu Ala Leu Thr
65                  70                  75                  80

Ser Pro Ala Tyr Asn Lys Phe Asp Cys Gly Glu Asn Arg Ser Val Gln
                85                  90                  95

Thr Tyr Gly Tyr Gly Leu Tyr Glu Val Arg Met Lys Pro Ala Lys Asn
            100                 105                 110

Thr Gly Ile Val Ser Ser Phe Phe Thr Tyr Thr Gly Pro Thr Asp Gly
        115                 120                 125

Thr Pro Trp Asp Glu Ile Asp Ile Glu Phe Leu Gly Lys Asp Thr Thr
    130                 135                 140

Lys Val Gln Phe Asn Tyr Tyr Thr Asn Gly Ala Gly Asn His Glu Lys
145                 150                 155                 160

Ile Val Asp Leu Gly Phe Asp Ala Ala Asn Ala Tyr His Thr Tyr Ala
                165                 170                 175

Phe Asp Trp Gln Pro Asn Ser Ile Lys Trp Tyr Val Asp Gly Gln Leu
            180                 185                 190

Lys His Thr Ala Thr Asn Gln Ile Pro Thr Thr Pro Gly Lys Ile Met
        195                 200                 205

Met Asn Leu Trp Asn Gly Thr Gly Val Asp Glu Trp Leu Gly Ser Tyr
    210                 215                 220

Asn Gly Val Asn Pro Leu Tyr Ala His Tyr Asp Trp Val Arg Tyr Thr
225                 230                 235                 240

Lys Lys

<210> SEQ ID NO 3
<211> LENGTH: 948
<212> TYPE: PRT
<213> ORGANISM: Ruminiclostridium thermocellum
```

-continued

```
<400> SEQUENCE: 3

Met Gly Ala Ser Ile Lys Thr Ser Ile Lys Ile Arg Thr Val Ala Phe
1               5                   10                  15

Val Ser Ile Ile Ala Ile Ala Leu Ser Ile Leu Ser Phe Ile Pro Asn
                20                  25                  30

Arg Ala Tyr Ala Ser Pro Gln Arg Gly Arg Pro Arg Leu Asn Ala Ala
            35                  40                  45

Arg Thr Thr Phe Val Gly Asp Asn Gly Gln Pro Leu Arg Gly Pro Tyr
        50                  55                  60

Thr Ser Thr Glu Trp Thr Ala Ala Pro Tyr Asp Gln Ile Ala Arg
65                  70                  75                  80

Val Lys Glu Leu Gly Phe Asn Ala Val His Leu Tyr Ala Glu Cys Phe
                85                  90                  95

Asp Pro Arg Tyr Pro Ala Pro Gly Ser Lys Ala Pro Gly Tyr Ala Val
            100                 105                 110

Asn Glu Ile Asp Lys Ile Val Glu Arg Thr Arg Glu Leu Gly Leu Tyr
        115                 120                 125

Leu Val Ile Thr Ile Gly Asn Gly Ala Asn Asn Gly Asn His Asn Ala
    130                 135                 140

Gln Trp Ala Arg Asp Phe Trp Lys Phe Tyr Ala Pro Arg Tyr Ala Lys
145                 150                 155                 160

Glu Thr His Val Leu Tyr Glu Ile His Asn Glu Pro Val Ala Trp Gly
                165                 170                 175

Pro Pro Tyr Ser Ser Thr Ala Asn Pro Pro Gly Ala Val Asp Met
            180                 185                 190

Glu Ile Asp Val Tyr Arg Ile Ile Arg Thr Tyr Ala Pro Glu Thr Pro
        195                 200                 205

Val Leu Leu Phe Ser Tyr Ala Val Phe Gly Gly Lys Gly Gly Ala Ala
    210                 215                 220

Glu Ala Leu Lys Asp Ile Arg Ala Phe Asn Lys Ala Val Phe Gly Asn
225                 230                 235                 240

Glu Asn Ala Val Trp Thr Asn Glu Ala Val Ala Phe His Gly Tyr Ala
                245                 250                 255

Gly Trp Gln Glu Thr Thr Ile Ala Val Glu Glu Leu Leu Lys Ala Gly
            260                 265                 270

Tyr Pro Cys Phe Met Thr Glu Tyr Ala Gly Gly Ala Trp Gly Ser Gly
        275                 280                 285

Met Gly Gly Leu Asp Val Glu Leu Thr Tyr Glu Leu Glu Arg Leu Gly
    290                 295                 300

Val Ser Trp Leu Thr Phe Gln Tyr Ile Pro Pro Thr Gly Val Ser Asp
305                 310                 315                 320

Asp Val Thr Lys Pro Glu Tyr Phe Ser Ala Leu Val Glu Asn Ser Gly
                325                 330                 335

Leu Ser Trp Thr Pro Asp Tyr Gly Asn Trp Pro Ala Ala Arg Gly Val
            340                 345                 350

Tyr Gly Asn Gly Gly Leu Ala Arg Glu Thr Ala Thr Trp Ile Asn Asn
        355                 360                 365

Phe Leu Thr Gly Thr Thr Arg Ile Glu Ala Glu Asp Phe Asp Trp Gly
    370                 375                 380

Gly Asn Gly Val Ser Tyr Tyr Asp Thr Asp Ser Val Asn Val Gly Gly
385                 390                 395                 400

Gln Tyr Arg Pro Asp Glu Gly Val Asp Ile Glu Lys Thr Ser Asp Thr
                405                 410                 415
```

```
Gly Gly Gly Tyr Asn Val Gly Trp Ile Ser Glu Gly Glu Trp Leu Glu
                420                 425                 430

Tyr Thr Ile Arg Val Arg Asn Pro Gly Tyr Tyr Asn Leu Ser Leu Arg
                435                 440                 445

Val Ala Gly Ile Ser Gly Ser Arg Val Gln Val Ser Phe Gly Asn Gln
                450                 455                 460

Asp Lys Thr Gly Val Trp Glu Leu Pro Ala Thr Gly Phe Gln Thr
465                 470                 475                 480

Trp Thr Thr Ala Thr Arg Gln Val Phe Leu Gly Ala Gly Leu Gln Lys
                485                 490                 495

Leu Arg Ile Asn Ala Leu Ser Gly Gly Phe Asn Leu Asn Trp Ile Glu
                500                 505                 510

Leu Ser Pro Ile Ser Thr Gly Thr Ile Pro Asp Gly Thr Tyr Lys Phe
                515                 520                 525

Leu Asn Arg Ala Asn Gly Lys Thr Leu Gln Glu Val Thr Gly Asn Asn
                530                 535                 540

Ser Ile Ile Thr Ala Asp Tyr Lys Gly Ile Thr Glu Gln His Trp Lys
545                 550                 555                 560

Ile Gln His Ile Gly Gly Gly Gln Tyr Arg Ile Ser Ser Ala Gly Arg
                565                 570                 575

Gly Trp Asn Trp Asn Trp Trp Met Gly Phe Gly Thr Val Gly Trp Trp
                580                 585                 590

Gly Thr Gly Ser Ser Thr Cys Phe Ile Ile Ser Pro Thr Gly Asp Gly
                595                 600                 605

Tyr Tyr Arg Ile Val Leu Val Gly Asp Gly Thr Asn Leu Gln Ile Ser
                610                 615                 620

Ser Gly Asp Pro Ser Lys Ile Glu Gly Lys Ala Phe His Gly Gly Ala
625                 630                 635                 640

Asn Gln Gln Trp Ala Ile Leu Pro Val Ser Ala Pro Ala Phe Pro Thr
                645                 650                 655

Gly Leu Ser Ala Val Leu Asp Ser Ser Gly Asn Thr Ala Asn Leu Thr
                660                 665                 670

Trp Asn Ala Ala Pro Gly Ala Asn Ser Tyr Asn Val Lys Arg Ser Thr
                675                 680                 685

Lys Ser Gly Gly Pro Tyr Thr Thr Ile Ala Thr Asn Ile Thr Ser Thr
690                 695                 700

Asn Tyr Thr Asp Thr Gly Val Ala Thr Gly Thr Lys Tyr Tyr Tyr Val
705                 710                 715                 720

Val Ser Ala Val Ser Asn Gly Val Glu Thr Leu Asn Ser Ala Glu Ala
                725                 730                 735

Ile Leu Gln Tyr Pro Lys Leu Thr Gly Thr Val Ile Gly Thr Gln Gly
                740                 745                 750

Ser Trp Asn Asn Ile Gly Asn Thr Ile His Lys Ala Phe Asp Gly Asp
                755                 760                 765

Leu Asn Thr Phe Phe Asp Gly Pro Thr Ala Asn Gly Cys Trp Leu Gly
                770                 775                 780

Leu Asp Phe Gly Glu Gly Val Arg Asn Val Ile Thr Gln Ile Lys Phe
785                 790                 795                 800

Cys Pro Arg Ser Gly Tyr Glu Gln Arg Met Ile Gly Gly Ile Phe Gln
                805                 810                 815

Gly Ala Asn Lys Glu Asp Phe Ser Asp Ala Val Thr Leu Phe Thr Ile
                820                 825                 830
```

```
Thr Ser Leu Pro Gly Ser Gly Thr Leu Thr Ser Val Asp Val Asp Asn
            835                 840                 845

Pro Thr Gly Phe Arg Tyr Val Arg Tyr Leu Ser Pro Asp Gly Ser Asn
850                 855                 860

Gly Asn Ile Ala Glu Leu Gln Phe Phe Gly Thr Pro Ala Gly Glu Glu
865                 870                 875                 880

Asn Asp Asp Val His Leu Gly Asp Ile Asn Asp Gly Asn Ile Asn
                885                 890                 895

Ser Thr Asp Leu Gln Met Leu Lys Arg His Leu Leu Arg Ser Ile Arg
            900                 905                 910

Leu Thr Glu Lys Gln Leu Leu Asn Ala Asp Thr Asn Arg Asp Gly Arg
            915                 920                 925

Val Asp Ser Thr Asp Leu Ala Leu Leu Lys Arg Tyr Ile Leu Arg Val
            930                 935                 940

Ile Thr Thr Leu
945

<210> SEQ ID NO 4
<211> LENGTH: 443
<212> TYPE: PRT
<213> ORGANISM: Gonapodya prolifera

<400> SEQUENCE: 4

Met Ala Arg Leu Ser Ser Leu Ile Ala Leu Val Leu Ala Phe Val Ala
1               5                   10                  15

Val Ser Ala Pro Ala Leu Ala Ala Arg Gly Arg Pro Arg Leu Asn Gly
            20                  25                  30

Lys Thr Phe Val Ala Asp Ser Gly Val Pro Leu Arg Gly Pro Phe Thr
            35                  40                  45

Ser Thr Glu Trp Thr Pro Ala Val Pro Ala Ala Asn Ile Ala Asn Met
    50                  55                  60

Arg Asn Tyr Asn Phe Asn Ala Ile His Leu Tyr Ala Glu Thr Phe Asp
65                  70                  75                  80

Pro Asn Tyr Pro Ala Ala Gly Ser Gln Lys Pro Gly Tyr Ala Ala Thr
                85                  90                  95

Arg Val Asp Gln Ile Val Ala Ala Thr Lys Ala Ala Asn Met Tyr Val
            100                 105                 110

Val Ile Val Leu Ala Asn Gly Ala Asn Asn Gly Lys Phe Asn Leu Asn
            115                 120                 125

Tyr Ala Lys Asp Phe Trp Ser Phe Tyr Ala Ala Arg Tyr Lys Asn Glu
        130                 135                 140

Thr His Val Ile Tyr Glu Ile His Asn Glu Pro Val Gln Trp Gly Pro
145                 150                 155                 160

Pro Tyr Ile Ser Ser Thr Gln Ser Pro Gly Ala Val Ser Met Asn Ala
                165                 170                 175

Asp Cys Tyr Lys Ile Ile Arg Ala Val Ala Pro Asp Thr Pro Val Leu
            180                 185                 190

Leu Phe Thr Tyr Ala Ser Ile Gly Gly Gly Ser Ser Ala Ala Gly Ala
        195                 200                 205

Val Lys Asp Ala Gln Ser Phe Asn Thr Ala Val Phe Gly Asn Ala Asn
    210                 215                 220

Ala Gln Trp Thr Asn Glu Ala Ile Ala Ile His Gly Tyr Trp Gly Ala
225                 230                 235                 240

Gln Gly Ala Ser Asp Ala Ala Lys Ala Leu Asn Ala Ala Gly Phe Ser
                245                 250                 255
```

```
Val Val Leu Thr Glu Phe Ala Ala Thr Ser Pro Thr Ser Pro Asn
            260                 265                 270

Gly Gly Gln Asp Thr Val Leu Thr Gly Phe Met Glu Gln Gln Gly Val
        275                 280                 285

Ser Trp Leu Thr Phe Leu His Val Pro Pro Thr Gly Val Ser Gly Asp
    290                 295                 300

Val Thr Asp Pro Asn Gln Tyr Thr Asn Arg Met Thr Ala Ala Gly Ile
305                 310                 315                 320

Gly Phe Asp Arg Asp Pro Gly Leu Asn Ala Val Gly Gly Gln Ala
                325                 330                 335

Ala Pro Val Pro Val Pro Ala Pro Ala Pro Val Pro Ser Pro Val Pro
        340                 345                 350

Ala Pro Val Pro Ala Val Pro Ala Val Arg Thr Thr Ala Arg Pro
        355                 360                 365

Ala Pro Ser Pro Ser Pro Val Pro Ala Pro Val Pro Ala Pro Ala Pro
        370                 375                 380

Val Pro Ala Pro Val Pro Ala Pro Val Pro Ala Pro Val Pro Ala Pro
385                 390                 395                 400

Val Pro Ala Pro Val Pro Ala Ser Pro Ala Thr Thr Arg Arg
                405                 410                 415

His Arg Thr Arg Pro Pro Arg Thr Thr Thr Ala Pro Ala Val Pro Ala
                420                 425                 430

Pro Pro Pro Ala Ala Thr Pro Lys Val Cys Gly
        435                 440

<210> SEQ ID NO 5
<211> LENGTH: 413
<212> TYPE: PRT
<213> ORGANISM: Dickeya chrysanthemi

<400> SEQUENCE: 5

Met Asn Gly Asn Val Ser Leu Trp Val Arg His Cys Leu His Ala Ala
1               5                   10                  15

Leu Phe Val Ser Ala Thr Ala Gly Ser Phe Ser Val Tyr Ala Asp Thr
            20                  25                  30

Val Lys Ile Asp Ala Asn Val Asn Tyr Gln Ile Ile Gln Gly Phe Gly
        35                  40                  45

Gly Met Ser Gly Val Gly Trp Ile Asn Asp Leu Thr Thr Glu Gln Ile
    50                  55                  60

Asn Thr Ala Tyr Gly Ser Gly Val Gly Gln Ile Gly Leu Ser Ile Met
65                  70                  75                  80

Arg Val Arg Ile Asp Pro Asp Ser Ser Lys Trp Asn Ile Gln Leu Pro
                85                  90                  95

Ser Ala Arg Gln Ala Val Ser Leu Gly Ala Lys Ile Met Ala Thr Pro
            100                 105                 110

Trp Ser Pro Pro Ala Tyr Met Lys Ser Asn Asn Ser Leu Ile Asn Gly
        115                 120                 125

Gly Arg Leu Leu Pro Ala Asn Tyr Ser Ala Tyr Thr Ser His Leu Leu
    130                 135                 140

Asp Phe Ser Lys Tyr Met Gln Thr Asn Gly Ala Pro Leu Tyr Ala Ile
145                 150                 155                 160

Ser Ile Gln Asn Glu Pro Asp Trp Lys Pro Asp Tyr Glu Ser Cys Glu
                165                 170                 175

Trp Ser Gly Asp Glu Phe Lys Ser Tyr Leu Lys Ser Gln Gly Ser Lys
            180                 185                 190
```

-continued

Phe Gly Ser Leu Lys Val Ile Val Ala Glu Ser Leu Gly Phe Asn Pro
            195                 200                 205

Ala Leu Thr Asp Pro Val Leu Lys Asp Ser Asp Ala Ser Lys Tyr Val
    210                 215                 220

Ser Ile Ile Gly Gly His Leu Tyr Gly Thr Thr Pro Lys Pro Tyr Pro
225                 230                 235                 240

Leu Ala Gln Asn Ala Gly Lys Gln Leu Trp Met Thr Glu His Tyr Val
                245                 250                 255

Asp Ser Lys Gln Ser Ala Asn Asn Trp Thr Ser Ala Ile Glu Val Gly
                260                 265                 270

Thr Glu Leu Asn Ala Ser Met Val Ser Asn Tyr Ser Ala Tyr Val Trp
            275                 280                 285

Trp Tyr Ile Arg Arg Ser Tyr Gly Leu Leu Thr Glu Asp Gly Lys Val
        290                 295                 300

Ser Lys Arg Gly Tyr Val Met Ser Gln Tyr Ala Arg Phe Val Arg Pro
305                 310                 315                 320

Gly Ala Leu Arg Ile Gln Ala Thr Glu Asn Pro Gln Ser Asn Val His
                325                 330                 335

Leu Thr Ala Tyr Lys Asn Thr Asp Gly Lys Met Val Ile Val Ala Val
            340                 345                 350

Asn Thr Asn Asp Ser Asp Gln Met Leu Ser Leu Asn Ile Ser Asn Ala
        355                 360                 365

Asn Val Thr Lys Phe Glu Lys Tyr Ser Thr Ser Ala Ser Leu Asn Val
    370                 375                 380

Glu Tyr Gly Gly Ser Ser Gln Val Asp Ser Ser Gly Lys Ala Thr Val
385                 390                 395                 400

Trp Leu Asn Pro Leu Ser Val Thr Thr Phe Val Ser Lys
                405                 410

<210> SEQ ID NO 6
<211> LENGTH: 422
<212> TYPE: PRT
<213> ORGANISM: Bacillus subtilis

<400> SEQUENCE: 6

Met Ile Pro Arg Ile Lys Lys Thr Ile Cys Val Leu Leu Val Cys Phe
1               5                   10                  15

Thr Met Leu Ser Val Met Leu Gly Pro Gly Ala Thr Glu Val Leu Ala
            20                  25                  30

Ala Ser Asp Val Thr Val Asn Val Ser Ala Glu Lys Gln Val Ile Arg
        35                  40                  45

Gly Phe Gly Gly Met Asn His Pro Ala Trp Ala Gly Asp Leu Thr Ala
    50                  55                  60

Ala Gln Arg Glu Thr Ala Phe Gly Asn Gly Gln Asn Leu Gly Phe
65                  70                  75                  80

Ser Ile Leu Arg Ile His Val Asp Glu Asn Arg Asn Trp Tyr Lys
                85                  90                  95

Glu Val Glu Thr Ala Lys Ser Ala Val Lys His Gly Ala Ile Val Phe
            100                 105                 110

Ala Ser Pro Trp Asn Pro Pro Ser Asp Met Val Glu Thr Phe Asn Arg
        115                 120                 125

Asn Gly Asp Thr Ser Ala Lys Arg Leu Lys Tyr Asn Lys Tyr Ala Ala
    130                 135                 140

Tyr Ala Gln His Leu Asn Asp Phe Val Thr Phe Met Lys Asn Asn Gly
145                 150                 155                 160

```
Val Asn Leu Tyr Ala Ile Ser Val Gln Asn Glu Pro Asp Tyr Ala His
                165                 170                 175

Glu Trp Thr Trp Trp Thr Pro Gln Glu Ile Leu Arg Phe Met Arg Glu
            180                 185                 190

Asn Ala Gly Ser Ile Asn Ala Arg Val Ile Ala Pro Glu Ser Phe Gln
        195                 200                 205

Tyr Leu Lys Asn Leu Ser Asp Pro Ile Leu Asn Asp Pro Gln Ala Leu
    210                 215                 220

Ala Asn Met Asp Ile Leu Gly Thr His Leu Tyr Gly Thr Gln Val Ser
225                 230                 235                 240

Gln Phe Pro Tyr Pro Leu Phe Lys Gln Lys Gly Ala Gly Lys Asp Leu
                245                 250                 255

Trp Met Thr Glu Val Tyr Tyr Pro Asn Ser Asp Thr Asn Ser Ala Asp
            260                 265                 270

Arg Trp Pro Glu Ala Leu Asp Val Ser Gln His Ile His Asn Ala Met
        275                 280                 285

Val Glu Gly Asp Phe Gln Ala Tyr Val Trp Trp Tyr Ile Arg Arg Ser
    290                 295                 300

Tyr Gly Pro Met Lys Glu Asp Gly Thr Ile Ser Lys Arg Gly Tyr Asn
305                 310                 315                 320

Met Ala His Phe Ser Lys Phe Val Arg Pro Gly Tyr Val Arg Ile Asp
                325                 330                 335

Ala Thr Lys Asn Pro Asn Ala Asn Val Tyr Val Ser Ala Tyr Lys Gly
            340                 345                 350

Asp Asn Lys Val Val Ile Val Ala Ile Asn Lys Ser Asn Thr Gly Val
        355                 360                 365

Asn Gln Asn Phe Val Leu Gln Asn Gly Ser Ala Ser Asn Val Ser Arg
    370                 375                 380

Trp Ile Thr Ser Ser Ser Asn Leu Gln Pro Gly Thr Asn Leu Thr
385                 390                 395                 400

Val Ser Gly Asn His Phe Trp Ala His Leu Pro Ala Gln Ser Val Thr
                405                 410                 415

Thr Phe Val Val Asn Arg
            420

<210> SEQ ID NO 7
<211> LENGTH: 547
<212> TYPE: PRT
<213> ORGANISM: Bacteroides ovatus

<400> SEQUENCE: 7

Met Lys Asn Ile Thr Leu Leu Phe Cys Leu Phe Leu Ala Asn Ile Leu
1               5                   10                  15

Leu Gly Ala Cys Ser Gly Gly Glu Asp Glu Lys Lys Glu Met Asp Glu
            20                  25                  30

Gly Lys Gly Ala Tyr Ala Leu Phe Leu Lys Lys Ser Ile Thr Val Ser
        35                  40                  45

Thr Gly Glu Ser Gln Thr Asp Val Val Glu Trp Ala Lys Thr Ser
    50                  55                  60

Trp Glu Ile Thr Leu Gly Glu Gly Asp Ile Val Lys Ser Val Thr Pro
65                  70                  75                  80

Thr Ser Gly Gly Ser Asn Thr Gly Glu Lys Gln Tyr Thr Lys Val Arg
                85                  90                  95

Val Ser Cys Gly Ala Asn Ser Thr Met Lys Lys Arg Thr Gln Thr Ile
            100                 105                 110
```

-continued

```
His Leu Phe Asp Lys Thr Asn Glu Thr Thr Val Asp Leu Leu Val Glu
            115                 120                 125

Gln Glu Pro Pro Phe Lys Ser Val Thr Leu Thr Val Asp Pro Ser Val
130                 135                 140

Lys Tyr Gln Pro Val Val Gly Phe Gly Gly Met Tyr Asn Pro Lys Ile
145                 150                 155                 160

Trp Cys Gly Asp Asn Leu Ile Ser Ala Ser Gln Leu Asp Lys Met Tyr
                165                 170                 175

Gly Ala Gly Gly Leu Gly Tyr Ser Ile Leu Arg Leu Met Ile Tyr Pro
            180                 185                 190

Asn Glu Ser Asp Trp Ser Ala Asp Val Glu Ala Ala Lys Ala Ala Gln
        195                 200                 205

Ala Asn Gly Ala Ile Ile Phe Ala Cys Pro Trp Asp Cys Thr Asp Ala
210                 215                 220

Leu Ala Asp Lys Ile Thr Val Asn Gly Lys Glu Met Lys His Leu Lys
225                 230                 235                 240

Lys Glu Asn Tyr Glu Ala Tyr Ala Asn His Leu Ile Arg Tyr Val Thr
                245                 250                 255

Phe Met Lys Glu Lys Gly Val Asn Leu Tyr Ala Ile Ser Val Gln Asn
            260                 265                 270

Glu Pro Asp Met Glu Phe Thr Tyr Trp Thr Pro Ser Glu Val Val Asp
        275                 280                 285

Phe Val Lys Gln Tyr Gly Ala Arg Ile Arg Glu Thr Gly Val Lys Leu
    290                 295                 300

Met Ser Pro Glu Ala Cys Gly Met Gln Pro Glu Tyr Thr Asp Pro Ile
305                 310                 315                 320

Ile Asn Asn Ala Glu Ala Phe Ala Gln Thr Asp Ile Leu Ala Gly His
                325                 330                 335

Leu Tyr Gln Gly Phe Thr Asp Leu Ser Ser Gly Tyr Val Lys Asn Arg
            340                 345                 350

His Asp Tyr Ile Cys Gly Val Tyr Ser Arg Ile Gln Gly Lys Thr Trp
        355                 360                 365

Trp Met Thr Glu His Leu Phe Asn Asp Gly Glu Asn Ser Asp Asp Ser
    370                 375                 380

Ser Lys Trp Glu Phe Leu Lys Trp Gln Tyr Ser Leu Asn His Leu Gly
385                 390                 395                 400

Lys Glu Ile His Met Cys Met Glu Gly Tyr Cys Ser Ala Tyr Ile Tyr
                405                 410                 415

Trp Tyr Leu Lys Arg Phe Tyr Gly Leu Met Gly Asp Thr Asp Lys Arg
            420                 425                 430

Ser Pro Thr Ser Glu Gly Glu Ile Thr Lys Asn Gly Tyr Ile Met Ala
        435                 440                 445

His Tyr Ala Gln Tyr Ala Thr Glu Thr Thr Arg Ile Lys Val Val Thr
    450                 455                 460

Asn Asn Glu Glu Val Cys Ala Thr Ala Tyr Trp Asp Glu Lys Thr Gly
465                 470                 475                 480

Glu Val Thr Ile Val Leu Leu Asn Leu Asn Gly Ala Ser Gln Trp Leu
                485                 490                 495

Glu Ile Pro Leu Ala Gly Ile Lys Lys Ala Ser Ala Val Glu Thr Asn
            500                 505                 510

Glu Thr Lys Asn Met Glu Val Ile Asp Thr Gly Leu Met Glu Ser Ala
        515                 520                 525
```

```
Glu Gly Ile Thr Val Leu Leu Ser Ala Asn Ser Ile Thr Ser Val Arg
            530                 535                 540

Leu Thr Phe
545

<210> SEQ ID NO 8
<211> LENGTH: 502
<212> TYPE: PRT
<213> ORGANISM: Bacteroides ovatus

<400> SEQUENCE: 8

Met Glu Lys Gln Ser Phe Ser Asp Gly Leu Phe Ser Pro Leu Gly Ile
1               5                   10                  15

Lys Arg Val Ile Phe Met Leu Val Leu Leu Thr Thr Ser Phe Ile Ser
            20                  25                  30

Cys Ser Asn Ser Asp Glu Lys Gly Gly Ser Leu Glu Val Ala Gln Glu
        35                  40                  45

Tyr Arg Asn Leu Glu Phe Asp Ala Arg Gly Ser Arg Gln Thr Ile Gln
    50                  55                  60

Ile Asp Gly Pro Ala Glu Trp His Ile Ser Thr Ser Glu Ser Trp Cys
65                  70                  75                  80

Lys Ser Ser His Thr Ile Gly Glu Gly Lys Gln Tyr Val Asn Ile Thr
                85                  90                  95

Val Glu Ala Asn Asp Thr Gln Lys Glu Arg Thr Ala Thr Val Thr Val
            100                 105                 110

Ser Ala Ser Gly Ala Pro Asp Ile Ile Asn Val Lys Gln Ser Leu
        115                 120                 125

Tyr Ser Val Pro Ala Tyr Asp Glu Tyr Ile Ala Pro Asp Asn Thr Gly
    130                 135                 140

Met Arg Asp Leu Thr Ser Met Gln Leu Ser Ala Leu Met Lys Ala Gly
145                 150                 155                 160

Val Asn Val Gly Asn Thr Phe Glu Ala Val Ile Val Gly Asn Asp Gly
                165                 170                 175

Ser Leu Ser Gly Asp Glu Thr Cys Trp Gly Asn Pro Thr Pro Asn Lys
            180                 185                 190

Val Leu Phe Glu Gly Ile Lys Ala Ala Gly Phe Asp Val Val Arg Ile
        195                 200                 205

Pro Val Ala Tyr Ser His Gln Phe Glu Asp Ala Thr Tyr Lys Ile
    210                 215                 220

Lys Ser Ala Trp Met Asp Lys Val Glu Ala Val Lys Ala Ala Leu
225                 230                 235                 240

Asp Ala Gly Leu Tyr Val Ile Ile Asn Ile His Trp Glu Gly Gly Trp
                245                 250                 255

Leu Asn His Pro Val Asp Ala Asn Lys Glu Ala Leu Asp Glu Arg Leu
            260                 265                 270

Glu Ala Met Trp Lys Gln Ile Ala Leu Arg Phe Arg Asp Tyr Asp Asp
        275                 280                 285

Arg Leu Leu Phe Ala Gly Thr Asn Glu Val Asn Asn Asp Asp Ala Asn
    290                 295                 300

Gly Ala Gln Pro Thr Glu Glu Asn Tyr Arg Val Gln Asn Gly Phe Asn
305                 310                 315                 320

Gln Val Phe Val Asn Thr Val Arg Ala Thr Gly Gly Arg Asn His Tyr
                325                 330                 335

Arg His Leu Ile Val Gln Ala Tyr Asn Thr Asp Val Ala Lys Ala Val
            340                 345                 350
```

```
Ala His Phe Thr Met Pro Leu Asp Ile Val Gln Asn Arg Ile Phe Leu
            355                 360                 365

Glu Cys His Tyr Tyr Asp Pro Tyr Asp Phe Thr Ile Met Pro Asn Asp
370                 375                 380

Glu Asn Phe Lys Ser Gln Trp Gly Ala Ala Phe Ala Gly Gly Asp Val
385                 390                 395                 400

Ser Ala Thr Gly Gln Glu Gly Asp Ile Glu Ala Thr Leu Ser Ser Leu
                405                 410                 415

Asn Val Phe Ile Asn Asn Asn Val Pro Val Ile Gly Glu Tyr Gly
            420                 425                 430

Pro Thr Leu Arg Asp Gln Leu Thr Gly Glu Ala Leu Glu Asn His Leu
            435                 440                 445

Lys Ser Arg Asn Asp Tyr Ile Glu Tyr Val Val Lys Thr Cys Val Lys
            450                 455                 460

Asn Lys Leu Val Pro Leu Tyr Trp Asp Ala Gly Tyr Thr Glu Lys Leu
465                 470                 475                 480

Phe Asp Arg Thr Thr Gly Gln Pro His Asn Ala Ala Ser Ile Ala Ala
                485                 490                 495

Ile Met Lys Gly Leu Asn
            500

<210> SEQ ID NO 9
<211> LENGTH: 838
<212> TYPE: PRT
<213> ORGANISM: Trichoderma reesei

<400> SEQUENCE: 9

Met Lys Val Ser Arg Val Leu Ala Leu Val Leu Gly Ala Val Ile Pro
1               5                   10                  15

Ala His Ala Ala Phe Ser Trp Lys Asn Val Lys Leu Gly Gly Gly Gly
            20                  25                  30

Gly Phe Val Pro Gly Ile Ile Phe His Pro Lys Thr Lys Gly Val Ala
        35                  40                  45

Tyr Ala Arg Thr Asp Ile Gly Gly Leu Tyr Arg Leu Asn Ala Asp Asp
    50                  55                  60

Ser Trp Thr Ala Val Thr Asp Gly Ile Ala Asp Asn Ala Gly Trp His
65                  70                  75                  80

Asn Trp Gly Ile Asp Ala Val Ala Leu Asp Pro Gln Asp Asp Gln Lys
                85                  90                  95

Val Tyr Ala Ala Val Gly Met Tyr Thr Asn Ser Trp Asp Pro Ser Asn
            100                 105                 110

Gly Ala Ile Ile Arg Ser Ser Asp Arg Gly Ala Thr Trp Ser Phe Thr
        115                 120                 125

Asn Leu Pro Phe Lys Val Gly Gly Asn Met Pro Gly Arg Gly Ala Gly
    130                 135                 140

Glu Arg Leu Ala Val Asp Pro Ala Asn Ser Asn Ile Ile Tyr Phe Gly
145                 150                 155                 160

Ala Arg Ser Gly Asn Gly Leu Trp Lys Ser Thr Asp Gly Gly Val Thr
                165                 170                 175

Phe Ser Lys Val Ser Ser Phe Thr Ala Thr Gly Thr Tyr Ile Pro Asp
            180                 185                 190

Pro Ser Asp Ser Asn Gly Tyr Asn Ser Asp Lys Gln Gly Leu Met Trp
        195                 200                 205

Val Thr Phe Asp Ser Thr Ser Thr Thr Gly Gly Ala Thr Ser Arg
    210                 215                 220
```

```
Ile Phe Val Gly Thr Ala Asp Asn Ile Thr Ala Ser Val Tyr Val Ser
225                 230                 235                 240

Thr Asn Ala Gly Ser Thr Trp Ser Ala Val Pro Gly Gln Pro Gly Lys
            245                 250                 255

Tyr Phe Pro His Lys Ala Lys Leu Gln Pro Ala Glu Lys Ala Leu Tyr
        260                 265                 270

Leu Thr Tyr Ser Asp Gly Thr Gly Pro Tyr Asp Gly Thr Leu Gly Ser
    275                 280                 285

Val Trp Arg Tyr Asp Ile Ala Gly Gly Thr Trp Lys Asp Ile Thr Pro
290                 295                 300

Val Ser Gly Ser Asp Leu Tyr Phe Gly Phe Gly Leu Gly Leu Asp
305                 310                 315                 320

Leu Gln Lys Pro Gly Thr Leu Val Val Ala Ser Leu Asn Ser Trp Trp
                325                 330                 335

Pro Asp Ala Gln Leu Phe Arg Ser Thr Asp Ser Gly Thr Thr Trp Ser
                340                 345                 350

Pro Ile Trp Ala Trp Ala Ser Tyr Pro Thr Glu Thr Tyr Tyr Tyr Ser
            355                 360                 365

Ile Ser Thr Pro Lys Ala Pro Trp Ile Lys Asn Asn Phe Ile Asp Val
370                 375                 380

Thr Ser Glu Ser Pro Ser Asp Gly Leu Ile Lys Arg Leu Gly Trp Met
385                 390                 395                 400

Ile Glu Ser Leu Glu Ile Asp Pro Thr Asp Ser Asn His Trp Leu Tyr
                405                 410                 415

Gly Thr Gly Met Thr Ile Phe Gly Gly His Asp Leu Thr Asn Trp Asp
            420                 425                 430

Thr Arg His Asn Val Ser Ile Gln Ser Leu Ala Asp Gly Ile Glu Glu
        435                 440                 445

Phe Ser Val Gln Asp Leu Ala Ser Ala Pro Gly Gly Ser Glu Leu Leu
450                 455                 460

Ala Ala Val Gly Asp Asp Asn Gly Phe Thr Phe Ala Ser Arg Asn Asp
465                 470                 475                 480

Leu Gly Thr Ser Pro Gln Thr Val Trp Ala Thr Pro Thr Trp Ala Thr
            485                 490                 495

Ser Thr Ser Val Asp Tyr Ala Gly Asn Ser Val Lys Ser Val Val Arg
        500                 505                 510

Val Gly Asn Thr Ala Gly Thr Gln Gln Val Ala Ile Ser Ser Asp Gly
        515                 520                 525

Gly Ala Thr Trp Ser Ile Asp Tyr Ala Ala Asp Thr Ser Met Asn Gly
530                 535                 540

Gly Thr Val Ala Tyr Ser Ala Asp Gly Asp Thr Ile Leu Trp Ser Thr
545                 550                 555                 560

Ala Ser Ser Gly Val Gln Arg Ser Gln Phe Gln Gly Ser Phe Ala Ser
                565                 570                 575

Val Ser Ser Leu Pro Ala Gly Ala Val Ile Ala Ser Asp Lys Lys Thr
            580                 585                 590

Asn Ser Val Phe Tyr Ala Gly Ser Gly Thr Phe Tyr Val Ser Lys
        595                 600                 605

Asp Thr Gly Ser Ser Phe Thr Arg Gly Pro Lys Leu Gly Ser Ala Gly
        610                 615                 620

Thr Ile Arg Asp Ile Ala Ala His Pro Thr Thr Ala Gly Thr Leu Tyr
625                 630                 635                 640
```

```
Val Ser Thr Asp Val Gly Ile Phe Arg Ser Thr Asp Ser Gly Thr Thr
                645                 650                 655

Phe Gly Gln Val Ser Thr Ala Leu Thr Asn Thr Tyr Gln Ile Ala Leu
            660                 665                 670

Gly Val Gly Ser Gly Ser Asn Trp Asn Leu Tyr Ala Phe Gly Thr Gly
        675                 680                 685

Pro Ser Gly Ala Arg Leu Tyr Ala Ser Gly Asp Ser Gly Ala Ser Trp
690                 695                 700

Thr Asp Ile Gln Gly Ser Gln Gly Phe Gly Ser Ile Asp Ser Thr Lys
705                 710                 715                 720

Val Ala Gly Ser Gly Ser Thr Ala Gly Gln Val Tyr Val Gly Thr Asn
            725                 730                 735

Gly Arg Gly Val Phe Tyr Ala Gln Gly Thr Val Gly Gly Gly Thr Gly
        740                 745                 750

Gly Thr Ser Ser Ser Thr Lys Gln Ser Ser Ser Thr Ser Ser Ala
    755                 760                 765

Ser Ser Ser Thr Thr Leu Arg Ser Ser Val Val Ser Thr Thr Arg Ala
770                 775                 780

Ser Thr Val Thr Ser Ser Arg Thr Ser Ser Ala Ala Gly Pro Thr Gly
785                 790                 795                 800

Ser Gly Val Ala Gly His Tyr Ala Gln Cys Gly Gly Ile Gly Trp Thr
            805                 810                 815

Gly Pro Thr Gln Cys Val Ala Pro Tyr Val Cys Gln Lys Gln Asn Asp
            820                 825                 830

Tyr Tyr Tyr Gln Cys Val
            835

<210> SEQ ID NO 10
<211> LENGTH: 513
<212> TYPE: PRT
<213> ORGANISM: Trichoderma reesei

<400> SEQUENCE: 10

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175
```

```
Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
            290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
            325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
            370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr Thr
            450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
            485                 490                 495

Ala Ser Gly Thr Thr Cys Gln Val Leu Asn Pro Tyr Tyr Ser Gln Cys
            500                 505                 510

Leu

<210> SEQ ID NO 11
<211> LENGTH: 471
<212> TYPE: PRT
<213> ORGANISM: Trichoderma reesei

<400> SEQUENCE: 11

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30
```

```
Gln Cys Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
 50                  55                  60

Ala Ala Ser Ser Ser Ser Thr Arg Ala Ala Ser Thr Thr Ser Arg
 65              70                  75                  80

Val Ser Pro Thr Thr Ser Arg Ser Ser Ser Ala Thr Pro Pro Pro Gly
                85                  90                  95

Ser Thr Thr Thr Arg Val Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
                180                 185                 190

Tyr Asp Leu Pro Asp Arg Asp Cys Ala Ala Leu Ala Ser Asn Gly Glu
            195                 200                 205

Tyr Ser Ile Ala Asp Gly Gly Val Ala Lys Tyr Lys Asn Tyr Ile Asp
            210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
            275                 280                 285

Gly His Ala Gly Trp Leu Gly Trp Pro Ala Asn Gln Asp Pro Ala Ala
            290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
            355                 360                 365

Ala Phe Phe Ile Thr Asp Gln Gly Arg Ser Gly Lys Gln Pro Thr Gly
            370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
                420                 425                 430

Pro Arg Phe Asp Ser His Cys Ala Leu Pro Asp Ala Leu Gln Pro Ala
            435                 440                 445
```

Pro Gln Ala Gly Ala Trp Phe Gln Ala Tyr Phe Val Gln Leu Leu Thr
        450                 455                 460

Asn Ala Asn Pro Ser Phe Leu
465                 470

<210> SEQ ID NO 12
<211> LENGTH: 239
<212> TYPE: PRT
<213> ORGANISM: Aspergillus niger

<400> SEQUENCE: 12

Met Lys Leu Pro Val Thr Leu Ala Met Leu Ala Ala Thr Ala Met Gly
1               5                   10                  15

Gln Thr Met Cys Ser Gln Tyr Asp Ser Ala Ser Ser Pro Pro Tyr Ser
            20                  25                  30

Val Asn Gln Asn Leu Trp Gly Glu Tyr Gln Gly Thr Gly Ser Gln Cys
        35                  40                  45

Val Tyr Val Asp Lys Leu Ser Ser Ser Gly Ala Ser Trp His Thr Glu
50                  55                  60

Trp Thr Trp Ser Gly Gly Glu Gly Thr Val Lys Ser Tyr Ser Asn Ser
65                  70                  75                  80

Gly Val Thr Phe Asn Lys Lys Leu Val Ser Asp Val Ser Ser Ile Pro
                85                  90                  95

Thr Ser Val Glu Trp Lys Gln Asp Asn Thr Asn Val Asn Ala Asp Val
            100                 105                 110

Ala Tyr Asp Leu Phe Thr Ala Ala Asn Val Asp His Ala Thr Ser Ser
        115                 120                 125

Gly Asp Tyr Glu Leu Met Ile Trp Leu Ala Arg Tyr Gly Asn Ile Gln
130                 135                 140

Pro Ile Gly Lys Gln Ile Ala Thr Ala Thr Val Gly Gly Lys Ser Trp
145                 150                 155                 160

Glu Val Trp Tyr Gly Ser Thr Thr Gln Ala Gly Ala Glu Gln Arg Thr
                165                 170                 175

Tyr Ser Phe Val Ser Glu Ser Pro Ile Asn Ser Tyr Ser Gly Asp Ile
            180                 185                 190

Asn Ala Phe Phe Ser Tyr Leu Thr Gln Asn Gln Gly Phe Pro Ala Ser
        195                 200                 205

Ser Gln Tyr Leu Ile Asn Leu Gln Phe Gly Thr Glu Ala Phe Thr Gly
210                 215                 220

Gly Pro Ala Thr Phe Thr Val Asp Asn Trp Thr Ala Ser Val Asn
225                 230                 235

<210> SEQ ID NO 13
<211> LENGTH: 416
<212> TYPE: PRT
<213> ORGANISM: Aspergillus niger

<400> SEQUENCE: 13

Met Arg Ile Ser Asn Leu Ile Val Ala Ala Ser Ala Ala Ser Met Val
1               5                   10                  15

Ser Ala Leu Pro Ser Arg Gln Met Lys Lys Arg Asp Ser Gly Phe Lys
            20                  25                  30

Trp Val Gly Thr Ser Glu Ser Gly Ala Glu Phe Gly Ser Ala Leu Pro
        35                  40                  45

Gly Thr Leu Gly Thr Asp Tyr Thr Trp Pro Glu Thr Ser Lys Ile Gln
50                  55                  60

```
Val Leu Arg Asn Lys Gly Met Asn Ile Phe Arg Ile Pro Phe Leu Met
 65                  70                  75                  80

Glu Arg Leu Thr Pro Asp Gly Leu Thr Ser Ser Phe Ala Ser Thr Tyr
                 85                  90                  95

Leu Ser Asp Leu Lys Ser Thr Val Glu Phe Val Thr Asn Ser Gly Ala
            100                 105                 110

Tyr Ala Val Leu Asp Pro His Asn Tyr Gly Arg Phe Asp Gly Ser Ile
        115                 120                 125

Ile Thr Ser Thr Ser Asp Phe Lys Thr Trp Trp Lys Asn Val Ala Thr
    130                 135                 140

Glu Phe Ala Asp Asn Asp Lys Val Ile Phe Asp Thr Asn Asn Glu Tyr
145                 150                 155                 160

His Asp Met Glu Gln Ser Leu Val Leu Asp Leu Asn Gln Ala Ala Ile
                165                 170                 175

Asn Gly Ile Arg Ala Ala Gly Ala Thr Thr Gln Tyr Ile Phe Val Glu
            180                 185                 190

Gly Asn Ala Tyr Thr Gly Ala Trp Asp Trp Thr Thr Tyr Asn Asp Asn
        195                 200                 205

Leu Ser Gly Leu Thr Asp Ser Glu Asp Lys Ile Ile Tyr Glu Met His
    210                 215                 220

Gln Tyr Leu Asp Ser Asp Ser Ser Gly Thr Ser Glu Thr Cys Val Ser
225                 230                 235                 240

Ser Thr Ile Gly Gln Glu Arg Leu Glu Lys Ala Thr Glu Trp Leu Lys
                245                 250                 255

Thr Asn Asn Lys Gln Gly Ile Val Gly Glu Phe Ala Gly Gly Val Asn
            260                 265                 270

Ser Val Cys Glu Glu Ala Val Glu Gly Met Leu Ala Tyr Met Ser Glu
        275                 280                 285

Asn Ser Asp Val Trp Val Gly Ala Ser Trp Trp Ser Ala Gly Pro Trp
    290                 295                 300

Trp Gly Thr Tyr Met Tyr Ser Leu Glu Pro Thr Asp Gly Thr Ala Tyr
305                 310                 315                 320

Ser Thr Tyr Leu Pro Ile Leu Glu Lys Tyr Phe Pro Ser Gly Asp Ala
                325                 330                 335

Ser Ala Ser Ser Ser Ala Ser Val Ser Val Ala Ala Ala Thr Ser Thr
            340                 345                 350

Ala Ser Thr Thr Thr Ala Ala Phe Glu Gln Thr Thr Thr Pro Ala Thr
        355                 360                 365

Gln Gly Pro Ser Ala Thr Asn Ser Ala Gly Glu Val Asn Gln Tyr Tyr
    370                 375                 380

Gln Cys Gly Gly Ile Asn Trp Thr Gly Pro Thr Val Cys Ala Ser Pro
385                 390                 395                 400

Tyr Thr Cys Lys Val Gln Asn Asp Tyr Tyr Tyr Gln Cys Val Ala Glu
                405                 410                 415

<210> SEQ ID NO 14
<211> LENGTH: 331
<212> TYPE: PRT
<213> ORGANISM: Aspergillus niger

<400> SEQUENCE: 14

Met Lys Phe Gln Ser Thr Leu Leu Ala Ala Ala Gly Ser Ala
1                5                  10                  15

Leu Ala Val Pro His Gly Ser Gly His Lys Lys Arg Ala Ser Val Phe
             20                  25                  30
```

```
Glu Trp Phe Gly Ser Asn Glu Ser Gly Ala Glu Phe Gly Thr Asn Ile
             35                  40                  45

Pro Gly Val Trp Gly Thr Asp Tyr Ile Phe Pro Asp Pro Ser Thr Ile
 50                  55                  60

Ser Thr Leu Ile Gly Lys Gly Met Asn Phe Phe Arg Val Gln Phe Met
 65                  70                  75                  80

Met Glu Arg Leu Leu Pro Asp Ser Met Thr Gly Ser Tyr Asp Glu Glu
                 85                  90                  95

Tyr Leu Ala Asn Leu Thr Thr Val Val Lys Ala Val Thr Asp Gly Gly
                100                 105                 110

Ala His Ala Leu Ile Asp Pro His Asn Tyr Gly Arg Tyr Asn Gly Glu
            115                 120                 125

Ile Ile Ser Ser Thr Ser Asp Phe Gln Thr Phe Trp Gln Asn Leu Ala
130                 135                 140

Gly Gln Tyr Lys Asp Asn Asp Leu Val Met Phe Asp Thr Asn Asn Glu
145                 150                 155                 160

Tyr Tyr Asp Met Asp Gln Asp Leu Val Leu Asn Leu Asn Gln Ala Ala
                165                 170                 175

Ile Asn Gly Ile Arg Ala Ala Gly Ala Ser Gln Tyr Ile Phe Val Glu
            180                 185                 190

Gly Asn Ser Trp Thr Gly Ala Trp Thr Trp Val Asp Val Asn Asp Asn
        195                 200                 205

Met Lys Asn Leu Thr Asp Pro Glu Asp Lys Ile Val Tyr Glu Met His
210                 215                 220

Gln Tyr Leu Asp Ser Asp Gly Ser Gly Thr Ser Glu Thr Cys Val Ser
225                 230                 235                 240

Gly Thr Ile Gly Lys Glu Arg Ile Thr Asp Ala Thr Gln Trp Leu Lys
                245                 250                 255

Asp Asn Lys Lys Val Gly Phe Ile Gly Glu Tyr Ala Gly Gly Ser Asn
            260                 265                 270

Asp Val Cys Arg Ser Ala Val Ser Gly Met Leu Glu Tyr Met Ala Asn
        275                 280                 285

Asn Thr Asp Val Trp Lys Gly Ala Ser Trp Trp Ala Ala Gly Pro Trp
290                 295                 300

Trp Gly Asp Tyr Ile Phe Ser Leu Glu Pro Pro Asp Gly Thr Ala Tyr
305                 310                 315                 320

Thr Gly Met Leu Asp Ile Leu Glu Thr Tyr Leu
                325                 330

<210> SEQ ID NO 15
<211> LENGTH: 465
<212> TYPE: PRT
<213> ORGANISM: Trichoderma reesei

<400> SEQUENCE: 15

Met Lys Ser Ser Ile Ser Val Val Leu Ala Leu Leu Gly His Ser Ala
 1               5                  10                  15

Ala Trp Ser Tyr Ala Thr Lys Ser Gln Tyr Arg Ala Asn Ile Lys Ile
                 20                  25                  30

Asn Ala Arg Gln Thr Tyr Gln Thr Met Ile Gly Gly Cys Ser Gly
             35                  40                  45

Ala Phe Gly Ile Ala Cys Gln Gln Phe Gly Ser Ser Gly Leu Ser Pro
 50                  55                  60

Glu Asn Gln Gln Lys Val Thr Gln Ile Leu Phe Asp Glu Asn Ile Gly
 65                  70                  75                  80
```

```
Gly Leu Ser Ile Val Arg Asn Asp Ile Gly Ser Ser Pro Gly Thr Thr
                85                  90                  95

Ile Leu Pro Thr Cys Pro Ala Thr Pro Gln Asp Lys Phe Asp Tyr Val
            100                 105                 110

Trp Asp Gly Ser Asp Asn Cys Gln Phe Asn Leu Thr Lys Thr Ala Leu
        115                 120                 125

Lys Tyr Asn Pro Asn Leu Tyr Val Tyr Ala Asp Ala Trp Ser Ala Pro
    130                 135                 140

Gly Cys Met Lys Thr Val Gly Thr Glu Asn Leu Gly Gly Gln Ile Cys
145                 150                 155                 160

Gly Val Arg Gly Thr Asp Cys Lys His Asp Trp Arg Gln Ala Tyr Ala
                165                 170                 175

Asp Tyr Leu Val Gln Tyr Val Arg Phe Tyr Lys Glu Glu Gly Ile Asp
            180                 185                 190

Ile Ser Leu Leu Gly Ala Trp Asn Glu Pro Asp Phe Asn Pro Phe Thr
        195                 200                 205

Tyr Glu Ser Met Leu Ser Asp Gly Tyr Gln Ala Lys Asp Phe Leu Glu
    210                 215                 220

Val Leu Tyr Pro Thr Leu Lys Lys Ala Phe Pro Lys Val Asp Val Ser
225                 230                 235                 240

Cys Cys Asp Ala Thr Gly Ala Arg Gln Glu Arg Asn Ile Leu Tyr Glu
                245                 250                 255

Leu Gln Gln Ala Gly Gly Glu Arg Tyr Phe Asp Ile Ala Thr Trp His
            260                 265                 270

Asn Tyr Gln Ser Asn Pro Glu Arg Pro Phe Asn Ala Gly Gly Lys Pro
        275                 280                 285

Asn Ile Gln Thr Glu Trp Ala Asp Gly Thr Gly Pro Trp Asn Ser Thr
    290                 295                 300

Trp Asp Tyr Ser Gly Gln Leu Ala Glu Gly Leu Gln Trp Ala Leu Tyr
305                 310                 315                 320

Met His Asn Ala Phe Val Asn Ser Asp Thr Ser Gly Tyr Thr His Trp
                325                 330                 335

Trp Cys Ala Gln Asn Thr Asn Gly Asp Asn Ala Leu Ile Arg Leu Asp
            340                 345                 350

Arg Asp Ser Tyr Glu Val Ser Ala Arg Leu Trp Ala Phe Ala Gln Tyr
        355                 360                 365

Phe Arg Phe Ala Arg Pro Gly Ser Val Arg Ile Gly Ala Thr Ser Asp
    370                 375                 380

Val Glu Asn Val Tyr Val Thr Ala Tyr Val Asn Lys Asn Gly Thr Val
385                 390                 395                 400

Ala Ile Pro Val Ile Asn Ala Ala His Phe Pro Tyr Asp Leu Thr Ile
                405                 410                 415

Asp Leu Glu Gly Ile Lys Lys Arg Lys Leu Ser Glu Tyr Leu Thr Asp
            420                 425                 430

Asn Ser His Asn Val Thr Leu Gln Ser Arg Tyr Lys Val Ser Gly Ser
        435                 440                 445

Ser Leu Lys Val Thr Val Glu Pro Arg Ala Met Lys Thr Phe Trp Leu
450                 455                 460

Glu
465
```

```
<210> SEQ ID NO 16
<211> LENGTH: 211
<212> TYPE: PRT
<213> ORGANISM: Aspergillus niger

<400> SEQUENCE: 16

Met Lys Val Thr Ala Ala Phe Ala Gly Leu Leu Val Thr Ala Phe Ala
1               5                   10                  15

Ala Pro Val Pro Glu Pro Val Leu Val Ser Arg Ser Ala Gly Ile Asn
            20                  25                  30

Tyr Val Gln Asn Tyr Asn Gly Asn Leu Gly Asp Phe Thr Tyr Asp Glu
        35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Lys Ala Ile Thr
65                  70                  75                  80

Tyr Ser Ala Glu Tyr Ser Ala Ser Gly Ser Ser Ser Tyr Leu Ala Val
                85                  90                  95

Tyr Gly Trp Val Asn Tyr Pro Gln Ala Glu Tyr Tyr Ile Val Glu Asp
            100                 105                 110

Tyr Gly Asp Tyr Asn Pro Cys Ser Ser Ala Thr Ser Leu Gly Thr Val
        115                 120                 125

Tyr Ser Asp Gly Ser Thr Tyr Gln Val Cys Thr Asp Thr Arg Thr Asn
    130                 135                 140

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala Gln His Gly Phe Gly Asn Ser Asp Phe Asn Tyr Gln
            180                 185                 190

Val Met Ala Val Glu Ala Trp Ser Gly Ala Gly Ser Ala Ser Val Thr
        195                 200                 205

Ile Ser Ser
    210

<210> SEQ ID NO 17
<211> LENGTH: 437
<212> TYPE: PRT
<213> ORGANISM: Trichoderma reesei

<400> SEQUENCE: 17

Met Met Met Leu Ser Lys Ser Leu Leu Ser Ala Ala Thr Ala Ala Ser
1               5                   10                  15

Ala Leu Ala Ala Val Leu Gln Pro Val Pro Arg Ala Ser Ser Phe Val
            20                  25                  30

Thr Ile Ser Gly Thr Gln Phe Asn Ile Asp Gly Lys Val Gly Tyr Phe
        35                  40                  45

Ala Gly Thr Asn Cys Tyr Trp Cys Ser Phe Leu Thr Asn His Ala Asp
    50                  55                  60

Val Asp Ser Thr Phe Ser His Ile Ser Ser Gly Leu Lys Val Val
65                  70                  75                  80

Arg Val Trp Gly Phe Asn Asp Val Asn Thr Gln Pro Ser Pro Gly Gln
                85                  90                  95

Ile Trp Phe Gln Lys Leu Ser Ala Thr Gly Ser Thr Ile Asn Thr Gly
            100                 105                 110
```

```
Ala Asp Gly Leu Gln Thr Leu Asp Tyr Val Val Gln Ser Ala Glu Gln
            115                 120                 125

His Asn Leu Lys Leu Ile Ile Pro Phe Val Asn Asn Trp Ser Asp Tyr
        130                 135                 140

Gly Gly Ile Asn Ala Tyr Val Asn Ala Phe Gly Gly Asn Ala Thr Thr
145                 150                 155                 160

Trp Tyr Thr Asn Thr Ala Ala Gln Thr Gln Tyr Arg Lys Tyr Val Gln
                165                 170                 175

Ala Val Val Ser Arg Tyr Ala Asn Ser Thr Ala Ile Phe Ala Trp Glu
            180                 185                 190

Leu Gly Asn Glu Pro Arg Cys Asn Gly Cys Ser Thr Asp Val Ile Val
        195                 200                 205

Gln Trp Ala Thr Ser Val Ser Gln Tyr Val Lys Ser Leu Asp Ser Asn
    210                 215                 220

His Leu Val Thr Leu Gly Asp Glu Gly Leu Gly Leu Ser Thr Gly Asp
225                 230                 235                 240

Gly Ala Tyr Pro Tyr Thr Tyr Gly Glu Gly Thr Asp Phe Ala Lys Asn
                245                 250                 255

Val Gln Ile Lys Ser Leu Asp Phe Gly Thr Phe His Leu Tyr Pro Asp
            260                 265                 270

Ser Trp Gly Thr Asn Tyr Thr Trp Gly Asn Gly Trp Ile Gln Thr His
        275                 280                 285

Ala Ala Ala Cys Leu Ala Ala Gly Lys Pro Cys Val Phe Glu Glu Tyr
    290                 295                 300

Gly Ala Gln Gln Asn Pro Cys Thr Asn Glu Ala Pro Trp Gln Thr Thr
305                 310                 315                 320

Ser Leu Thr Thr Arg Gly Met Gly Gly Asp Met Phe Trp Gln Trp Gly
                325                 330                 335

Asp Thr Phe Ala Asn Gly Ala Gln Ser Asn Ser Asp Pro Tyr Thr Val
            340                 345                 350

Trp Tyr Asn Ser Ser Asn Trp Gln Cys Leu Val Lys Asn His Val Asp
        355                 360                 365

Ala Ile Asn Gly Gly Thr Thr Thr Pro Pro Val Ser Ser Thr Thr
    370                 375                 380

Thr Thr Ser Ser Arg Thr Ser Ser Thr Pro Pro Pro Gly Gly Ser
385                 390                 395                 400

Cys Ser Pro Leu Tyr Gly Gln Cys Gly Gly Ser Gly Tyr Thr Gly Pro
                405                 410                 415

Thr Cys Cys Ala Gln Gly Thr Cys Ile Tyr Ser Asn Tyr Trp Tyr Ser
            420                 425                 430

Gln Cys Leu Asn Thr
        435

<210> SEQ ID NO 18
<211> LENGTH: 335
<212> TYPE: PRT
<213> ORGANISM: Aspergillus niger

<400> SEQUENCE: 18

Met Phe Ala Lys Leu Ser Leu Leu Ser Leu Leu Phe Ser Ser Ala Ala
1               5                   10                  15

Leu Gly Ala Ser Asn Gln Thr Leu Ser Tyr Gly Asn Ile Asp Lys Ser
            20                  25                  30

Ala Thr Pro Glu Ala Arg Ala Leu Leu Lys Tyr Ile Gln Leu Gln Tyr
        35                  40                  45
```

```
Gly Ser His Tyr Ile Ser Gly Gln Gln Asp Ile Asp Ser Trp Asn Trp
 50                  55                  60

Val Glu Lys Asn Ile Gly Val Ala Pro Ala Ile Leu Gly Ser Asp Phe
 65                  70                  75                  80

Thr Tyr Tyr Ser Pro Ser Ala Val Ala His Gly Gly Lys Ser His Ala
                 85                  90                  95

Val Glu Asp Val Ile Gln His Ala Gly Arg Asn Gly Ile Asn Ala Leu
            100                 105                 110

Val Trp His Trp Tyr Ala Pro Thr Cys Leu Leu Asp Thr Ala Lys Glu
        115                 120                 125

Pro Trp Tyr Lys Gly Phe Tyr Thr Glu Ala Thr Cys Phe Asn Val Ser
130                 135                 140

Glu Ala Val Asn Asp His Gly Asn Gly Thr Asn Tyr Lys Leu Leu Leu
145                 150                 155                 160

Arg Asp Ile Asp Ala Ile Ala Ala Gln Ile Lys Arg Leu Asp Gln Ala
                165                 170                 175

Lys Val Pro Ile Leu Phe Arg Pro Leu His Glu Pro Glu Gly Gly Trp
            180                 185                 190

Phe Trp Trp Gly Ala Gln Gly Pro Ala Pro Phe Lys Lys Leu Trp Asp
        195                 200                 205

Ile Leu Tyr Asp Arg Ile Thr Arg Tyr His Asn Leu His Asn Met Val
210                 215                 220

Trp Val Cys Asn Thr Ala Asp Pro Ala Trp Tyr Pro Gly Asn Asp Lys
225                 230                 235                 240

Cys Asp Ile Ala Thr Ile Asp His Tyr Pro Ala Val Gly Asp His Gly
                245                 250                 255

Val Ala Ala Asp Gln Tyr Lys Lys Leu Gln Thr Val Thr Asn Asn Glu
            260                 265                 270

Arg Val Leu Ala Met Ala Glu Val Gly Pro Ile Pro Asp Pro Asp Lys
        275                 280                 285

Gln Ala Arg Glu Asn Val Asn Trp Ala Tyr Trp Met Val Trp Ser Gly
290                 295                 300

Asp Phe Ile Glu Asp Gly Lys Gln Asn Pro Asn Gln Phe Leu His Lys
305                 310                 315                 320

Val Tyr Asn Asp Thr Arg Val Val Ala Leu Asn Trp Glu Gly Ala
                325                 330                 335

<210> SEQ ID NO 19
<211> LENGTH: 383
<212> TYPE: PRT
<213> ORGANISM: Aspergillus niger

<400> SEQUENCE: 19

Met Lys Leu Ser Asn Ala Leu Leu Thr Leu Ala Ser Leu Ala Leu Ala
1               5                   10                  15

Asn Val Ser Thr Ala Leu Pro Lys Ala Ser Pro Ala Pro Ser Thr Ser
            20                  25                  30

Ser Ser Ala Ala Ser Thr Ser Phe Ala Ser Thr Ser Gly Leu Gln Phe
        35                  40                  45

Thr Ile Asp Gly Glu Thr Gly Tyr Phe Ala Gly Thr Asn Ser Tyr Trp
 50                  55                  60

Ile Gly Phe Leu Thr Asp Asn Ala Asp Val Asp Leu Val Met Gly His
 65                  70                  75                  80

Leu Lys Ser Ser Gly Leu Lys Ile Leu Arg Val Trp Gly Phe Asn Asp
                 85                  90                  95
```

```
Val Thr Ser Gln Pro Ser Ser Gly Thr Val Trp Tyr Gln Leu His Gln
            100                 105                 110

Asp Gly Lys Ser Thr Ile Asn Thr Gly Ala Asp Gly Leu Gln Arg Leu
            115                 120                 125

Asp Tyr Val Val Ser Ser Ala Glu Gln His Asp Ile Lys Leu Ile Ile
            130                 135                 140

Asn Phe Val Asn Tyr Trp Thr Asp Tyr Gly Gly Met Ser Ala Tyr Val
145                 150                 155                 160

Ser Ala Tyr Gly Gly Ser Gly Glu Thr Asp Phe Tyr Thr Ser Asp Thr
                165                 170                 175

Met Gln Ser Ala Tyr Gln Thr Tyr Ile Lys Thr Val Val Glu Arg Tyr
            180                 185                 190

Ser Asn Ser Ser Ala Val Phe Ala Trp Glu Leu Ala Asn Glu Pro Arg
            195                 200                 205

Cys Pro Ser Cys Asp Thr Ser Val Leu Tyr Asn Trp Ile Glu Lys Thr
            210                 215                 220

Ser Lys Phe Ile Lys Gly Leu Asp Ala Asp Arg Met Val Cys Ile Gly
225                 230                 235                 240

Asp Glu Gly Phe Gly Leu Asn Ile Asp Ser Asp Gly Ser Tyr Pro Tyr
                245                 250                 255

Gln Phe Ser Glu Gly Leu Asn Phe Thr Met Asn Leu Gly Ile Asp Thr
            260                 265                 270

Ile Asp Phe Gly Thr Leu His Leu Tyr Pro Asp Ser Trp Gly Thr Ser
            275                 280                 285

Asp Asp Trp Gly Asn Gly Trp Ile Thr Ala His Gly Ala Ala Cys Lys
            290                 295                 300

Ala Ala Gly Lys Pro Cys Leu Leu Glu Glu Tyr Gly Val Thr Ser Asn
305                 310                 315                 320

His Cys Ser Val Glu Gly Ser Trp Gln Lys Thr Ala Leu Ser Thr Thr
                325                 330                 335

Gly Val Gly Ala Asp Leu Phe Trp Gln Tyr Gly Asp Asp Leu Ser Thr
            340                 345                 350

Gly Lys Ser Pro Asp Asp Gly Asn Thr Ile Tyr Tyr Gly Thr Ser Asp
            355                 360                 365

Tyr Gln Cys Leu Val Thr Asp His Val Ala Ala Ile Gly Ser Ala
            370                 375                 380

<210> SEQ ID NO 20
<211> LENGTH: 452
<212> TYPE: PRT
<213> ORGANISM: Aspergillus niger

<400> SEQUENCE: 20

Met His Gln Arg Ala Leu Leu Phe Ser Ala Leu Leu Thr Ala Val Arg
1               5                   10                  15

Ala Gln Gln Ala Gly Thr Leu Thr Glu Glu Val His Pro Ser Leu Thr
            20                  25                  30

Trp Gln Lys Cys Thr Ser Glu Gly Ser Cys Thr Glu Gln Ser Gly Ser
            35                  40                  45

Val Val Ile Asp Ser Asn Trp Arg Trp Thr His Ser Val Asn Asp Ser
            50                  55                  60

Thr Asn Cys Tyr Thr Gly Asn Thr Trp Asp Ala Thr Leu Cys Pro Asp
65                  70                  75                  80

Asp Glu Thr Cys Ala Ala Asn Cys Ala Leu Asp Gly Ala Asp Tyr Glu
                85                  90                  95
```

Ser Thr Tyr Gly Val Thr Thr Asp Gly Asp Ser Leu Thr Leu Lys Phe
            100                 105                 110

Val Thr Gly Ser Asn Val Gly Ser Arg Leu Tyr Leu Met Asp Thr Ser
        115                 120                 125

Asp Glu Gly Tyr Gln Thr Phe Asn Leu Leu Asp Ala Glu Phe Thr Phe
    130                 135                 140

Asp Val Asp Val Ser Asn Leu Pro Cys Gly Leu Asn Gly Ala Leu Tyr
145                 150                 155                 160

Phe Thr Ala Met Asp Ala Asp Gly Gly Val Ser Lys Tyr Pro Ala Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Gln Ala Asn Val Asp Gly Trp Glu
        195                 200                 205

Pro Ser Ser Asn Asn Asp Asn Thr Gly Ile Gly Asn His Gly Ser Cys
    210                 215                 220

Cys Pro Glu Met Asp Ile Trp Glu Ala Asn Lys Ile Ser Thr Ala Leu
225                 230                 235                 240

Thr Pro His Pro Cys Asp Ser Ser Glu Gln Thr Met Cys Glu Gly Asn
                245                 250                 255

Asp Cys Gly Gly Thr Tyr Ser Asp Asp Arg Tyr Gly Gly Thr Cys Asp
            260                 265                 270

Pro Asp Gly Cys Asp Phe Asn Pro Tyr Arg Met Gly Asn Asp Ser Phe
        275                 280                 285

Tyr Gly Pro Gly Lys Thr Ile Asp Thr Gly Ser Lys Met Thr Val Val
    290                 295                 300

Thr Gln Phe Ile Thr Asp Gly Ser Gly Ser Leu Ser Glu Ile Lys Arg
305                 310                 315                 320

Tyr Tyr Val Gln Asn Gly Asn Val Ile Ala Asn Ala Asp Ser Asn Ile
                325                 330                 335

Ser Gly Val Thr Gly Asn Ser Ile Thr Thr Asp Phe Cys Thr Ala Gln
            340                 345                 350

Lys Lys Ala Phe Gly Asp Glu Asp Ile Phe Ala Glu His Asn Gly Leu
        355                 360                 365

Ala Gly Ile Ser Asp Ala Met Ser Ser Met Val Leu Ile Leu Ser Leu
    370                 375                 380

Trp Asp Asp Tyr Tyr Ala Ser Met Glu Trp Leu Asp Ser Asp Tyr Pro
385                 390                 395                 400

Glu Asn Ala Thr Ala Thr Asp Pro Gly Val Ala Arg Gly Thr Cys Asp
                405                 410                 415

Ser Glu Ser Gly Val Pro Ala Thr Val Glu Gly Ala His Pro Asp Ser
            420                 425                 430

Ser Val Thr Phe Ser Asn Ile Lys Phe Gly Pro Ile Asn Ser Thr Phe
        435                 440                 445

Ser Ala Ser Ala
    450

<210> SEQ ID NO 21
<211> LENGTH: 536
<212> TYPE: PRT
<213> ORGANISM: Aspergillus niger

<400> SEQUENCE: 21

```
Met Ser Ser Phe Gln Ile Tyr Arg Ala Ala Leu Leu Ser Ile Leu
1               5                  10                 15

Ala Thr Ala Asn Ala Gln Val Gly Thr Tyr Thr Thr Glu Thr His
            20                  25                 30

Pro Ser Leu Thr Trp Gln Thr Cys Thr Ser Asp Gly Ser Cys Thr Thr
        35                  40                  45

Asn Asp Gly Glu Val Val Ile Asp Ala Asn Trp Arg Trp Val His Ser
    50                  55                  60

Thr Ser Ser Ala Thr Asn Cys Tyr Thr Gly Asn Glu Trp Asp Thr Ser
65                  70                  75                  80

Ile Cys Thr Asp Asp Val Thr Cys Ala Ala Asn Cys Ala Leu Asp Gly
                85                  90                  95

Ala Thr Tyr Glu Ala Thr Tyr Gly Val Thr Thr Ser Gly Ser Glu Leu
            100                 105                 110

Arg Leu Asn Phe Val Thr Gln Gly Ser Ser Lys Asn Ile Gly Ser Arg
            115                 120                 125

Leu Tyr Leu Met Ser Asp Asp Ser Asn Tyr Glu Leu Phe Lys Leu Leu
    130                 135                 140

Gly Gln Glu Phe Thr Phe Asp Val Asp Val Ser Asn Leu Pro Cys Gly
145                 150                 155                 160

Leu Asn Gly Ala Leu Tyr Phe Val Ala Met Asp Ala Asp Gly Gly Thr
                165                 170                 175

Ser Glu Tyr Ser Gly Asn Lys Ala Gly Ala Lys Tyr Gly Thr Gly Tyr
            180                 185                 190

Cys Asp Ser Gln Cys Pro Arg Asp Leu Lys Phe Ile Asn Gly Glu Ala
            195                 200                 205

Asn Cys Asp Gly Trp Glu Pro Ser Ser Asn Asn Val Asn Thr Gly Val
    210                 215                 220

Gly Asp His Gly Ser Cys Cys Ala Glu Met Asp Val Trp Glu Ala Asn
225                 230                 235                 240

Ser Ile Ser Asn Ala Phe Thr Ala His Pro Cys Asp Ser Val Ser Gln
                245                 250                 255

Thr Met Cys Asp Gly Asp Ser Cys Gly Gly Thr Tyr Ser Ala Ser Gly
            260                 265                 270

Asp Arg Tyr Ser Gly Thr Cys Asp Pro Asp Gly Cys Asp Tyr Asn Pro
            275                 280                 285

Tyr Arg Leu Gly Asn Thr Asp Phe Tyr Gly Pro Gly Leu Thr Val Asp
    290                 295                 300

Thr Asn Ser Pro Phe Thr Val Val Thr Gln Phe Ile Thr Asp Asp Gly
305                 310                 315                 320

Thr Ser Ser Gly Thr Leu Thr Glu Ile Lys Arg Leu Tyr Val Gln Asn
                325                 330                 335

Gly Glu Val Ile Ala Asn Gly Ala Ser Thr Tyr Ser Ser Val Asn Gly
            340                 345                 350

Ser Ser Ile Thr Ser Ala Phe Cys Glu Ser Glu Lys Thr Leu Phe Gly
            355                 360                 365

Asp Glu Asn Val Phe Asp Lys His Gly Gly Leu Glu Gly Met Gly Glu
    370                 375                 380

Ala Met Ala Lys Gly Met Val Leu Val Leu Ser Leu Trp Asp Asp Tyr
385                 390                 395                 400

Ala Ala Asp Met Leu Trp Leu Asp Ser Asp Tyr Pro Val Asn Ser Ser
                405                 410                 415
```

```
Ala Ser Thr Pro Gly Val Ala Arg Gly Thr Cys Ser Thr Asp Ser Gly
            420                 425                 430

Val Pro Ala Thr Val Glu Ala Glu Ser Pro Asn Ala Tyr Val Thr Tyr
            435                 440                 445

Ser Asn Ile Lys Phe Gly Pro Ile Gly Ser Thr Tyr Ser Ser Gly Ser
            450                 455                 460

Ser Ser Gly Ser Gly Ser Ser Ser Ser Ser Ser Thr Thr Thr Lys
465             470                 475                 480

Ala Thr Ser Thr Thr Leu Lys Thr Thr Ser Thr Thr Ser Ser Gly Ser
            485                 490                 495

Ser Ser Thr Ser Ala Ala Gln Ala Tyr Gly Gln Cys Gly Gly Gln Gly
            500                 505                 510

Trp Thr Gly Pro Thr Thr Cys Val Ser Gly Tyr Thr Cys Thr Tyr Glu
            515                 520                 525

Asn Ala Tyr Tyr Ser Gln Cys Leu
            530                 535

<210> SEQ ID NO 22
<211> LENGTH: 744
<212> TYPE: PRT
<213> ORGANISM: Trichoderma reesei

<400> SEQUENCE: 22

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65              70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
130             135                 140

Ala Gly Pro Leu Gly Lys Thr Pro Gln Gly Gly Arg Asn Trp Glu Gly
145             150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225             230                 235                 240

Thr Trp Ala Cys Glu Asp Gln Tyr Thr Leu Gln Thr Val Leu Lys Asp
                245                 250                 255
```

```
Gln Leu Gly Phe Pro Gly Tyr Val Met Thr Asp Trp Asn Ala Gln His
                260                 265                 270

Thr Thr Val Gln Ser Ala Asn Ser Gly Leu Asp Met Ser Met Pro Gly
            275                 280                 285

Thr Asp Phe Asn Gly Asn Asn Arg Leu Trp Gly Pro Ala Leu Thr Asn
        290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His Is
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
        595                 600                 605

Ser Tyr Thr Lys Phe Asn Tyr Ser Arg Leu Ser Val Leu Ser Thr Ala
610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670
```

```
Ser Ala Pro Arg Thr Pro Pro Lys Gln Leu Arg Gly Phe Ala Lys Leu
            675                 680                 685

Asn Leu Thr Pro Gly Gln Ser Gly Thr Ala Thr Phe Asn Ile Arg Arg
        690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 23
<211> LENGTH: 797
<212> TYPE: PRT
<213> ORGANISM: Trichoderma reesei

<400> SEQUENCE: 23

Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300
```

-continued

Trp Gly Tyr Val Ser Ser Asp Cys Asp Ala Val Tyr Asn Val Phe Asn
305                 310                 315                 320

Pro His Asp Tyr Ala Ser Asn Gln Ser Ala Ala Ser Ser Leu
            325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
            355                 360                 365

Ser Val Thr Arg Leu Tyr Ala Asn Leu Val Arg Leu Gly Tyr Phe Asp
        370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
530                 535                 540

Gly Gly Gly Gln Val Asp Ser Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
        675                 680                 685

Lys Thr Glu Ser Pro Tyr Thr Ala Met Leu Phe Val Arg Thr Ser Asn
    690                 695                 700

Ala Gly Pro Ala Pro Tyr Pro Asn Lys Trp Leu Val Gly Phe Asp Arg
705                 710                 715                 720

```
Leu Ala Asp Ile Lys Pro Gly His Ser Ser Lys Leu Ser Ile Pro Ile
                    725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
        755                 760                 765

Leu Glu Phe Glu Leu Val Gly Glu Val Thr Ile Glu Asn Trp Pro
    770                 775                 780

Leu Glu Glu Gln Gln Ile Lys Asp Ala Thr Pro Asp Ala
785                 790                 795

<210> SEQ ID NO 24
<211> LENGTH: 917
<212> TYPE: PRT
<213> ORGANISM: Trichoderma reesei
<220> FEATURE:
<221> NAME/KEY: MOD_RES
<222> LOCATION: (511)..(511)
<223> OTHER INFORMATION: Any amino acid

<400> SEQUENCE: 24

Met Ala Arg His Ser Ile Gln Leu Asp Lys Gly Trp Thr Phe Arg Gln
1               5                   10                  15

His Gln Gly Ser Ser Pro Glu Trp Leu Pro Val Glu Lys Val Pro Thr
            20                  25                  30

Gln Val His Met Asp Leu Leu Ala Asn Lys Gln Ile Pro Asp Pro Phe
        35                  40                  45

Val Asp Leu Asn Glu Arg Ala Val Gln Trp Ile Gly Tyr Lys Asp Trp
    50                  55                  60

Glu Tyr Gln Val Thr Phe Thr Pro Glu Ala Ala Gln Val Glu Asp Ala
65                  70                  75                  80

Thr Arg Asp Leu Val Phe Asn Gly Leu Asp Thr Phe Ala Thr Val Tyr
                85                  90                  95

Leu Asn Glu Ala Lys Ile Leu Glu Ala Glu Asn Met Phe Val Ser Tyr
            100                 105                 110

Arg Val Asn Val Thr Asp Arg Ile Lys Ala Ser Ser Glu Asn Thr Leu
        115                 120                 125

Arg Ile Val Phe His Ser Ala Ile Val Arg Gly Glu Glu Leu Ile Lys
    130                 135                 140

Glu His Pro Glu His Asn Phe Leu Val Arg Gln Thr Glu Arg Ser Arg
145                 150                 155                 160

Val Pro Val Arg Lys Ala Gln Tyr Asn Trp Gly Trp Asp Trp Gly Pro
                165                 170                 175

Ile Leu Met Thr Ala Gly Pro Trp Lys Pro Val Ala Leu Glu Thr Tyr
            180                 185                 190

Val Ala Arg Ile Asp Asp Val Trp Ala Gln Ser Asp Val Ser Gln Asp
        195                 200                 205

Leu Lys Thr Val Ser Gly Ile Ile Phe Ala Arg Val Ala Gly Arg Pro
    210                 215                 220

Ser Gln Asp Asp Gln Val Ser Leu Thr Leu Ser Leu Asp Gly Lys Ala
225                 230                 235                 240

Val Phe Gln Gln Thr Val Asp Val Ala Ser Ala Lys Asp Gly Leu Ile
                245                 250                 255

Lys Val Pro Phe Lys Leu Glu Asp Pro Lys Leu Trp Tyr Pro Arg Gly
            260                 265                 270
```

```
Tyr Gly Ser Gln Pro Arg Tyr Gln Leu Asn Ala Asp Leu Ala Arg Lys
            275                 280                 285

Ala Ser Asp Ala Ser Gln Ile Asp Ser Leu Ser Lys Leu Val Gly Phe
290                 295                 300

Arg Arg Ala Glu Leu Val Gln Glu Pro Asp Ala Phe Gly Lys Ser Phe
305                 310                 315                 320

Tyr Phe Arg Ile Asn Asn Val Asp Val Phe Ala Gly Gly Ser Cys Trp
                325                 330                 335

Ile Pro Ala Asp Ser Tyr Leu Ala Gly Val Pro Pro Glu Arg Tyr His
            340                 345                 350

Ala Trp Ala Lys Leu Ile Ala Asp Gly Asn Gln Val Met Leu Arg Val
        355                 360                 365

Trp Gly Gly Gly Val Tyr Glu Glu Asp Ala Leu Ile Glu Ala Cys Asp
    370                 375                 380

Glu Leu Gly Ile Leu Val Phe His Asp Phe Gln Phe Ala Cys Ala Ser
385                 390                 395                 400

Tyr Pro Ala Tyr Pro Ser Tyr Leu Glu Asn Leu Glu Val Glu Ala Arg
                405                 410                 415

Gln Gln Ile Arg Arg Leu Arg Thr His Pro Ser Val Ile Ile Trp Ala
            420                 425                 430

Gly Asn Asn Glu Asp Tyr Gln Val Gln Glu Arg Tyr Lys Leu Asp Tyr
        435                 440                 445

Glu Phe Glu Asn Lys Asp Pro Glu Ser Trp Leu Lys Ser Ser Phe Pro
    450                 455                 460

Ala Arg Tyr Ile Tyr Glu His Phe Leu Pro Lys Leu Val Glu Glu Glu
465                 470                 475                 480

Asp Pro Gly Lys Ile Tyr His Pro Ser Ser Pro Trp Gly Asp Gly Lys
                485                 490                 495

Pro Thr Ala Asp Pro Thr Val Gly Asp Ile His Gln Trp Asn Xaa Pro
            500                 505                 510

Pro Pro Pro Ile Ser Thr Gln Ile Thr His Thr Gln His Pro Thr Asp
        515                 520                 525

His Pro Leu His Thr Val Trp His Gly Thr Met Asn Lys Tyr Gln Glu
    530                 535                 540

Ala Val Asn Met Gly Gly Arg Phe Val Ser Glu Phe Gly Met Glu Ala
545                 550                 555                 560

Tyr Pro His Leu Ser Thr Thr Arg Arg Met Ala Ser Asp Pro Ala Gln
                565                 570                 575

Leu Tyr Pro Gly Ser Met Val Leu Asp Ala His Asn Lys Ala Ile Gly
            580                 585                 590

His Glu Arg Arg Met Met Ser Tyr Val Val Asp Asn Phe Arg Pro Arg
        595                 600                 605

His Asp Leu Gly Gly Tyr Thr His Leu Thr Gln Val Val Gln Ser Glu
    610                 615                 620

Thr Met Arg Ala Ala Tyr Lys Ala Trp Arg Arg Gln Trp Gly Lys Pro
625                 630                 635                 640

Gly Ala Arg Arg Cys Gly Gly Ala Leu Val Trp Gln Leu Asn Asp Cys
                645                 650                 655

Trp Pro Thr Met Ser Trp Ala Val Val Asp Tyr Arg Leu Val Lys Lys
            660                 665                 670

Pro Ala Tyr Tyr Ala Ile Ala Arg Ala Leu Arg Arg Val Asp Val Gly
        675                 680                 685
```

```
Val Cys Arg Thr Trp His Asp Trp Thr Gln Thr Gly Ala Trp Val Asp
    690                 695                 700

Glu Asn Ser Gly Leu Val Thr Gly Gln Val Asp His Thr Leu Ala Ala
705                 710                 715                 720

Arg Glu Gly Thr Phe Asp Val Trp Val Ser Ser Asp Thr Gln Pro
                725                 730                 735

Val Ala Leu Asp Leu Val Val Arg Phe Ile Ser Val Arg Thr Gly Arg
            740                 745                 750

Asp Val Val Asp Pro Ile Leu His Ser Arg Val Val Ala Ala Asn
        755                 760                 765

Ser Ala Thr Asp Ile Leu Gln Gly Lys Thr Leu Pro Pro Ser Ile Pro
770                 775                 780

Asn Pro Glu Asp Ile Thr Lys Pro Phe Pro Leu Ala Glu Tyr Asp Pro
785                 790                 795                 800

Tyr Val Val His Ala Thr Ile Thr Asp Ala Ala Thr Gly Thr Val Ile
                805                 810                 815

Ala Ala Asp Thr Ala Trp Pro Glu Pro Ile Lys Tyr Leu Asp Leu Ser
            820                 825                 830

Asp Arg Gly Ile Ala Phe Glu Val Ser Ser Ala Gly Asp Glu Val Val
        835                 840                 845

Val Ser Ala Glu Lys Pro Val Lys Gly Phe Val Phe Glu Glu Val Glu
850                 855                 860

Gly Leu Glu Leu Ser Asp Asn Gly Phe Asp Val Val Pro Gly Glu Lys
865                 870                 875                 880

Gln Leu Val Lys Val Gly Gly Ala Leu Lys Ala Gly Glu Leu Leu Trp
                885                 890                 895

Thr Cys Ile Gly Ala Asp Ser Ala Ser Leu Lys Ile Glu Ala Ser Ser
            900                 905                 910

Ser Leu Ala Pro Arg
        915

<210> SEQ ID NO 25
<211> LENGTH: 344
<212> TYPE: PRT
<213> ORGANISM: Trichoderma reesei

<400> SEQUENCE: 25

Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
    50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125

Thr Leu Glu Phe Phe Lys Ile Asp Gly Val Gly Leu Leu Ser Gly Gly
    130                 135                 140
```

-continued

```
Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
    210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
                260                 265                 270

Ser Gly Pro Thr Ser Arg Thr Thr Thr Thr Ala Arg Thr Thr Gln Ala
                275                 280                 285

Ser Ser Arg Pro Ser Ser Thr Pro Pro Ala Thr Thr Ser Ala Pro Ala
290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
                340
```